(12) United States Patent
Ghali

(10) Patent No.: US 11,515,001 B2
(45) Date of Patent: Nov. 29, 2022

(54) SYSTEMS AND METHODS FOR GENEALOGICAL GRAPHING

(71) Applicant: Eve's Kids Inc., London (CA)

(72) Inventor: Sherif Ghali, London (CA)

(73) Assignee: Eve's Kids Inc., London (CA)

( * ) Notice: Subject to any disclaimer, the term of this patent is extended or adjusted under 35 U.S.C. 154(b) by 483 days.

(21) Appl. No.: 16/423,052

(22) Filed: May 27, 2019

(65) Prior Publication Data
US 2019/0362806 A1   Nov. 28, 2019

Related U.S. Application Data

(60) Provisional application No. 62/677,103, filed on May 28, 2018.

(51) Int. Cl.
*G16B 10/00* (2019.01)
*G06F 16/901* (2019.01)
(Continued)

(52) U.S. Cl.
CPC .......... *G16B 10/00* (2019.02); *G06F 16/288* (2019.01); *G06F 16/54* (2019.01); *G06F 16/9024* (2019.01); *G06K 7/10722* (2013.01); *G06K 7/1417* (2013.01); *G06K 19/06037* (2013.01); *G09B 19/00* (2013.01); *G16B 45/00* (2019.02)

(58) Field of Classification Search
CPC ....... G16B 10/00; G16B 45/00; G06F 16/288; G06F 16/54; G06F 16/9024; G09B 19/06037; G09B 19/00; G06K 7/10722; G06K 7/1417
See application file for complete search history.

(56) References Cited

U.S. PATENT DOCUMENTS

| 6,111,577 A | 8/2000 | Zilles et al. |
| 6,792,398 B1 | 9/2004 | Handley et al. |

(Continued)

FOREIGN PATENT DOCUMENTS

CA    2713122 A1    7/2009

OTHER PUBLICATIONS

Matt Wright, "Relatives Around Me", Jan. 5, 2018 (https://www.familysearch.org/blog/en/relatives/) (Year: 2018).*

*Primary Examiner* — Laura A Gudorf
(74) *Attorney, Agent, or Firm* — Own Innovation; James W. Hinton

(57) ABSTRACT

Computer-implemented methods and systems for automatically generating a genealogical graph for an initial member and a target member are provided. An example system includes a memory and a processor that can operate to: receive an initial member identifier identifying the initial member and a target member identifier identifying the target member; retrieve, from the memory, a set of genealogical data for the initial member and a set of genealogical data for the target member; and determine whether a genealogical connection exists between the initial member and the target member. In response to determining the genealogical connection exists between the initial member and the target member, the processor can generate the genealogical graph to illustrate the determined genealogical connection and a subset of genealogical data from the set of genealogical data for the target member.

19 Claims, 54 Drawing Sheets

(51) Int. Cl.
*G06F 16/28* (2019.01)
*G06F 16/54* (2019.01)
*G16B 45/00* (2019.01)
*G06K 7/10* (2006.01)
*G06K 7/14* (2006.01)
*G09B 19/00* (2006.01)
*G06K 19/06* (2006.01)

(56) References Cited

U.S. PATENT DOCUMENTS

| | | |
|---|---|---|
| 7,102,635 B2 | 9/2006 | Shih et al. |
| 8,576,222 B2 | 11/2013 | Handley et al. |
| 8,704,776 B2 | 4/2014 | Kim |
| 8,723,810 B2 | 5/2014 | Kim |
| 2002/0023097 A1* | 2/2002 | Ripley .................... G06F 16/88 |
| 2010/0070254 A1 | 3/2010 | Tsai et al. |
| 2010/0223281 A1* | 9/2010 | Hon ........................ G06N 5/048 |
| | | 707/769 |
| 2012/0218289 A1* | 8/2012 | Rasmussen ........... G06F 3/0482 |
| | | 345/619 |
| 2017/0329866 A1* | 11/2017 | Macpherson ........... G06F 19/00 |

* cited by examiner

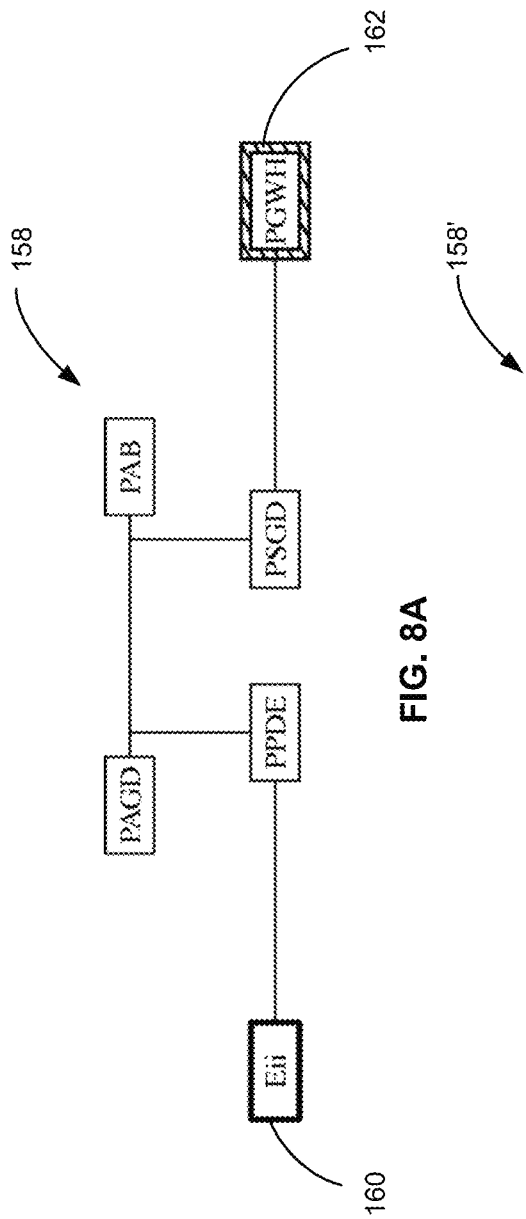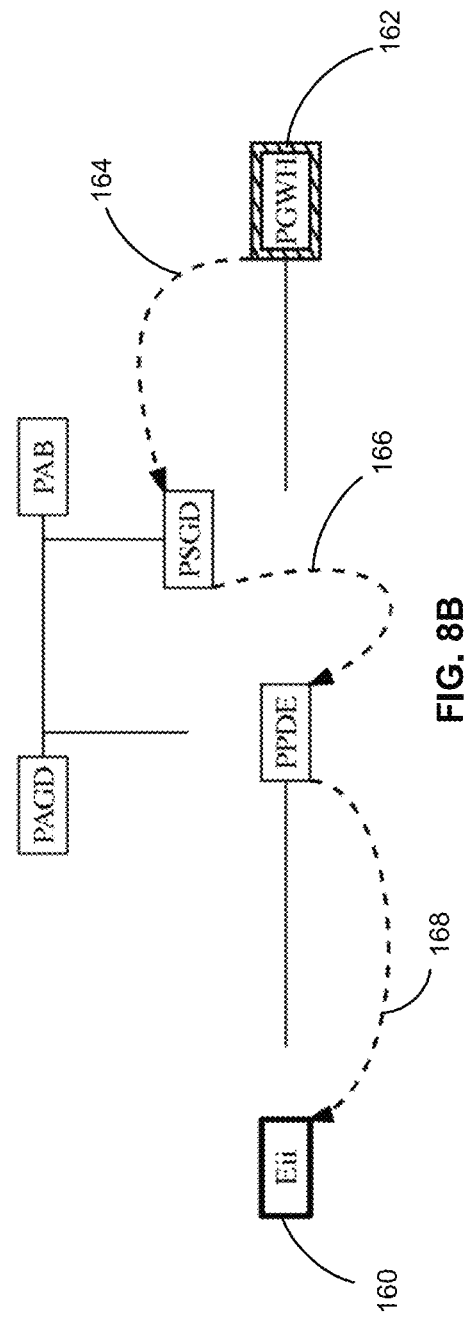

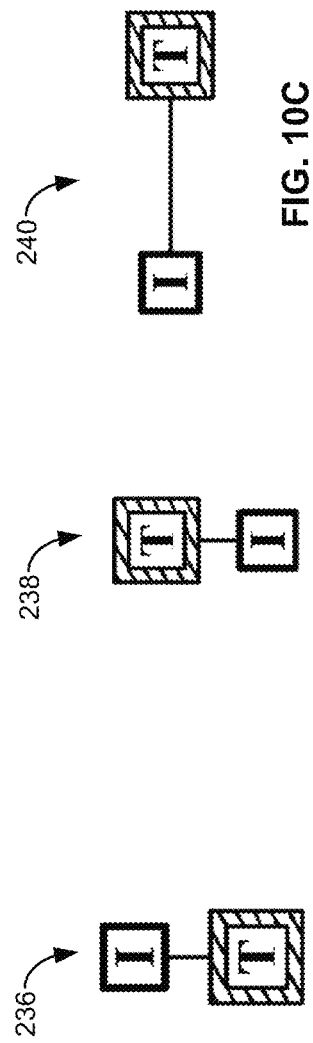
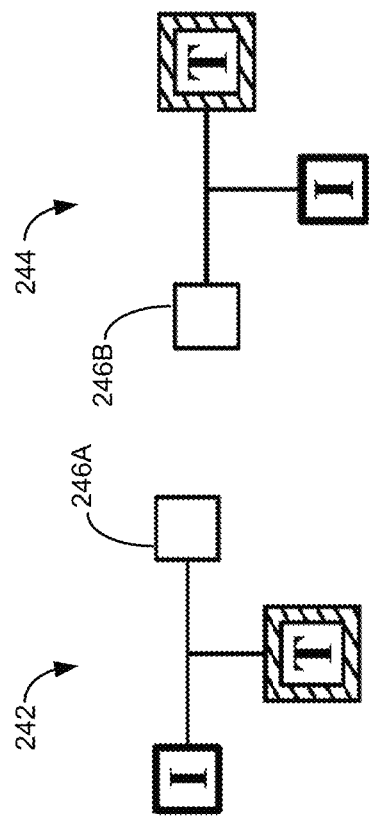

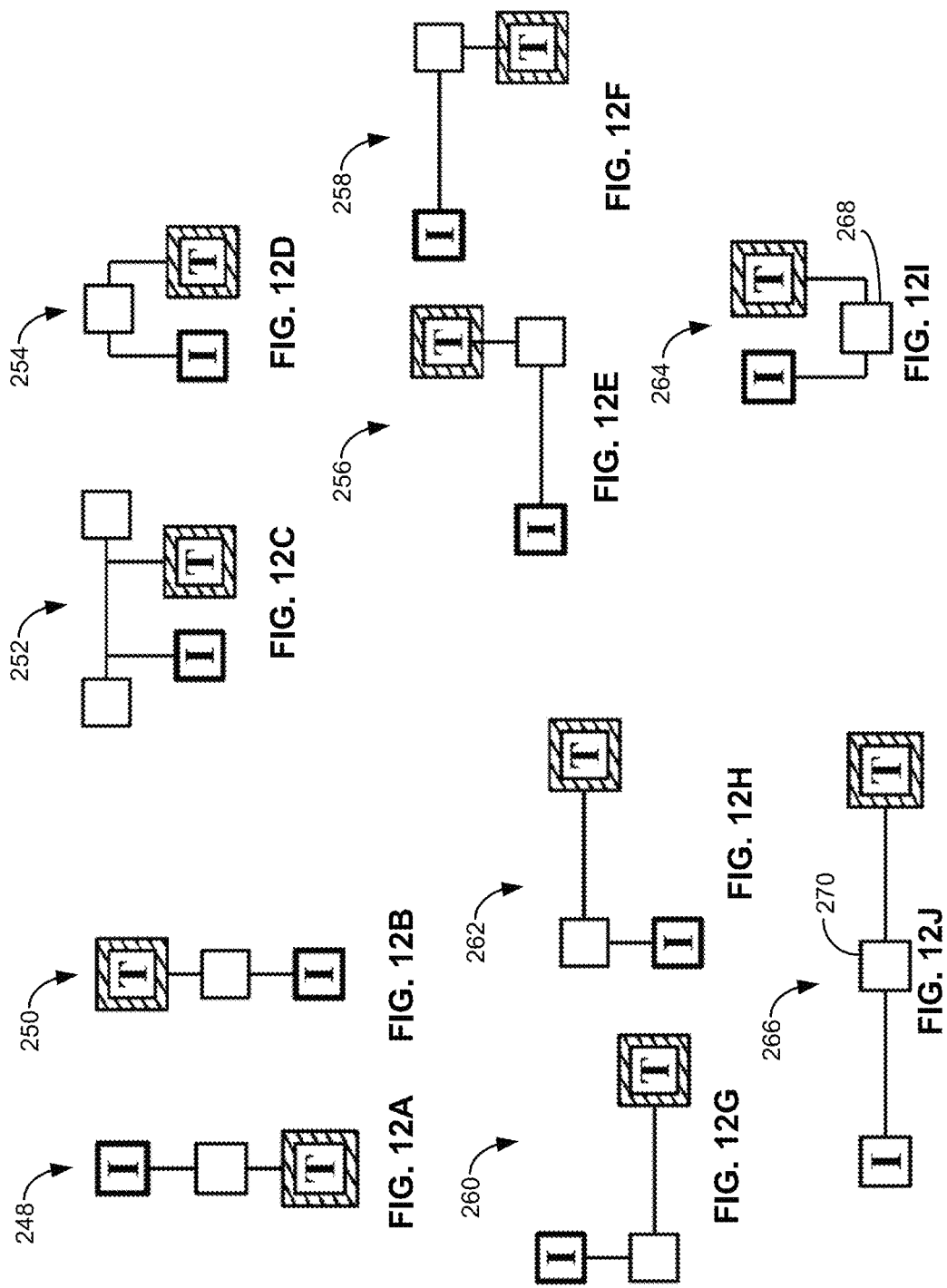

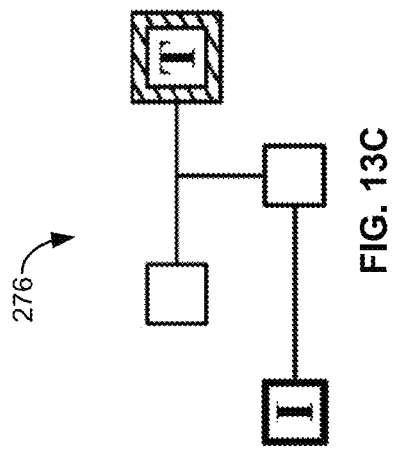
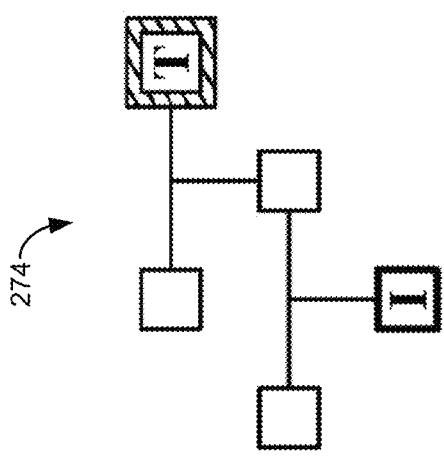
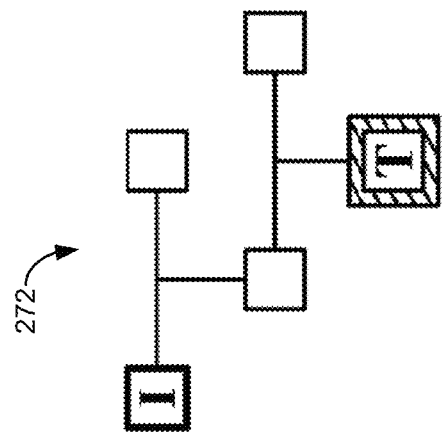
FIG. 13C
FIG. 13B
FIG. 13A

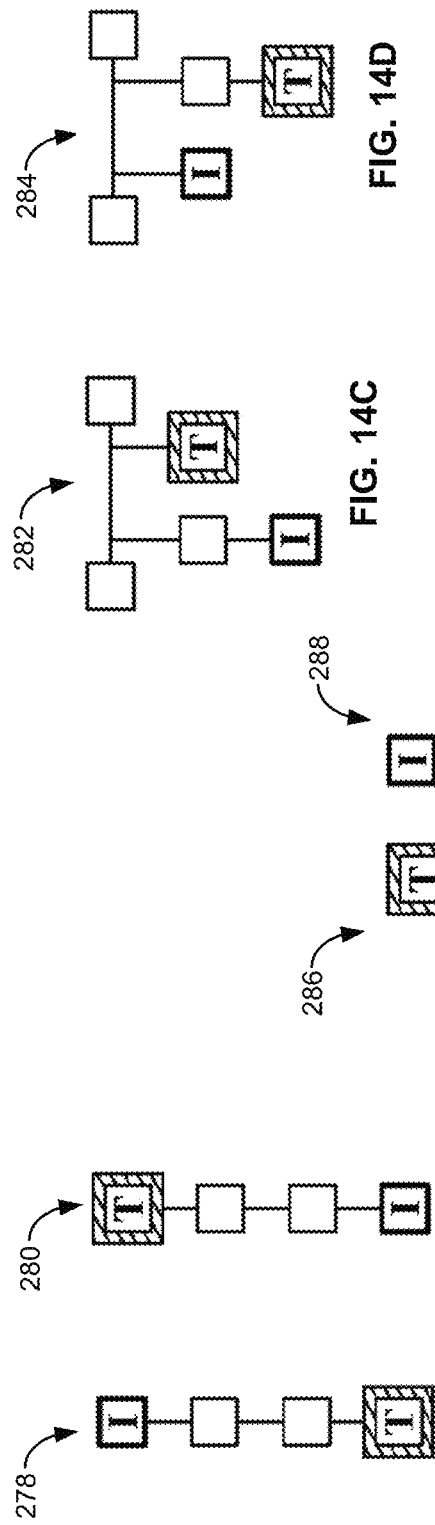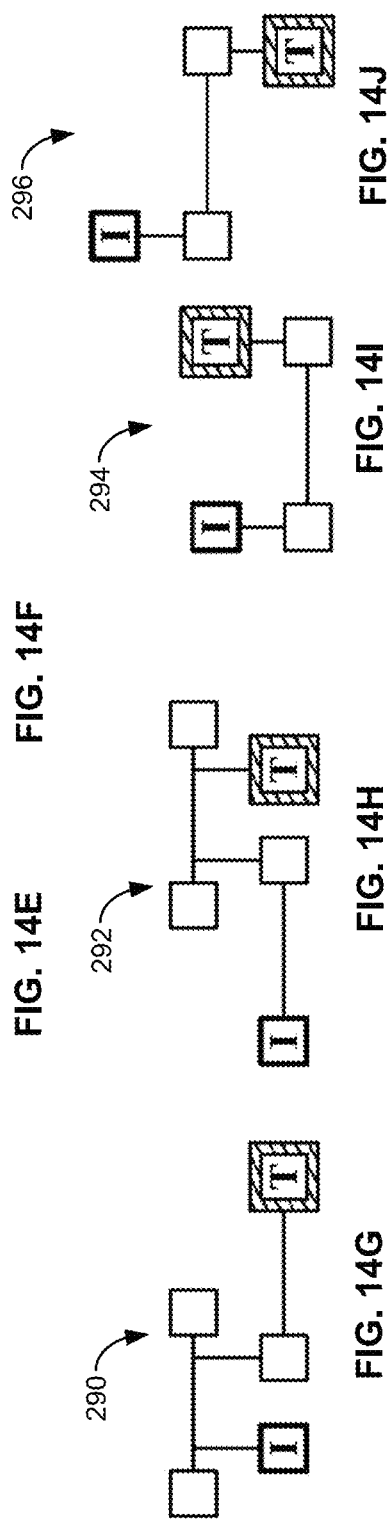

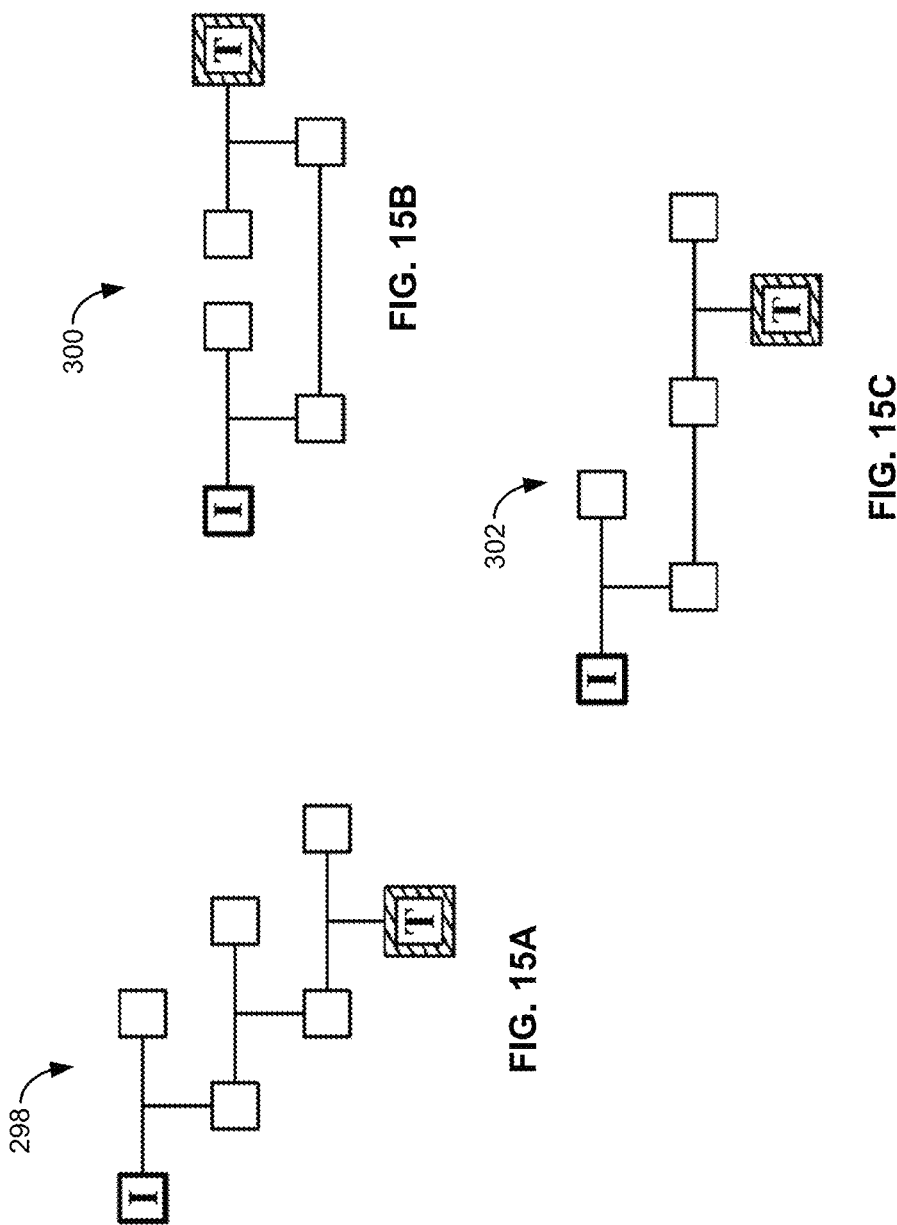

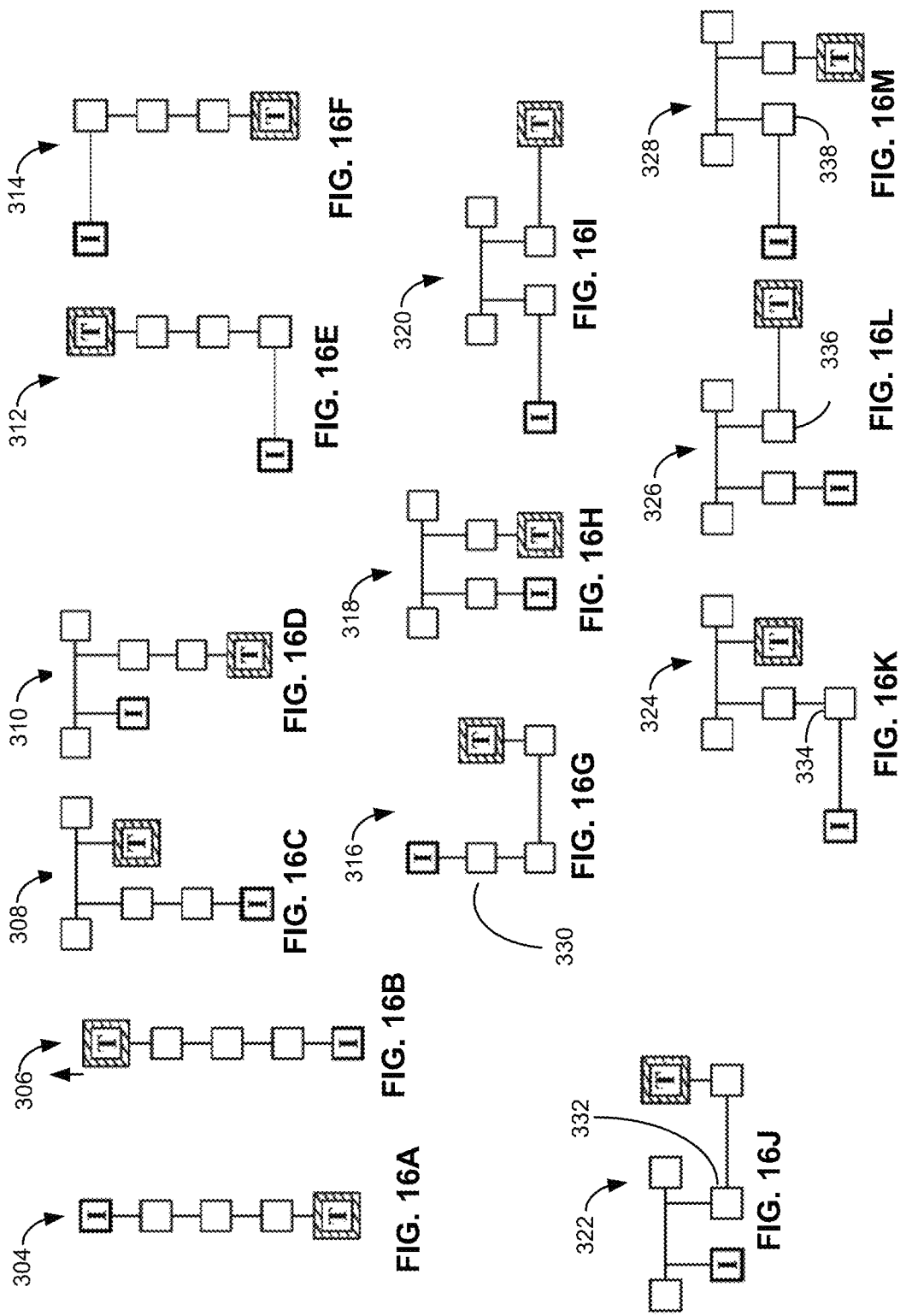

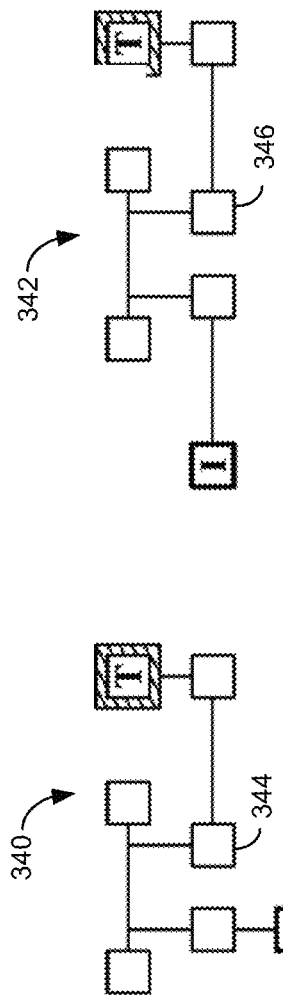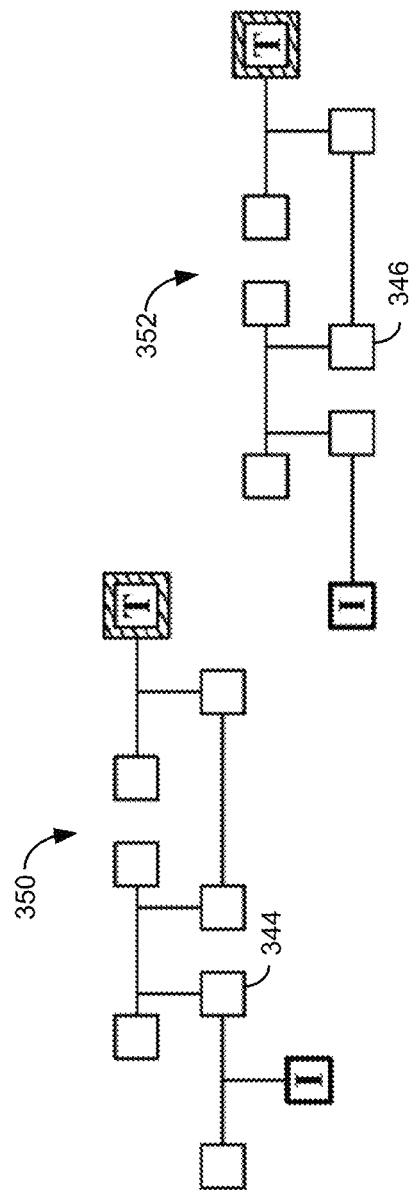
FIG. 17A FIG. 17B FIG. 18A FIG. 18B

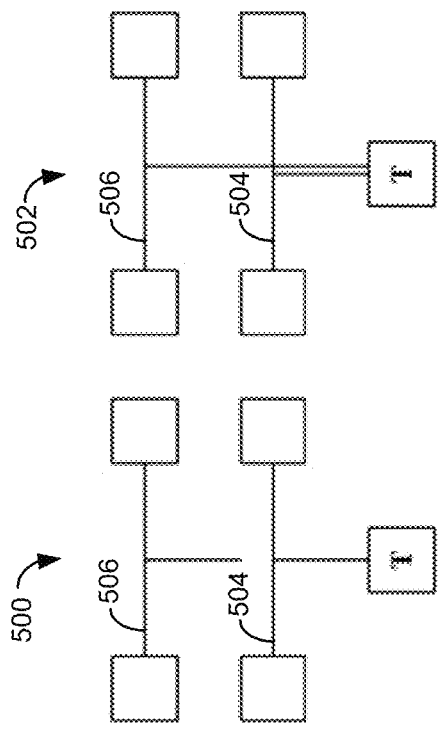
FIG. 29A
FIG. 29B
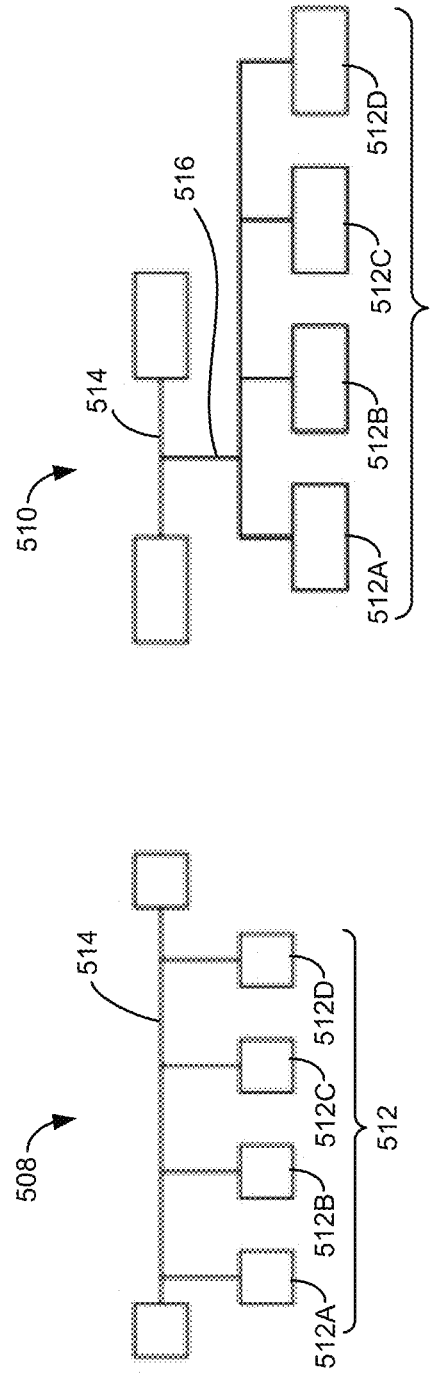
FIG. 30B
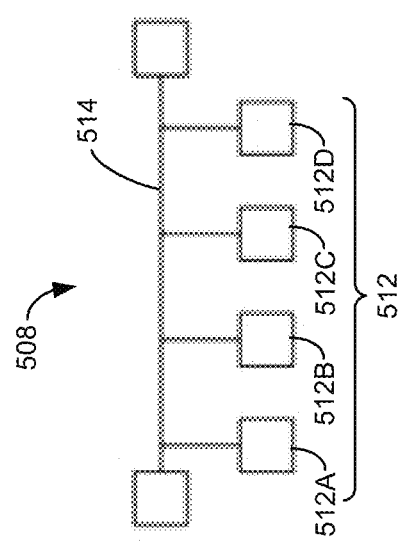
FIG. 30A

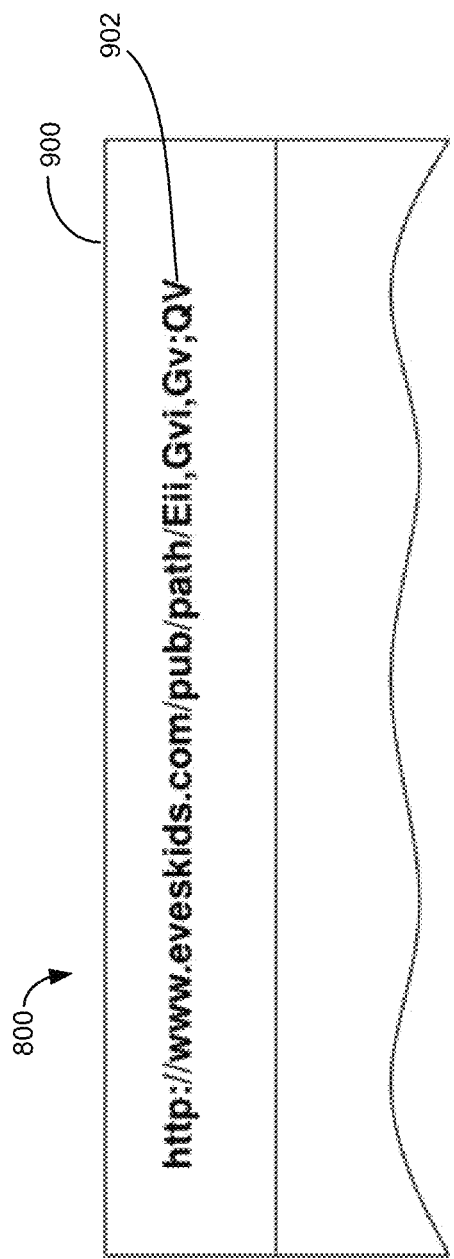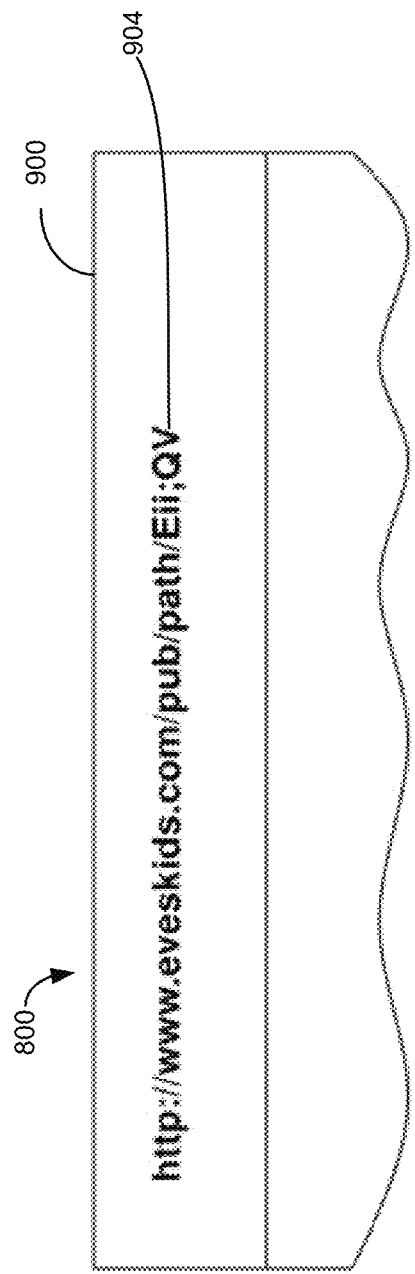
FIG. 36A
FIG. 36B

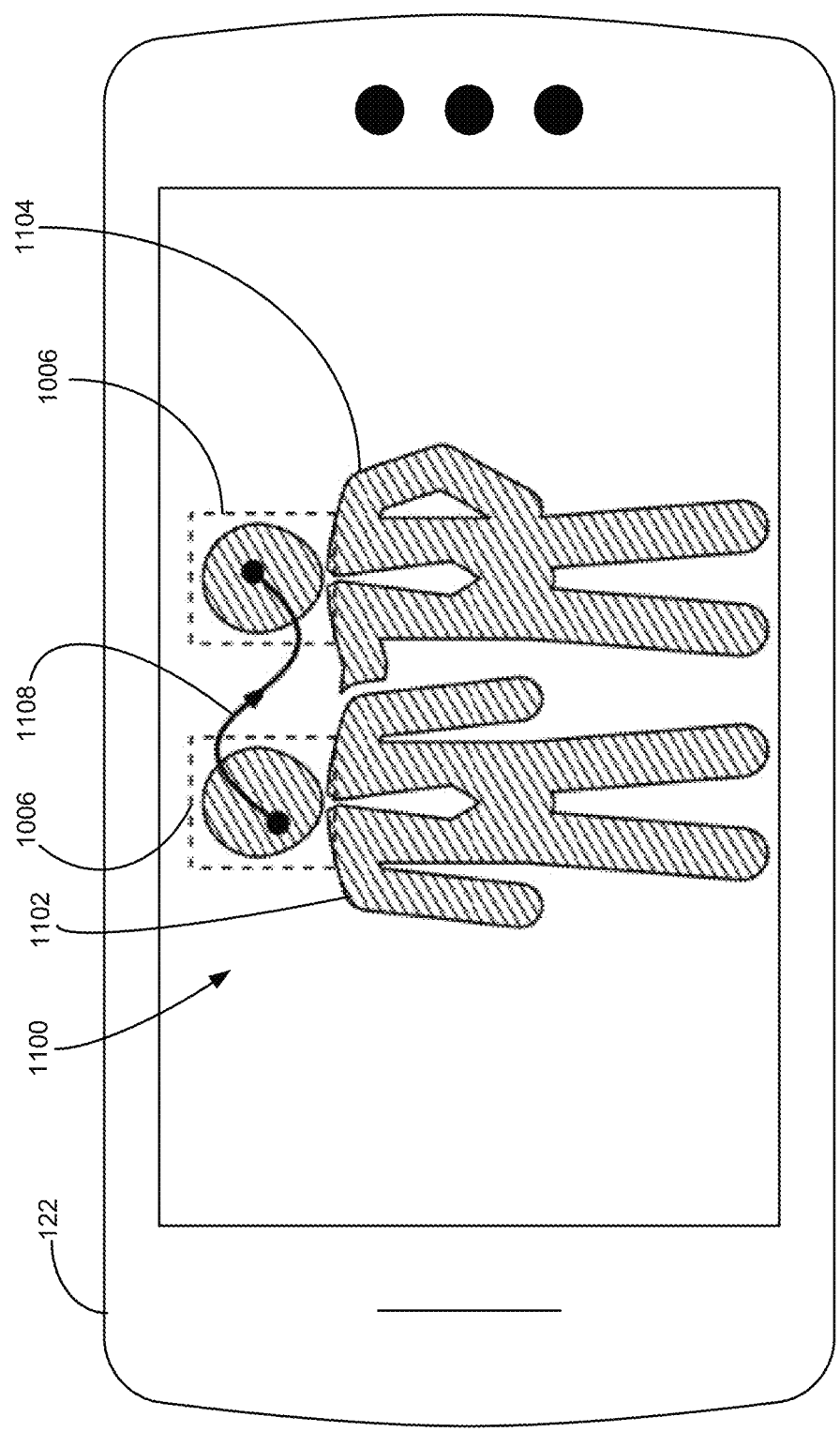

SYSTEMS AND METHODS FOR GENEALOGICAL GRAPHING

FIELD

The embodiments disclosed herein relate to systems and methods of genealogical graphing.

BACKGROUND

Familial relationships can be illustrated in the form of genealogical graphs. When a genealogical graph includes many individuals, the graph can become difficult, and possibly impossible, to navigate. For example, when a viewer or creator of a computer-generated genealogical graph wants to track many generations, the genealogical graph is likely to be very large due to the combinatorial explosion of the ancestors (e.g., with two parents, there are four grandparents, and so on) and combinatorial explosions of the descendants as it is common for a family to have an average of more than one child.

Genealogical graphs are typically used to understand one's genealogical history and, in some cases, connections between specific individuals. In order to determine these connections, users need to navigate through the genealogical graphs and possibly research additional genealogical graphs, which can be a cumbersome and extended process.

SUMMARY

The various embodiments described herein generally relate to methods (and associated systems configured to implement the methods) for automatically generating a genealogical graph for an initial member and a target member.

In accordance with an embodiment, there is provided a computer-implemented method of automatically generating a genealogical graph for an initial member and a target member. The method involves operating a processor to: i) receive an initial member identifier identifying the initial member and a target member identifier identifying the target member; ii) retrieve, from a memory, a set of genealogical data for the initial member and a set of genealogical data for the target member; iii) determine a genealogical connection between the initial member and the target member; and iv) in response to determining the genealogical connection between the initial member and the target member, generate the genealogical graph to illustrate the determined genealogical connection and a subset of genealogical data from the set of genealogical data for the target member, otherwise, generate the genealogical graph to illustrate a subset of genealogical data from the set of genealogical data for the initial member and the subset of genealogical data from the set of genealogical data for the target member.

In some embodiments of the disclosed methods, in response to determining the genealogical connection between the initial member and the target member is that the initial member is the same as the target member involves generating the genealogical graph to illustrate the subset of genealogical data from the set of genealogical data for the target member.

In some embodiments of the disclosed methods, receiving the initial member identifier identifying the initial member and the target member identifier identifying the target member involves receiving, from a computing device, a user input including the initial member identifier and the target member identifier.

In some embodiments of the disclosed methods, receiving the initial member identifier identifying the initial member and the target member identifier identifying the target member involves: i) operating a first computing device associated with a first user to detect a second computing device associated with a second user within a proximity threshold; and ii) in response to detecting the second computing device by the first computing device, operating the processor to assign a first user identifier associated with the first user as the initial member identifier and to assign a second user identifier associated with the second user as the target member identifier.

In some embodiments of the disclosed methods, the proximity threshold includes a physical distance defined by at least one of the first user and the second user.

In some embodiments of the disclosed methods, receiving the initial member identifier identifying the initial member and the target member identifier identifying the target member involves: i) operating a first computing device associated with a first user to identify a second computing device associated with a second user when the first computing device scans a Quick Response (QR) code displayed by the second computing device; and ii) in response to identifying the second computing device, operating the processor to assign a first user identifier associated with the first user as the initial member identifier and to assign a second user identifier associated with the second user as the target member identifier.

In some embodiments of the disclosed methods, receiving the initial member identifier identifying the initial member and the target member identifier identifying the target member involves: i) displaying an image showing one or more members; ii) receiving, from a computing device, a user input selecting a first member and a second member from the one or more members shown on the image; iii) determining a first member identifier corresponding to the selected first member and a second member identifier corresponding to the selected second member; and iv) assigning the first member identifier as the initial member and the second member identifier as the target member identifier.

In some embodiments, the disclosed methods involve: i) receiving a new target identifier identifying a new target member that is different from the target member; ii) retrieving, from the memory, a set of genealogical data for the new target member; iii) determining a genealogical connection between the initial member and the new target member; and iv) generating an updated genealogical graph to illustrate the genealogical connection between the initial member and the new target member, and a subset of genealogical data from the set of genealogical data for the new target member.

In some embodiments of the disclosed methods, receiving the new target identifier involves: i) receiving a user input selecting a node in the genealogical graph, in which the genealogical graph includes a set of nodes representing the determined genealogical connection and the subset of genealogical data for the target member; and ii) assigning a member identifier associated with the selected node as the new target identifier.

In some embodiments of the disclosed methods, the subset of genealogical data from the set of genealogical data for the new target member includes a first degree genealogical data set for the new target member.

In some embodiments of the disclosed methods, generating the genealogical graph involves: i) detecting a display size of a computing device for displaying the genealogical graph; and ii) adjusting the genealogical graph for the detected display size.

In some embodiments of the disclosed methods, adjusting the genealogical graph for the detected display size involves varying at least one of the subset of genealogical data for the target member and the subset of genealogical data for the initial member.

In some embodiments of the disclosed methods, the genealogical graph includes a set of nodes representing the determined genealogical connection and the subset of genealogical data for the target member, and adjusting the genealogical graph for the detected display size involves varying a path connecting the set of nodes.

In some embodiments of the disclosed methods, the subset of genealogical data from the set of genealogical data for the target member includes a first degree genealogical data set for the target member.

In some embodiments of the disclosed methods, the subset of genealogical data from the set of genealogical data for the initial member includes a first degree genealogical data set for the initial member.

In some embodiments of the disclosed methods, generating the genealogical graph involves: i) displaying a target node for the target member; ii) displaying a member node for each member identified in the subset of genealogical data for the target member; and iii) connecting the target node and each member node based on the sets of genealogical data for the target member and the initial member.

In some embodiments, the disclosed methods involve displaying an initial node for the initial member when the initial member and the target member are different, and connecting the initial node with the target node and at least some of the member nodes based on the sets of genealogical data for the target member and the initial member.

In some embodiments of the disclosed methods, retrieving the set of genealogical data for the initial member and the set of genealogical data for the target member involves: i) determining a degree threshold for the genealogical graph, wherein the degree threshold defines a maximum degree of genealogical data to display in the genealogical graph; and ii) for each of the initial member and the target member, retrieving the set of genealogical data associated with members at least one degree more than the degree threshold.

In some embodiments of the disclosed methods, retrieving the set of genealogical data for the initial member and the set of genealogical data for the target member involves: i) receiving a supplementary identifier identifying a supplemental member; and ii) retrieving, from the memory, a set of genealogical data for the supplemental member.

In some embodiments, the disclosed methods involve receiving, via a genealogical degree selection control, a genealogical degree selection defining a genealogical degree of genealogical data to display in the genealogical graph.

In accordance with an embodiment, there is provided a system of automatically generating a genealogical graph for an initial member and a target member. The system includes a memory for storing a set of genealogical data for the initial member and a set of genealogical data for the target member and a processor. The processor is operable to: i) receive, from a computing device, an initial member identifier identifying the initial member and a target member identifier identifying the target member; ii) retrieve, from the memory, a set of genealogical data for the initial member and a set of genealogical data for the target member; iii) determine whether a genealogical connection exists between the initial member and the target member; and iv) in response to determining the genealogical connection exists between the initial member and the target member, generate the genealogical graph to illustrate the determined genealogical connection and a subset of genealogical data from the set of genealogical data for the target member, otherwise, generate the genealogical graph to illustrate a subset of genealogical data from the set of genealogical data for the initial member and the subset of genealogical data from the set of genealogical data for the target member.

In some embodiments of the disclosed systems, the processor is operable to, in response to determining the genealogical connection between the initial member and the target member is that the initial member is the same as the target member, generate the genealogical graph to illustrate the subset of genealogical data from the set of genealogical data for the target member.

In some embodiments of the disclosed systems, the processor is operable to receive from the computing device, a user input including the initial member identifier and the target member identifier.

In some embodiments of the disclosed systems, the processor: i) operates a first computing device associated with a first user to detect a second computing device associated with a second user within a proximity threshold; and ii) assigns, in response to detecting the second computing device by the first computing device, a first user identifier associated with the first user as the initial member identifier and assigns a second user identifier associated with the second user as the target member identifier.

In some embodiments of the disclosed systems, the proximity threshold includes a physical distance defined by at least one of the first user and the second user.

In some embodiments of the disclosed systems, the processor: i) operates a first computing device associated with a first user to identify a second computing device associated with a second user when the first computing device scans a Quick Response (QR) Code displayed by the second computing device; and ii) assigns, in response to identifying the second computing device, a first user identifier associated with the first user as the initial member identifier and assigns a second user identifier associated with the second user as the target member identifier.

In some embodiments of the disclosed systems, the processor operates to: i) display an image showing one or more members; ii) receive, from a computing device, a user input selecting a first member and a second member from the one or more members shown on the image; iii) determine a first member identifier corresponding to the selected first member and a second member identifier corresponding to the selected second member; and iv) assign the first member identifier as the initial member and the second member identifier as the target member identifier.

In some embodiments of the disclosed systems, the processor operates to: i) receive a new target identifier identifying a new target member that is different from the target member; ii) retrieve, from the memory, a set of genealogical data for the new target member; iii) determine a genealogical connection between the initial member and the new target member; and iv) generate an updated genealogical graph to illustrate the genealogical connection between the initial member and the new target member, and a subset of genealogical data from the set of genealogical data for the new target member.

In some embodiments of the disclosed systems, the processor operates to: i) receive a user input selecting a node in the genealogical representation, wherein the genealogical graph includes a set of nodes representing the determined genealogical connection and the subset of genealogical data for the target member; and ii) assign a member identifier associated with the selected node as the new target identifier.

In some embodiments of the disclosed systems, the subset of genealogical data from the set of genealogical data for the new target member includes a first degree genealogical data set for the new target member.

In some embodiments of the disclosed systems, the processor operates to: i) detect a display size of a computing device for displaying the genealogical graph; and ii) adjust the genealogical graph for the detected display size.

In some embodiments of the disclosed systems, the processor operates to vary a subset of genealogical data for the target member and the subset of genealogical data for the initial member.

In some embodiments of the disclosed systems, the genealogical graph includes a set of nodes representing the determined genealogical connection and the subset of genealogical data for the target member, and the processor operates to vary a path connecting the set of nodes to adjust the genealogical graph.

In some embodiments of the disclosed systems, the subset of genealogical data from the set of genealogical data for the target member includes a first degree genealogical data set for the target member.

In some embodiments of the disclosed systems, the subset of genealogical data from the set of genealogical data for the initial member includes a first degree genealogical data set for the initial member.

In some embodiments of the disclosed systems, the processor operates to: i) display a target node for the target member; ii) display a member node for each member identified in the subset of genealogical data for the target member; and iii) connect the target node and each member node based on the sets of genealogical data for the target member and the initial member.

In some embodiments of the disclosed systems, the processor operates to display an initial node for the initial member when the initial member and the target member are different, and to connect the initial node with the target node and at least some of the member nodes based on the sets of genealogical data for the target member and the initial member.

In some embodiments of the disclosed systems, the processor operates to: i) determine a degree threshold for the genealogical graph, wherein the degree threshold defines a maximum degree of genealogical data to display in the genealogical graph; and ii) for each of the initial member and the target member, retrieve the set of genealogical data associated with members at least one degree more than the degree threshold.

In some embodiments of the disclosed systems, the processor operates to: i) receive a supplementary identifier identifying a supplemental member; and ii) retrieve, from the memory, a set of genealogical data for the supplemental member.

In some embodiments of the disclosed systems, the processor operates to receive, via a genealogical degree selection control, a genealogical degree selection defining a genealogical degree of genealogical data to display in the genealogical graph.

BRIEF DESCRIPTION OF THE DRAWINGS

Several embodiments will now be described in detail with reference to the drawings, in which:

FIG. 8A shows an example genealogical graph;

FIG. 8B shows an exploded version of the example genealogical graph shown in FIG. 8A with sequel pointers;

FIG. 10A is an example genealogical graph of a first degree relationship for a small display;

FIG. 10B is another example genealogical graph of a first degree relationship for a small display;

FIG. 10C is another example genealogical graph of a first degree relationship for a small display;

FIG. 11A is an example genealogical graph for a large display corresponding to the example genealogical graph shown in FIG. 10A;

FIG. 11B is an example genealogical graph for a large display corresponding to the example genealogical graph shown in FIG. 10B;

FIG. 12A is an example genealogical graph of a second-degree relationship for a small display;

FIG. 12B is another example genealogical graph of a second-degree relationship for a small display;

FIG. 12C is another example genealogical graph of a second-degree relationship for a small display;

FIG. 12D is another example genealogical graph of a second-degree relationship for a small display;

FIG. 12E is another example genealogical graph of a second-degree relationship for a small display;

FIG. 12F is another example genealogical graph for a second-degree relationship for a small display;

FIG. 12G is another example genealogical graph of a second-degree relationship for a small display;

FIG. 12H is another example genealogical graph of a second-degree relationship for a small display;

FIG. 12I is another example genealogical graph of a second-degree relationship for a small display;

FIG. 12J is another example genealogical graph of a second-degree relationship for a small display;

FIG. 13A is an example genealogical graph for a large display corresponding to the example genealogical graph shown in FIG. 12A;

FIG. 13B is an example genealogical graph for a large display corresponding to the example genealogical graph shown in FIG. 12B;

FIG. 13C is an example genealogical graph for a large display corresponding to the example genealogical graph shown in FIG. 12E;

FIG. 14A is an example genealogical graph of a third-degree relationship for a small display;

FIG. 14B is another example genealogical graph of a third-degree relationship for a small display;

FIG. 14C is another example genealogical graph of a third-degree relationship for a small display;

FIG. 14D is another example genealogical graph of a third-degree relationship for a small display;

FIG. 14E is another example genealogical graph of a third-degree relationship for a small display;

FIG. 14F is another example genealogical graph for a third-degree relationship for a small display;

FIG. 14G is another example genealogical graph of a third-degree relationship for a small display;

FIG. 14H is another example genealogical graph of a third-degree relationship for a small display;

FIG. 14I is another example genealogical graph of a third-degree relationship for a small display;

FIG. 14J is another example genealogical graph of a third-degree relationship for a small display;

FIG. 15A is an example genealogical graph for a large display corresponding to the example genealogical graph shown in FIG. 14A;

FIG. 15B is an example genealogical graph for a large display corresponding to the example genealogical graph shown in FIG. 14I;

FIG. 15C is an example genealogical graph for a large display corresponding to the example genealogical graph shown in FIG. 14J;

FIG. 16A is an example genealogical graph of a fourth-degree relationship for a small display;

FIG. 16B is another example genealogical graph of a fourth-degree relationship for a small display;

FIG. 16C is another example genealogical graph of a fourth-degree relationship for a small display;

FIG. 16D is another example genealogical graph of a fourth-degree relationship for a small display;

FIG. 16E is another example genealogical graph of a fourth-degree relationship for a small display;

FIG. 16F is another example genealogical graph for a fourth-degree relationship for a small display;

FIG. 16G is another example genealogical graph of a fourth-degree relationship;

FIG. 16H is another example genealogical graph of a fourth-degree relationship for a small display;

FIG. 16I is another example genealogical graph of a fourth-degree relationship for a small display;

FIG. 16J is another example genealogical graph of a fourth-degree relationship for a small display;

FIG. 16K is another example genealogical graph of a fourth-degree relationship for a small display;

FIG. 16L is another example genealogical graph of a fourth-degree relationship for a small display;

FIG. 16I is another example genealogical graph of a fourth-degree relationship for a small display;

FIG. 16M is another example genealogical graph of a fourth-degree relationship for a small display;

FIG. 17A is an example genealogical graph of a fifth-degree relationship for a small display;

FIG. 17B is another example genealogical graph of a fifth-degree relationship between the initial member and the target member;

FIG. 18A is an example genealogical graph for a large display corresponding to the example genealogical graph shown in FIG. 17A;

FIG. 18B is an example genealogical graph for a large display corresponding to the example genealogical graph shown in FIG. 17B;

FIG. 29A is an example schematic of a configuration for a genealogical graph, in accordance with an embodiment;

FIG. 29B is another example schematic showing a different configuration for the genealogical graph of FIG. 29A;

FIG. 30A is an example schematic of a configuration for a genealogical graph, in accordance with an embodiment;

FIG. 30B is another example schematic showing a different configuration for the genealogical graph of FIG. 30A;

FIG. 36A shows an example abbreviated address path;

FIG. 36B shows another example abbreviated address path;

FIG. 38A shows an interactive image interface, in accordance with an example embodiment;

Figure 1:
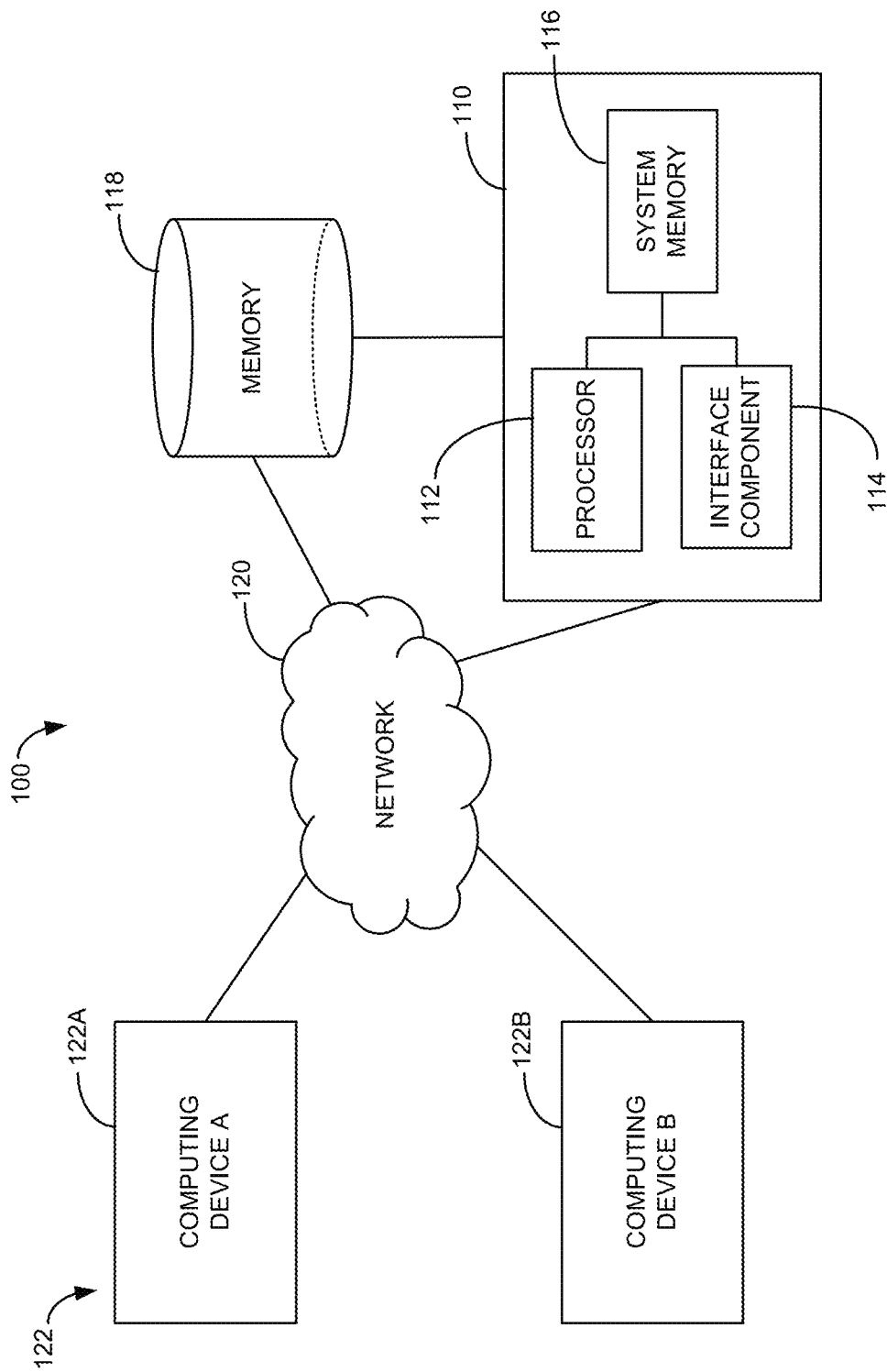
FIG. 1 is a block diagram displaying an example genealogical graphing system.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DETAILED DESCRIPTION OF EXAMPLE EMBODIMENTS

Reference is first made to FIG. 1, which shows a block diagram 100 of components interacting with a genealogical graphing system 110. The genealogical graphing system 110 can include a processor 112, an interface component 114 and a system memory 116.

The genealogical graphing system 110 can interact with a memory 118 directly or via a network 120. The genealogical graphing system 110 can also interact with a computing device 122, such as computing device A 122A and/or computing device B 122B, via the network 120. Although two computing devices 122 are shown, fewer or more computing devices 122 can interact with the genealogical graphing system 110 via the network 120.

In some embodiments, the processor 112, the interface component 114, and the system memory 116 may be combined into fewer components or may be separated into further components. The processor 112, the interface component 114 and the system memory 116 may be implemented in software or hardware, or a combination of software and hardware.

Although only one genealogical graphing system 110 is shown, there may be multiple genealogical graphing systems 110 distributed over a wide geographic area and connected via the network 120.

The processor 112 can control the operation of the genealogical graphing system 110. The processor 112 may be any suitable processors, controllers or digital signal processors that can provide sufficient processing power depending on the configurations, purposes and requirements of the genealogical graphing system 110. In some embodiments, the processor 112 can include more than one processor 112 with each processor 112 being configured to perform different dedicated tasks.

The genealogical graphing system 110 can store the information in the memory 118. Storage can also correspond with the secondary storage within the computing device 122. Generally, the secondary storage may be any suitable storage device such as a hard disk drive, a solid state drive, a memory card, or a disk (e.g. CD, DVD, or Blu-ray etc.). Also, the memory 118 can be locally connected with the genealogical graphing system 110. In some cases, the memory 118 may be located remotely from the genealogical graphing system 110 and accessible to the genealogical graphing system 110 via the network 120. In some cases, the memory 118 can include one or more storage devices located at a networked cloud storage provider.

The interface component 114 may be any interface that can enable the genealogical graphing system 110 to communicate with other devices and systems. In some embodiments, the interface component 114 can include at least one of a serial port, a parallel port or a USB port. The interface component 114 may also include at least one of an Internet, Local Area Network (LAN), Ethernet, Firewire, modem or digital subscriber line connection. Various combinations of these elements may be incorporated within the interface component 114.

In some embodiments, the interface component 114 may be a network communication interface. In embodiments in which elements are combined, the interface component 114 may be a software communication interface, such as those for inter-process communication (IPC). In still other embodiments, there may be a combination of interface components 114 implemented as hardware, software, and combination thereof.

For example, the interface component 114 may receive input through the use of various input devices, such as a mouse, a keyboard, a touch-screen, a thumbwheel, a camera, a track-pad, a track-ball, a card-reader, voice recognition software and the like depending on the requirements and implementation of the genealogical graphing system 110.

The system memory 116 can include RAM, ROM, one or more hard drives, one or more flash drives or some other suitable data storage elements such as disk drives, etc. For instance, the operating system provides various basic operational processes for the processor 112. The programs include various user programs so that a user can interact with the processor 112 to perform various functions such as, but not limited to, viewing and manipulating data.

The computing device 122 may be any networked device operable to connect to the network 120. A networked device is a device capable of communicating with other devices through a network such as the network 120. The networked device may couple to the network 120 through a wired or wireless connection.

The computing device 122 may include at least a processor and memory, and may be an electronic tablet device, a personal computer, a workstation, a server, a portable computer, a mobile device, a personal digital assistant, a laptop, a smart phone, a WAP phone, an interactive television, a video display terminal, a gaming console, and a portable electronic device or any combination of these.

The computing device 122 may include an input device for entering information and making requests. For example, the input device may be a keyboard, a keypad, a cursor-control device, a touch-screen, a camera, a microphone, or any combination of these. The computing device 122 may further include a display device having a display screen for presenting visual information. For example, the display device may be a computer monitor, a flat-screen display, a projector, a display panel or any combination of these.

The network 120 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between, the genealogical graphing system 110, the memory 118, and the computing device 122.

In addition, although aspects of an implementation of the genealogical graphing system 110 may be described as being stored in the memory 118, one skilled in the art will appreciate that these aspects can also be stored on or read from other types of computer program products or computer-readable media, such as a secondary storage device, such as hard disks, floppy disks, CDs, or DVDs; a carrier wave from the Internet or other network; or other forms of RAM or ROM.

Referring still to FIG. 1, the computing device 122 can send information to the genealogical graphing system 110. For example, a user associated with the computing device 122 may manipulate one or more of the input devices associated with the computing device 122 to interact with the genealogical graphing system 110. Generally, the computing device 122 can communicate with the genealogical graphing system 110 via the network 120 (e.g. in the form of a web browser). Alternatively, or in addition, a computer application can be stored locally at the computing device 122 that can communicate with the genealogical graphing system 110 via the network 120.

The genealogical graphing system 110 can be configured to receive a plurality of information and requests from a plurality of computing devices 122. Generally, the information can comprise at least an identifier identifying the user. For example, the information can comprise one or more of a username, an e-mail address, a password, or a social media handle.

The computing device 122 can be associated with a user account. For example, the computing device 122 may be associated with the user account by sending credentials (e.g. a cookie, a login, or a password, etc.) to the genealogical graphing system 110. The genealogical graphing system 110 may verify the credentials (e.g. determine that the received password matches a password associated with the user account). If the computing device 122 is associated with the user account, the genealogical graphing system 110 may consider further acts by the computing device 122 to be associated with that user account.

Well-known royal families are used in the examples described herein. Short forms may be used in place of full names to limit the size and improve clarity of the figures. For ease of reference, Table 1 provides a list of short forms that correspond to an adjacent list of royal names. For example, the short form Eii can be associated to Queen Elizabeth II.

TABLE 1

Name Correspondence Table for Royal Family Members

| Short form | Royal Name | Short form | Royal Name |
|---|---|---|---|
| Eii | Queen Elizabeth II | DPW | Diana |
| PPDE | Prince Philip | CDC | Camilla Parker-Bowles |
| CPW | Prince Charles | PW | Prince William |
| QEQM | QE the Queen Mother | PH | Prince Harry |
| Gvi | King George VI | SDY | Sarah |
| APR | Princess Anne | PBY | Princess Beatrice |
| PADY | Prince Andrew | PEY | Princess Eugenie |
| PEEW | Prince Edward | SCW | Sophie |
| Gv | King George V | ME | Mary Elphinstone |
| MT | Queen Mary | PBL | Patrick Bowes-Lyon |
| ESK | Claude Bowes-Lyon | JBL | John Bowes-Lyon |
| CSK | Cecilia Bowes-Lyon | FBL | Fergus Bowes-Lyon |
| MP | Mark Philips | RLG | Rose Leveson-Gower |
| TL | Timothy Laurence | DBL | David Bowes-Lyon |
| PPh | Peter Philips | AAJ | Antony Armstrong-Jones |
| ZT | Zara Tindall | DAJ | David Armstrong-Jones |
| PMCS | Princess Margaret | PMGD | Princess Margarita |
| PAGD | Prince Andrew | PSGD | Princess Sophie |
| PAB | Princess Alice | VPR | Victoria, Princess Royal |
| QV | Queen Victoria | WiGE | William I, German Emperor |

TABLE 1-continued

Name Correspondence Table for Royal Family Members

| Short form | Royal Name | Short form | Royal Name |
|---|---|---|---|
| ASCG | Albert of Saxe-Coburg and Gotha | FiiiGE | Frederick III, German Emperor |
| Evii | Edward VII | PLP | Princess Louise of Prussia |
| AD | Alexandra of Denmark | FiGDB | Frederick I, Grand Duke of Baden |
| CixD | Christian IX of Denmark | LiGDB | Leopold I, Grand Duke of Baden |
| LHK | Louise of Hesse-Kassel | PSS | Princess Sophie of Sweden |
| DFW | Duke Friedrich Wilhelm | GDOF | Grand Duchess Olga Feodorovna of Russia |
| PLCHK | Princess Louise Caroline of Hesse-Kassel | GDMN | Grand D Michael Nikolaevich of Russia |
| PCHK | Princess Charles of Hesse-Kassel | NiR | Nicholas I of Russia |
| PLD | Princes Louise of Denmark | AF | Alexandra Feodorovna (Charlotte of Prussia) |
| FiiLHK | Frederick II. Landgrave Hesse-Kassel | GiG | George I of Greece |
| PMGB | Princess Mary of Great Britain | OCR | Olga Constantinovna of Russia |
| GiiGB | George II of Great Britain | CiG | Constantine I of Greece |
| CA | Caroline of Ansbach | PGWH | Prince George William of Hanover |

Figure 2:
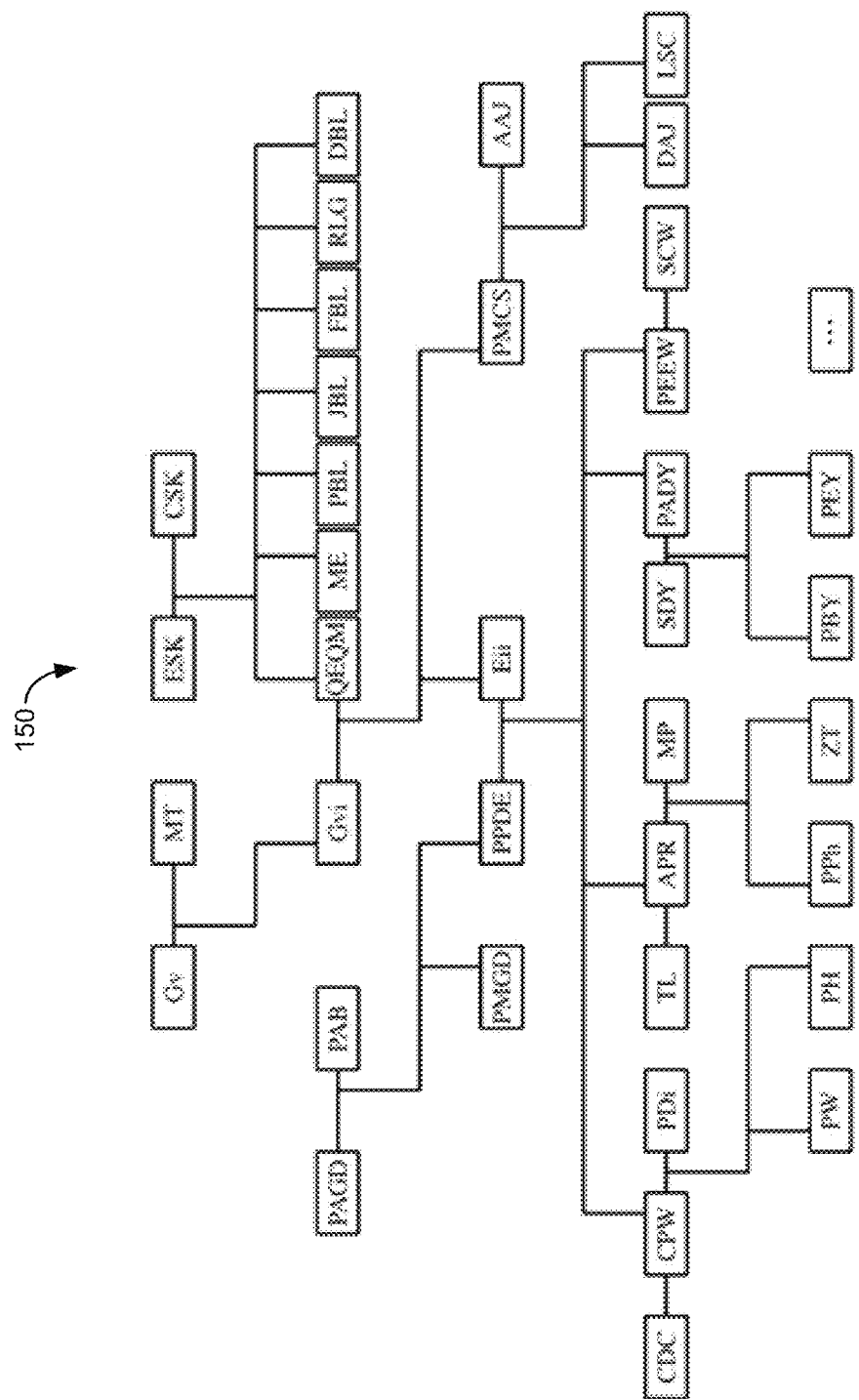
FIG. 2 is an example genealogical graph in accordance with an example embodiment.

Existing genealogical graphs are often large, complicated, and hard to understand. It is common for a genealogical graph to display all members associated with one or more main members. For example, FIG. 2 shows an example genealogical graph 150 for Queen Elizabeth II (Eii) as a main member.

However, displaying all members on the single genealogical graph may not, in general, succeed in simultaneously satisfying all desirable visual aspects. For example, it can be a useful attribute of a genealogical graph for generations to appear on the same horizontal level. The desirable visual aspects can include reasonable edge length, consistent generational spacing, and planarity. In the example shown in FIG. 2, the conventional genealogical graph 150 may sacrifice reasonable edge length in order to maintain planarity and consistent generational spacing. Without reasonable edge length, the user may be forced to track long distances to determine relationships on the conventional genealogical graph 150.

Similarly, another desirable visual aspect of genealogical graphs is for children of the same parents to appear nearby in the genealogical graph. This also is a constraint that cannot be generally satisfied if the user is to display many descendants of each of these children. In such a case, edge length can no longer have an upper bound and the observer of the genealogical graph is forced to track long edges.

Figure 3A:
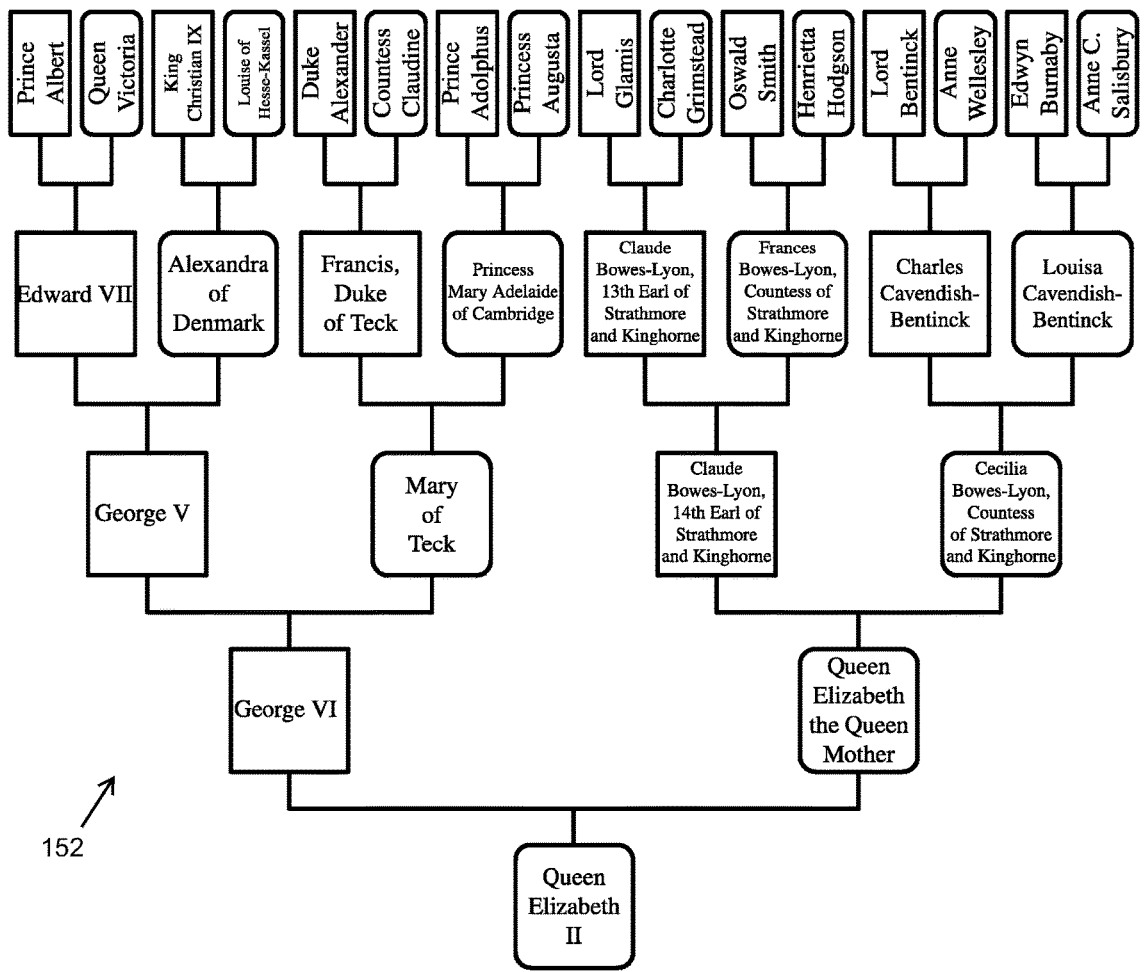
FIG. 3A is an example genealogical graph for Queen Elizabeth in accordance with an example embodiment.
Figure 3B:
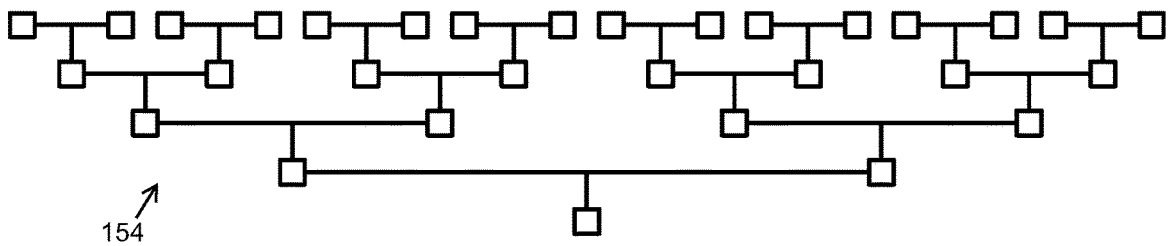
FIG. 3B shows another configuration for the example genealogical graph of Queen Elizabeth II shown in FIG. 3A.
Figure 3C:
FIG. 3C shows another configuration for the genealogical graph of Queen Elizabeth II shown in FIG. 3A.

Due to the size and complexity of the genealogical graph 150, it can be advantageous to prune the genealogical graph 150 to focus on one aspect. Genealogists would traditionally prune all but the ancestors of one individual to generate a genealogical graph for the ancestors of that individual. Genealogists would traditionally also prune all but the descendants to generate a genealogical graph for the descendants of that individual. FIGS. 3A to 3C show example genealogical graphs 152, 154, 156 for ancestors of Queen Elizabeth II.

Referring still to FIGS. 3A to 3C, the genealogical graphs 152, 154 and 156, display several generations of Queen Elizabeth's ancestors. With each additional generation displayed in the genealogical graph, less detail can be displayed depending on the size and resolution restrictions of a display screen of the display device. For example, the genealogical graph 152 and the genealogical graph 154 display the same number of generations of Queen Elizabeth's ancestors; however, the genealogical graph 154 is displayed on a smaller display screen which can significantly limit the amount of information that can be displayed. The genealogical graph 156 displays one more generation of Queen Elizabeth's ancestors than the genealogical graph 154. Consequently, even less detail can be displayed on the genealogical graph 156 in comparison to the genealogical graph 154.

In some embodiments, the genealogical graph can be structured as a mathematical graph. For example, each member in the genealogical graph can be associated with a node, and the connections between the members can be edges. An edge between a parent and a child can be a vertical segment, and an edge between spouses can be a horizontal segment.

A genealogical graph can be referred to as planar if all edges intersect at nodes. Planarity is a canonical characteristic of mathematical graphs. A necessary and sufficient condition for the mathematical graph to be planar is established by the absence of Kuratowski subgraphs ($K_5$ and $K_{3,3}$). Any sufficiently large genealogical graph can include either of these subgraphs, which means that the genealogical graph will be non-planar. Losing planarity can sacrifice a desirable visual aspect of the genealogical graph.

The following description can provide a solution to displaying genealogical graphs: edges can be similar in length (and ultimately proportional to the number of children) of any one parent, generations can appear strictly on the same generational level, and planarity can be guaranteed. To achieve this, producing a single, static genealogical graph may be sacrificed. The genealogical graphs that can be produced can be fully interactive. The genealogical graphs can be observed and manipulated to investigate a selected member's ancestors and descendants, as well as extended relatives, such as in-laws, in-laws of in-laws, etc.

The genealogical graphing system 110 can generate genealogical graphs based on the preferences and/or needs of the users. For example, the genealogical graphing system 110 can generate a simple genealogical graph illustrating only a connection between two members. In another example, the genealogical graphing system 110 can generate genealogical graphs in which spousal relationships are shown west to east or, alternatively, east to west depending on the user preferences and/or settings of the computer (e.g., for a right-to-left language). By generating genealogical graphs in which the spousal relationships are west to east, or east to west, the genealogical graphing system 110 can, to an extent, avoid generating a non-planar genealogical graph. As mentioned above, the certainty of the presence of the Kuratowski subgraphs ($K_5$ and $K_{3,3}$) in any non-trivial genealogical graph can mean that it is impossible to display a planar genealogical graph.

In a further example, the genealogical graphing system 110 can generate a genealogical graph that can be navigated by a user, and based on the user navigation and/or other inputs from the user, the genealogical graphing system 110 can update the genealogical graph to include additional members to the genealogical graph. For example, the genealogical graphing system 110 can generate a genealogical graph in which the user can navigate to another member on a path between an initial member and a target member, and further beyond the path by selecting a succeeding member of the target member. When the member is selected, the genealogical graphing system 110 can then generate another genealogical graph in which the selected member is the target member and/or insert additional members to the genealogical graph.

The genealogical graphing system 110, in response to an input received from a user, can send a copy of the genealogical graph to a family member. Before sending the information, the genealogical graphing system 110 can show the list of members and the relationships that are being sent. The genealogical graphing system 110 allows the user to select whether to send a full set or a subset of the information. The genealogical graphing system 110 can require the user to confirm that they are aware there is no way to undo the action of sending the genealogical graph.

The memory 118 and/or the system memory 116 can store databases, such as a public database and a private database. The public database can include data related to historical figures, notably monarchs, royal houses, rulers, and their families, while the private database can include personal genealogical data received from a user. The data stored in the private database may be accessible only by the respective user.

When the user is using the private database or public database, the genealogical graphing system 110 can display a mode change icon. For example, the mode change icon can be the shape of a pencil. The mode change icon may act as a toggle for changing between a read-only and a change-enabled mode of the genealogical graphing system 110. In the read-only mode, the user is unable to apply edits and can only view the displayed genealogical graph. When in the public database, the user can toggle to the change-enabled mode; however, none of the edits that are entered by the user can be immediately registered. The changes can instead be shown behind a curfew wall to a specific number of users who are qualified to approve changes. If a preset number of qualified users vote that the information entered is accurate and in the public domain, the genealogical graphing system 110 can register that information to the public database.

Figure 4:
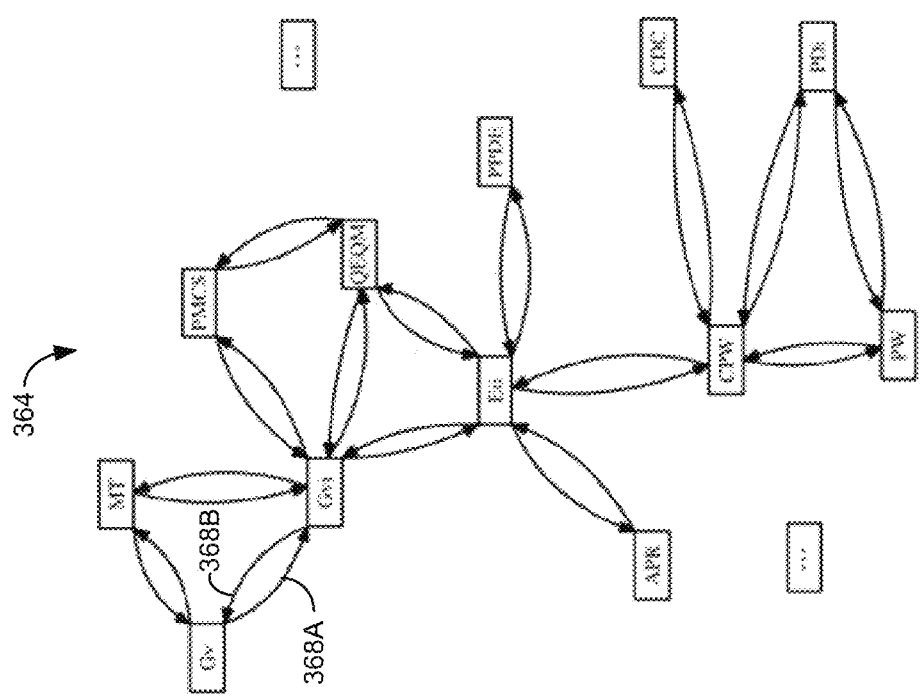
FIG. 4 is an example schematic illustrating the genealogical connections among the relatives of Queen Elizabeth II.
Figure 5A:
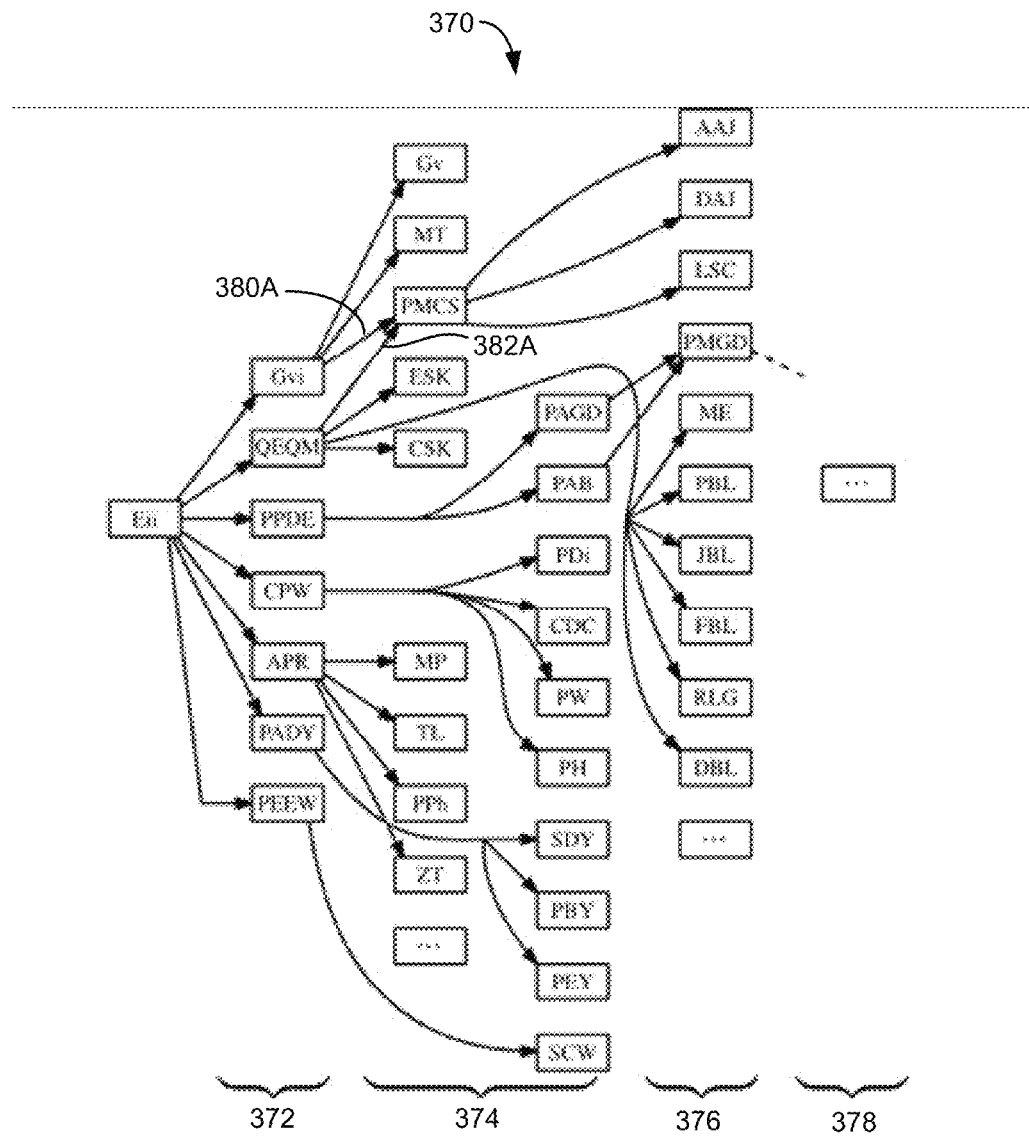
FIG. 5A is an example schematic displaying a breadth-first traversal of some of the genealogical relationships of Queen Elizabeth II.
Figure 5B:
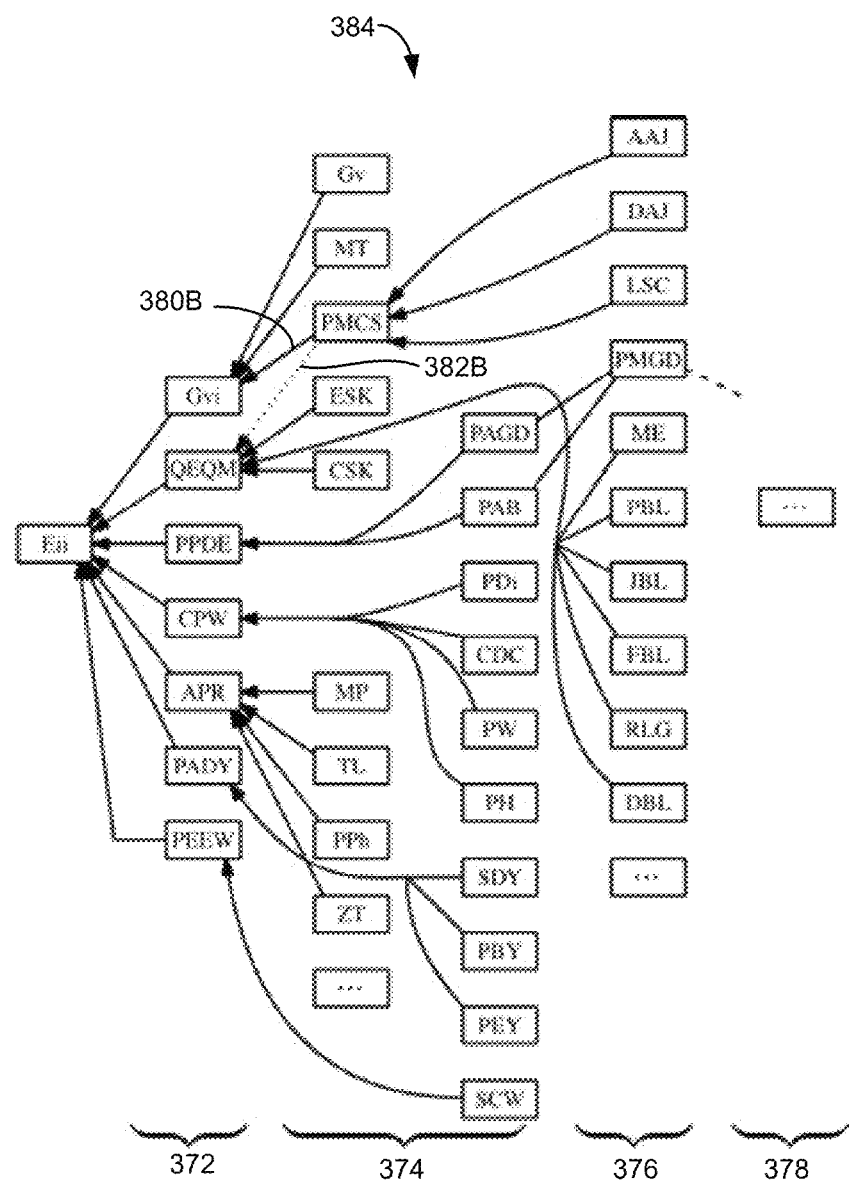
FIG. 5B is an example schematic displaying first preceding node connections corresponding to the example schematic shown in FIG. 5A.

Reference will now be made to FIGS. 4 to 5B, which are example schematics displaying some genealogical relationships of Queen Elizabeth II. The schematics in FIGS. 4 to 5B can illustrate some of the ways in which the genealogical graphing system 110 can generate genealogical graphs with geometries, such as edge length, consistent generational spacing, and planarity, suitable for the corresponding display screen of the display device.

Referring now to FIG. 4, illustrated therein is an example schematic 364 illustrating the genealogical connections among the relatives of Queen Elizabeth II. Each member included in the schematic 364 can be represented by a node. Each relationship, whether it is a parent-, child-, or spouse-relationship, can be represented by an edge. The schematic 364 shows that the genealogical graphing system 110 can draw edges 368 in pairs. For example, King George V is a node Gv and King George VI is a node Gvi. An edge 368A and an edge 368B represent child- and parent-relationships, respectively, between the node Gv and the node Gvi. Although for a given genealogical graph only one line segment (i.e. edge) is drawn to represent a relationship between two nodes, the genealogical graphing system 110 can internally represent such relationships as edge pairs.

Referring specifically to FIG. 5A, illustrated therein is a succeeding member schematic 370 in which Queen Elizabeth II is an initial member Eii. The succeeding member schematic 370 shows a breadth-first traversal of genealogical relationships from the initial member Eii. As shown, the parents (Gvi, QEQM), spouse (PPDE), and four children (CPW, APR, PADY, PEEW) of Eii represent a set of first-degree succeeding members 372. The parents of the set of first-degree succeeding members 372, spouses of the set of first-degree succeeding members 372, and children of the set of first-degree succeeding members 372, excluding the initial member Eii, represent a set of second-degree succeeding members 374. The same practice can be followed for a set of third-degree succeeding members 376, a set of fourth-degree succeeding members 378, and so on. Each member included in the schematic 370 can be represented by a node. The relationship between two nodes, whether it is a parent-, child-, or spouse-relationship, can be represented by an edge. For example, King George VI is a node Gvi, Queen Elizabeth the Queen Mother is a node QEQM, and Princess Margaret is a node PMCS. An edge 380A represents the parent-child relationship between the node Gvi and the node PMCS. Similarly, an edge 382A represents the parent-child relationship between the node QEQM and the node PMCS.

Referring specifically to FIG. 5B, illustrated therein is a preceding member schematic 384 that shows preceding member assignments by reversing the direction of the edges in the succeeding member schematic 370 of FIG. 5A. If a node (i.e. a member) already has a preceding node assigned, any subsequent preceding node assignment can be ignored. This means that a sibling who shares both parents with a second preceding node will have only one of the parents as the first preceding node. Which parent is chosen is immaterial. For example, the node PMCS may have either the node Gvi or the node QEQM as a preceding node since both Gvi and QEQM are parents of PMCS. An edge 380B shows the preceding node relationship between PMCS and Gvi that has been assigned. A dashed edge 382B shows the preceding node relationship between the node PMCS and the node QEQM that has been omitted. In this way, the relationship between any member on the schematic 384 and Queen Elizabeth II can now be read from the labels on the edges which lead back to initial member Eii. This will be discussed in greater detail below with reference to FIG. 8.

Figure 6:
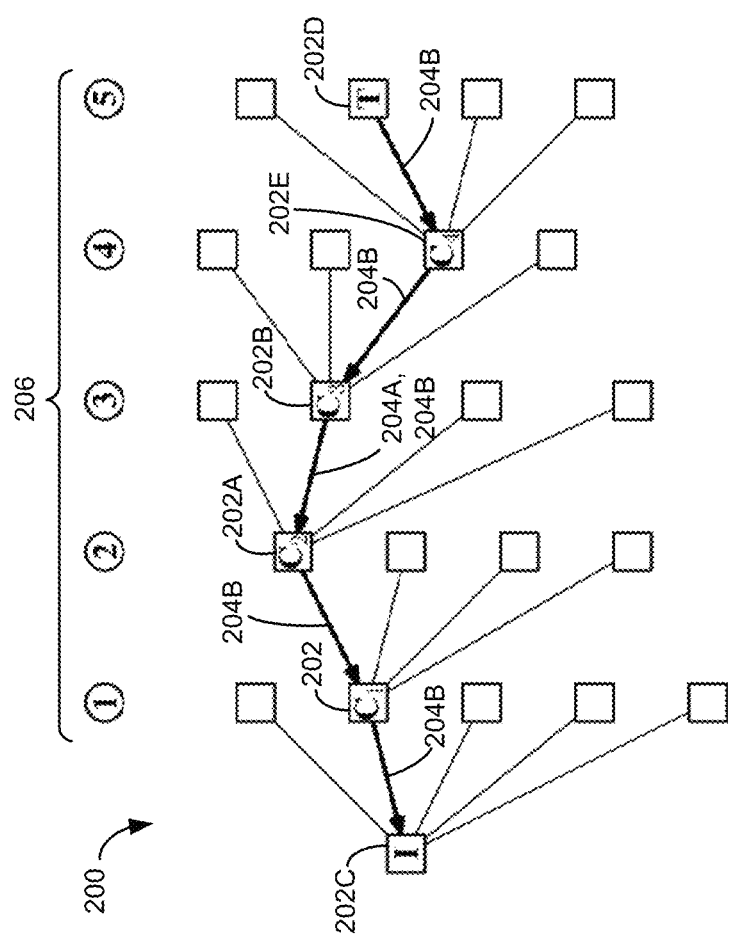
FIG. 6 is an example genealogical data set including a set of nodes and edges.

Referring now to FIG. 6, which illustrates an example genealogical data set 200 including a set of nodes and edges. In the genealogical data set 200, each member can be represented as a node and a connection between two nodes can be represented by an edge. For example, the connection between node 202A and node 202B can be represented by edge 204A. The member selected by the user for study can be termed an initial member (I), which can be represented by an initial node 202C. The genealogical graphing system 110 can assign the initial member as the user logged in and requesting the generation of the genealogical graphs. Since the genealogical graphing system 110 can be used by users to discover relatives through traversal of their genealogical graph, the initial member may often appropriately be referred to as "self". In the genealogical data set 200 nodes arranged along an x-axis based on their relational degree from an initial member (I). That is, nodes (i.e. members) that are the same relational degree from the initial member (I) have the same x-value.

The genealogical graphing system 110 can also receive an input from the user assigning another member as the initial member. For example, when the user is investigating public figures, the genealogical graphing system 110 can assign the public figure being investigated as the initial member.

In some embodiments, the genealogical graphing system 110 can receive an identification of a second member from the user. In response to receiving the identification of the second member, the genealogical graphing system 110 can generate a path from the initial member to the second member (also referred to as a target member T, and can be represented by a target node 202D). The target member can be the member who is being investigated by the user.

An interior node can be a node within the path from the target node 202D to the initial node 202C. For example, an interior node 202E can be a node on the path from the target node 202D to the initial node 202C.

As shown in FIG. 6, a sequence of edge connections 204B can lead from the target node 202D back to the initial node 202C. The sequence of edge connections 204B may be based on the breadth-first traversal of genealogical relationships from the initial node (see e.g., FIG. 5A) and its associated reversal (see e.g., FIG. 5B) which are used to determine the first preceding node assignments for each node on a given path from the target node 202D to the initial node 202C. The number of edge connections 204B between the initial node 202C and the target node 202D can identify a relational degree 206 between the initial member and the target member. In some cases, the target node 202D may be the initial node 202C. For example, if the initial member coincides with the target member, the relational degree is zero.

Data related to individuals who can be included in a genealogical graph can be stored in the memory 118. For each individual, the associated data can be characterized by different node formats, such as an enriched node format, an interior node format, and a target node format. The interior node format can be adjusted, in some embodiments.

In some embodiments, a genealogical graph can include one or more nodes with an enriched node format, and one or more sets of nodes in an interior node format. A typical genealogical graph can include only one target node and therefore, the genealogical graph can include only one node in the target node format.

Each node format can include drawing instructions to trigger the genealogical graphing system 110 to generate the genealogical graph. The drawing instructions can, in some embodiments, be generated by the processor 112. The drawing instructions can be various formats, such as Extensible Markup Language (XML) or JavaScript Object Notation (JSON), for example. The drawing instructions can be associated with a sequential order. Furthermore, the drawing instructions can include relative drawing instructions. For example, the drawing instructions can include: "i. start drawing, ii. draw a line segment of length 50 units to the west, iii. stop drawing, iv. start drawing a line segment 25 units to the north." The genealogical graphing system 110 can reference previously drawn positions while drawing subsequent segments. This can facilitate drawing on programming language that does not have relative drawing instructions built-in.

In some embodiments, the drawing instructions can be recursive drawing instructions. The recursive drawing instructions for drawing a genealogical graph can begin by triggering the genealogical graphing system 110 to draw the target node, then proceeding to generate a line to connect the target node to a first preceding node. A subsequent recursive instruction can trigger the genealogical graphing system 110 to draw the first preceding node. The recursive drawing instructions can end when the genealogical graphing system 110 draws the initial node for the genealogical graph. The term "first preceding node" is used throughout the description to refer to the node along the path of the genealogical graph from the initial node to the target node that immediately precedes the node currently being drawn (i.e. is one degree closer to the initial node). In this way, when the target node and the initial node correspond to the same individual, the genealogical graphing system 110 generates no recursive drawing instructions since there is no first preceding node.

In this example embodiment where the initial node and target node coincide (i.e. initial member and target member are the same individual), the genealogical graphing system 110 can retrieve an image from the enriched node format for the target member. The genealogical graphing system 110 can then add nodes for the parents of the target member by adding a connection northward of the target node, add nodes for the spouse (or spouses) of the target member eastward of the target node, and add nodes for the child (or children) southward of the marriage line connecting the target member to the spouse.

The embodiments described herein can also be implemented using an alternative method. For example, a recursive program running on the genealogical graphing system 110 can generate a drawing program, itself also recursive, for drawing nodes in the interior node format (or adjusted interior node format) and/or the target node format. This can enable a genealogical graphing system 110 of particularly modest processing capability to draw a genealogical graph at optimal speeds. In this way, it can be possible to produce a highly interactive genealogical graphing system 110 even when the memory and processing capabilities of the genealogical graphing system 110 are minimal.

To illustrate the different node formats, reference is now made to FIGS. 7A to 7D, which show an example of the enriched node format, the interior node format, the adjusted interior node format and the target node format, respectively.

Figure 7A:
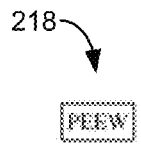
FIG. 7A shows an example enriched node format.

FIG. 7A shows an example enriched node format 218 for an individual with the short form "PEEW". For each individual, the enriched node format can include various data that is stored in the memory 118, such as an image of the individual (e.g., photograph, caricature, or other graphical representation of the individual) and identifying attribute data, such as the sex of the individual, the name of the individual, date of birth, date of death, etc. The name of the individual can be stored in various formats, such as a format having Latin characters and another format in another alphabet.

The enriched node format 218 can also include topological data related to a genealogical graph that can be generated by the genealogical display system 110 for the associated individual. For example, the enriched node format 218 can include an ordered list of individuals within a path to be displayed, at least one identifier corresponding to a first preceding node, and, if the individual has succeeding nodes, at least one identifier corresponding to each of its succeeding nodes.

A genealogical graph can include one or more nodes associated with the enriched node format. For example, the genealogical graphing system 110 can generate a genealogical graph in which a node for a succeeding member of a target member is in the enriched node format, and a node for an initial member can also be in the enriched node format. When a node in the enriched node format is selected, the genealogical graphing system 110 can be triggered to generate a genealogical graph with that selected node as the target node, or at least update the displayed genealogical graph to include genealogical data associated with that selected node. With the enriched node format, the genealogical graphing system 110 can generate the genealogical graph with that selected node as the target node with minimal delay as the related data is stored in the enriched node format. In some embodiments, the genealogical graph can be generated without requiring further data from the genealogical graphing system 110 since the related data is stored in the enriched node format.

The interior node format can be generated by the genealogical graphing system 110 for an interior node representing an individual that forms part of the path between the target node and the initial node of a genealogical graph. That is, nodes associated with the interior node format can act as the interior nodes in the path from the target node to the initial node. In the case when the target node and the initial node coincide (i.e. are the same individual), the genealogical graph will contain no nodes in the interior node format since there are no interior nodes.

Figure 7B:
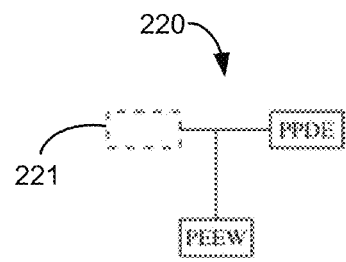
FIG. 7B shows an example interior node format.

FIG. 7B shows an example interior node format 220 for the individual "PEEW" for the case when a first preceding node of PEEW is a parent. The parent is shown as a dashed box 121. The dashed box 121 is not drawn as part of PEEW's interior node format. The dashed box 121 is a placeholder to indicate the place where the parent will be drawn in a subsequent step.

The genealogical graphing system 110 can generate the interior node format in various ways depending on whether the first preceding node of the interior node is a spouse first preceding node, a child first preceding node, or a parent first preceding node. In some embodiments, the genealogical graphing system 110 can generate the interior node in the enriched node format 218 first before proceeding with generating the interior node format 220 for the interior node.

To generate the interior node format when the first preceding node is the spouse first preceding node, the genealogical graphing system 110 can draw the interior node and generate a westward horizontal marriage line from the interior node. The spouse first preceding node can be drawn into the genealogical graph by the genealogical graphing system 110 during a subsequent recursive instruction. If a second preceding node (i.e. a first preceding node of the first preceding node) is a parent of the spouse (i.e. an in-law), the marriage line can be extended to accommodate for the presence of two sets of parent (i.e. the parents of the interior node and the parents of the spouse first preceding node).

To generate the interior node format when the first preceding node is the child first preceding node, the genealogical graphing system 110 can draw the interior node and determine the other parent of the child from the memory 118. The genealogical graphing system 110 can then generate a horizontal marriage line west from the interior node and then draw the node for that other parent. Subsequently, the genealogical graphing system 110 can generate a vertical line, extending south from the horizontal marriage line, to the child first preceding node. The child first preceding node can be drawn into the genealogical graph by the genealogical graphing system 110 during a subsequent recursive instruction.

The genealogical graphing system 110 can accommodate flexible ordering of spouses. When two spouses are parents, the genealogical graphing system 110 can attempt to position a male spouse to the west (left) and a female spouse to the east (right). However, if interior node represents the male spouse and the spouse first preceding node is the female spouse, the marriage relationship can be drawn with the male spouse to the east and the female spouse to the west.

To generate the interior node format when the first preceding node is the parent first preceding node, the genealogical graphing system 110 can draw the interior node and determine whether the second preceding node is a child of the first preceding node. In other words, the second preceding node is a sibling of the interior node, sharing the same parents. If the genealogical graphing system 110 determines that the second preceding node is not the child of the first preceding node, the genealogical graphing system 110 can generate a vertical line directed north from the interior node. The genealogical graphing system 110 can determine, from the memory 118, the other parent of the target node and then draw the node for the second parent by moving half the marriage line to the east. The marriage line can then be drawn west from the other parent to the parent first preceding node. The parent first preceding node can be drawn into the genealogical graph by the genealogical graphing system 110 during a subsequent recursive instruction.

If the genealogical graphing system 110 determines that the second preceding node is the child of the first preceding node (i.e. the sibling of the interior node), the recursive drawing instructions become dependent on both the first preceding node and the second preceding node. When this determination is made, the genealogical graphing system 110 can define a "sequel" for each individual. The sequel of an individual typically coincides with the first preceding node of that individual. However, in cases when the interior node has a sibling (sharing both parent) as the second preceding node, the second preceding node can become the sequel instead of the first preceding node. As the enriched node format can store the identifier of the first preceding node for the associated member, the enriched node format can also store the identifier of the sequel for the associated node. The identifier of the sequel for an associated node may also be referred to as a "sequel pointer". The interior node format for the interior node (i.e. the sibling closer to the target node) can, in this case, include the drawing instructions to draw both parents of the interior node. The genealogical graphing system 110 can determine the parents of the interior node by accessing the memory 118. The recursive drawing instructions of the genealogical graph can then go directly to the second preceding node bypassing both parents which have already been drawn. In this way, the sibling (i.e. the second preceding node) closer to the initial node can be stored as the sequel of the interior node closer to the target node.

As described above, the genealogical graphing system 110 can generate the interior node format to include the other parent (i.e. the spouse of the first preceding node). The other parent can be termed a "non-linking" parent. The term "non-linking" parent refers to a parent who is non-essential in connecting the path between the target node and the initial node. Displaying non-linking parents along the path from the initial member to the target member can be informative but unnecessary.

In some embodiments, the genealogical graphing system 110 can generate the interior node format by generating a connection to one or more related members in an adjusted format.

For example, the genealogical graphing system 110 can detect display and/or operating attributes associated with a display device, such as computing device A 122A or computing device B 122B, such as a display size and/or a resolution. Based on the detected display attributes of the display device, the genealogical graphing system 110 can determine whether the display device is associated with a large display device or a small display device. The genealogical graphing system 110 may designate the large or small display characteristics by comparing the detected display size with a threshold display size which represents a minimum display size required to be designated a large display device. When the genealogical graphing system 110 determines that the display device is associated with a small display, the genealogical graphing system 110 can generate the interior node format in the adjusted interior node format to accommodate the display size of the display device.

Figure 7C:
FIG. 7C shows an example adjusted interior node format.

FIG. 7C illustrates an example adjusted interior node format 222 for the individual "PEEW". To connect an interior node to a parent in the adjusted interior node format, the genealogical graphing system 110 only includes the parent within the path between the initial node and the target node, and omits the non-linking parent, such as the individual "PPDE" shown in the example interior node format 220 of FIG. 7B.

The genealogical graphing system 110 can issue separate drawing instructions for the adjusted interior node format. The key difference between the interior node format and the adjusted interior node format is that the non-linking parent is not drawn in the adjusted node format. Accordingly, the drawing instructions for the interior node format and the adjusted node format are identical when the first preceding node is the spouse first preceding node.

To generate the adjusted interior node format when the first preceding node is the child first preceding node, the genealogical graphing system 110 can draw the interior node followed by a vertical directed south. Similar to the interior node format, the child first preceding node can be drawn into the genealogical graph by the genealogical graphing system 110 during a subsequent recursive instruction.

To generate the adjusted interior node format when the first preceding node is the parent first preceding node, the genealogical graphing system 110 can draw the interior node followed by a vertical line directed north. Similar to the interior node format, the parent first preceding node can be drawn into the genealogical graph by the genealogical graphing system 110 during a subsequent recursive instruction. However, if the genealogical graphing system 110 determines that the second preceding node is the child of the first preceding node (i.e. the sibling of the interior node), the drawing instructions for the adjusted interior node format and the interior node format are identical. The other parent is drawn because, in this case, the other parent is no longer a non-linking parent. The genealogical graphing system 110 can determine the other parent from the memory 118.

Figure 7D:
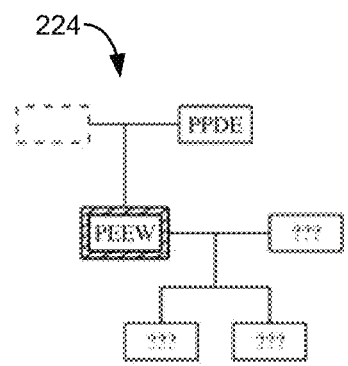
FIG. 7D shows an example target node format.

FIG. 7D shows an example target node format 224 for the individual "PEEW". In this example, the individual "PEEW" is the target node.

The genealogical graphing system 110 generates the target node format for the target node. Similar to the interior node format 220, the genealogical graphing system 110 can generate the target node format 224 in various ways depending on whether the first preceding node of the target node is a spouse first preceding node, a child first preceding node, or a parent first preceding node. In some embodiments, the genealogical graphing system 110 can generate an enriched node format for the target node to initiate the generation of the genealogical graph.

To generate the target node format when the first preceding node of the target node is the spouse first preceding node, the genealogical graphing system 110 can draw the target node and generate nodes for the parents of the target node that can be connected to the target node by generating a line at a suitable distance north from the target node. Subsequently, the genealogical display system 110 can generate a line a suitable distance to the west of the target node. Stopping halfway along the suitable distance, the genealogical graphing system 110 can determine the spouse first preceding node and children from this spouse from the memory 118. If the target node has more than one spouse, the genealogical graphing system 110 can draw the nodes for all spouses and children resulting from those spouses, excluding the spouse first preceding node. The genealogical graphing system 110 can then continue drawing the line drawn to the west to connect the target member to the spouse first preceding node. The spouse first preceding node can be drawn into the genealogical graph by the genealogical graphing system 110 during a subsequent recursive instruction.

In some embodiments, the genealogical graphing system 110 can determine the suitable distance by first determining whether the second preceding node of the target node is a parent of the spouse first preceding node. If the second preceding node is the parent of the spouse first preceding node (i.e. the second preceding node is an in-law of the target member), the genealogical graphing system 110 can assign a suitably larger distance to accommodate the presence of both parents of the spouse first preceding node in addition to both parents of the target node when the interior node format is being generated for the interior nodes on the genealogical graph.

Figure 24:
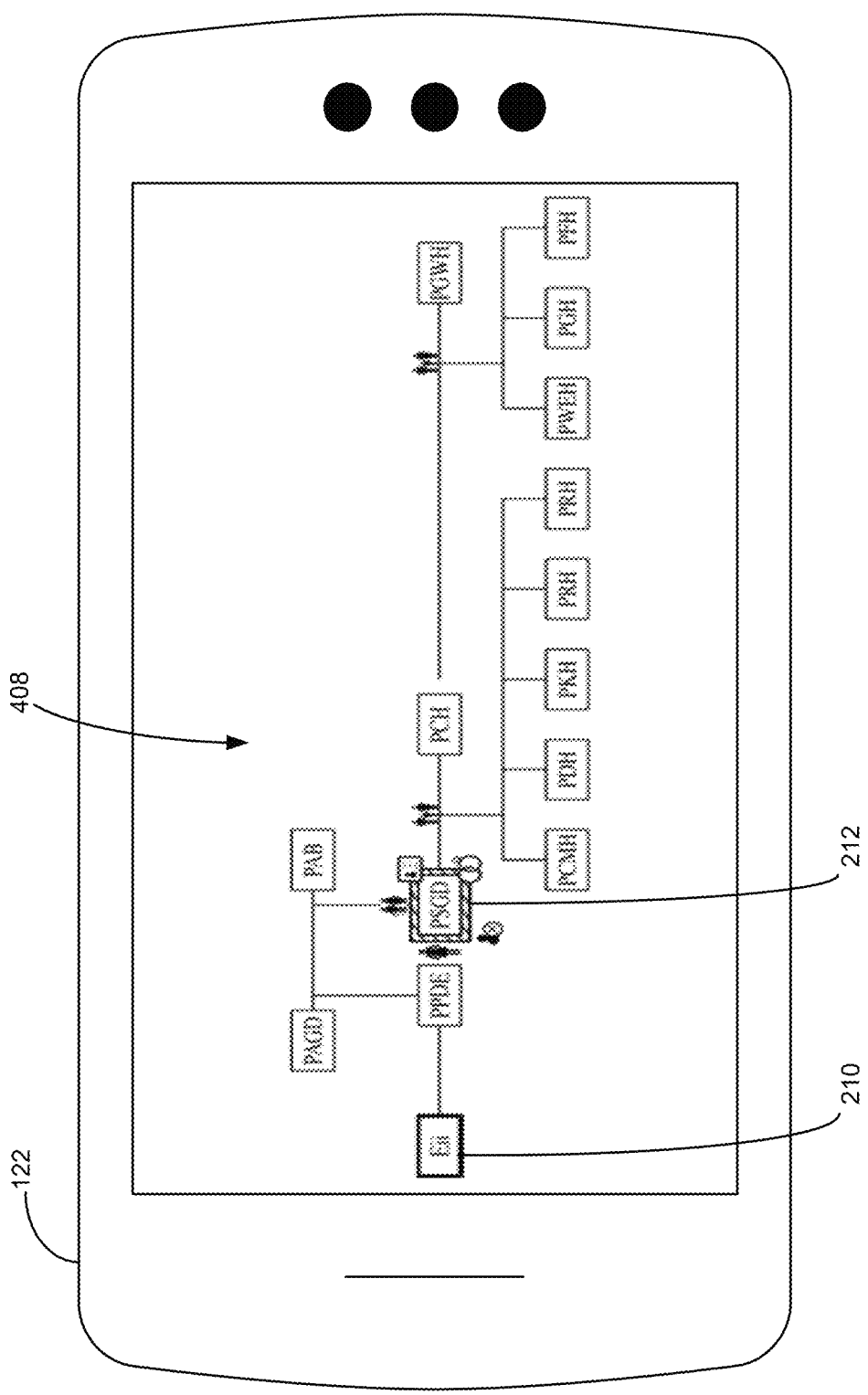
FIG. 24 shows another example genealogical graph following a user interaction received at the computing device of FIG. 23.

In some embodiments, when the spouse is not the first preceding node of the target node, the genealogical graphing system 110 can draw nodes for all spouses of the target node at a suitable distance east from the target node (see e.g., FIG. 24). Furthermore, the genealogical graphing system 110 can generate all children the target node had with these spouses by stopping halfway along their corresponding marriage line to include nodes for the children. The genealogical graphing system 110 can include the nodes for the children at a fixed separation distance. In some embodiments, it can be visually beneficial to first move by half the fixed separation distance between consecutive children before plotting a first child. To position the node for a spouse, the genealogical graphing system 110 can, in some embodiments, maintain the relative eastward vector of the node for the last child of the preceding spouse. This can provide a clear visual separation between the spouses and children of each spouse (see e.g. FIG. 24). After concluding the drawing of all spouses, the genealogical graphing system 110 can reset the inverse of the final relative eastward vector. Since the drawing instructions are relative and vectorial, the genealogical graphing system 110 can perform this reset so that it is ready for generating a subsequent recursive instruction.

To generate of the target node format when the first preceding node of the target node is the child first preceding node, the genealogical graphing system 110 can draw the target node and determine the other parent of the child first preceding node and generate the node for that other parent. The node for that other parent can be connected to the target node by the genealogical graphing system 110 with a horizontal line directed westward by a constant (i.e. indicating a spousal relationship). The node for the other parent, in some embodiments, can be in the enriched node format. Next, the genealogical graphing system 110 can draw the nodes for the children from the marriage of the target member and the other parent, except the child first preceding node. The child first preceding node can be drawn into the genealogical graph by the genealogical graphing system 110 in a subsequent recursive instruction. The child first preceding node will be the westmost child among the children, regardless of the birthday of the children.

To generate the target node format when the first preceding node of the target node is the parent first preceding node, the genealogical graphing system 110 can draw the target node and determine whether the second preceding node is a child of the first preceding node. In other words, the second preceding node is a sibling of the target node, sharing the same parents. If the genealogical graphing system 110 determines that the second preceding node is not the child of the first preceding node, the genealogical graphing system 110 can determine the spouse (or spouses) of the target node from the memory 118. As described earlier, the genealogical graphing system 110 can generate nodes for the spouses together with their respective children to the east of the target node. The genealogical graphing system 110 can generate a vertical line from the target node to the marriage line directed north. The genealogical graphing system 110 can then determine the other parent of the target node from the memory 118 and generate the node for the other parent by moving half the width of a marriage line to the east. The genealogical graphing system 110 can then generate the marriage line west from the node of the other parent to the parent first preceding node. The genealogical graphing system 110 can draw the parent first preceding node into the genealogical graph in a subsequent recursive instruction.

If the genealogical graphing system 110 determines that the second preceding node is the child of the first preceding node (i.e. the sibling of the target node), the recursive drawing instructions become dependent on both the first preceding node and the second preceding node. When this determination is made, the genealogical graphing system 110 relies on the sequel stored in the enriched node format for each member (i.e. the sequel point). As described above, the sequel of an individual typically coincides with the first preceding node of that individual. However, in cases where the target node has their sibling as the second preceding node, the second preceding node can become the sequel instead of the parent first preceding node. In this case, the drawing instructions can include, not just the target node and the line to connect the target node with their parent or parents (i.e. their first preceding node), but also the parent first preceding node and the node of the other parent who represent the shared parents with the second preceding node. The genealogical graphing system 110 can determine the parents of the target node by accessing the memory 118. The recursive drawing instructions of the genealogical graph can then go directly to the second preceding node, bypassing both parents which have already been drawn. In this way, the sibling (i.e. the second preceding node) closer to the initial node can be stored as the sequel of the target node.

Referring specifically to FIGS. 8A and 8B illustrates an example of how the genealogical graphing system 110 can use sequel pointers to draw a genealogical graph as opposed to first preceding nodes. FIG. 8A shows a genealogical graph 158 that includes Queen Elizabeth II (Eii) as an initial member 160 and Prince George William of Hanover (PGWH) as a target member 162. In this particular example, no information is known about the parents or children of PGWH. FIG. 8B shows an exploded genealogical graph 158' corresponding to the genealogical graph 158 of FIG. 8A. The exploded genealogical graph 158' shows that it is made up of one node (PGWH) in target node format, two nodes (PSGD, PPDE) in interior node format and one node (Eii) in enriched node format. The exploded genealogical graph 158' further includes a sequel pointer 164 of PGWH, a sequel pointer 166 of PSGD and a sequel pointer 168 of PPDE. The sequel pointer 164 of PGWH points to its first preceding node, in this case PSGD. Similarly, the sequel pointer 168 of PPDE points to its first preceding node, in this case Eii. However, the sequel pointer 166 of PSGD is its second preceding node, in this case PPDE. At first, all sequel pointers can be initially set to be identical to their first preceding node. However, when it is determined that the first preceding node is a parent, and the second preceding node is a child of the first preceding node, the genealogical graphing system 110 can overwrite the sequel pointer that has been initialized and set it to the second preceding node instead. Accordingly, the sequel of PSGD is neither PAGD nor PAB since PAGD and PAB represent the shared parents of siblings PSGD and PPDE. It is immaterial to the genealogical graphing system 110 as to which parent (PAGD or PAB) is the first preceding node of PSGD. As a result, the interior node format of interior node PSGD can include drawing instructions for the parents of PSGD and PPDE.

Figure 9:
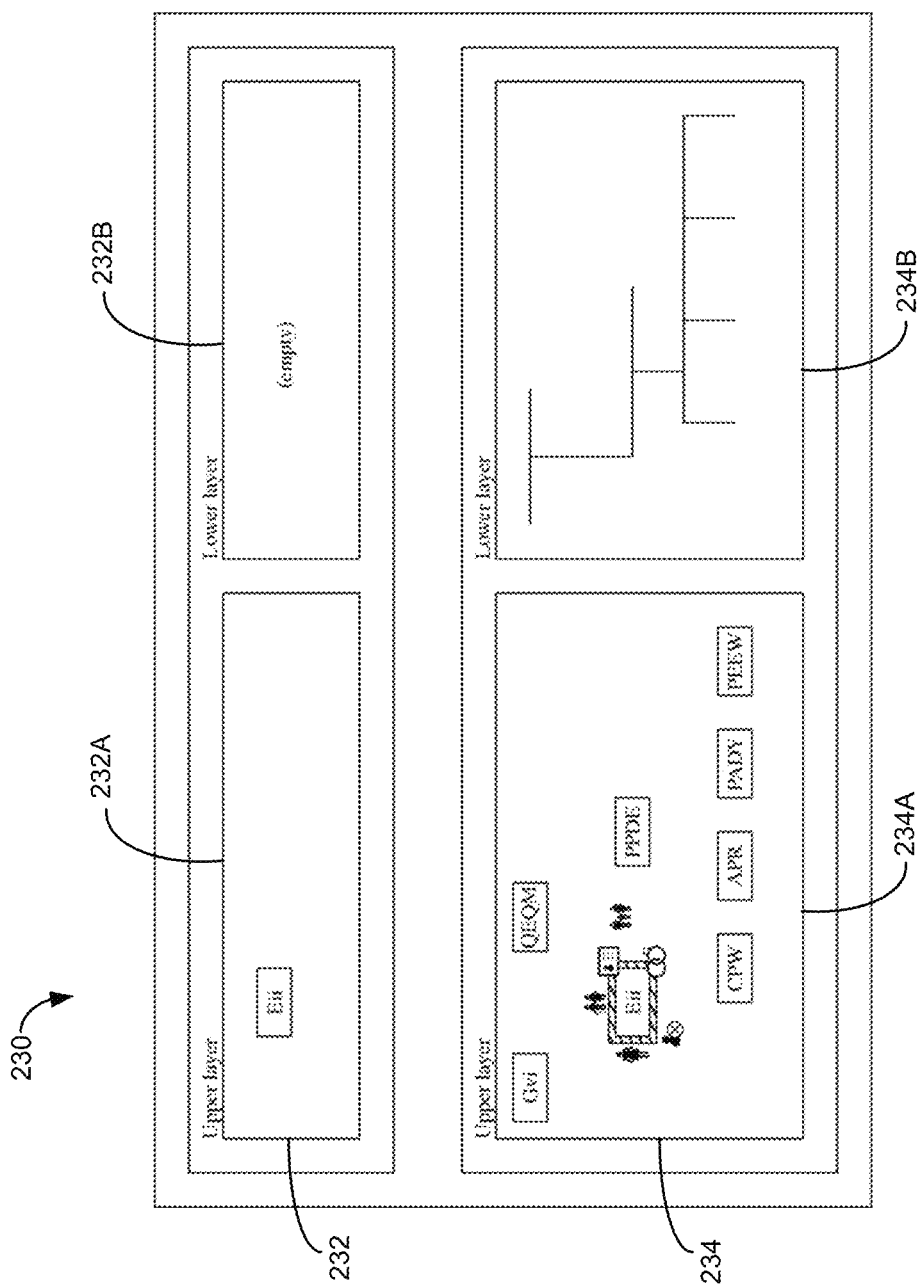
FIG. 9 shows a sample genealogical graph separated into an upper layer and a lower layer.

Referring now to FIG. 9, which shows a sample genealogical graph 230 separated into an upper layer and a lower layer. The upper layer and the lower layer can be displayed superimposed with the elements of the upper layer hiding the elements of the lower layer.

When generating the genealogical graph, the genealogical graphing system 110 can generate the elements in one or more layers. FIG. 9 shows an example interior node format 232 separated into an upper layer 232A and a lower layer 232B, and an example target node format 234 separated into an upper layer 234A and a lower layer 234B. By overlaying the upper layers 232A, 234A on top of the respective lower layers 232B, 234B, the genealogical graphing system 110 can generate the genealogical graph for the individual Eii. The lower layers 232B, 234B can include the edges for connecting nodes to each other. The upper layers 232A, 234A can include the nodes and related data, such as names, images, and/or other attributes of the individuals associated with the nodes.

As shown in FIG. 9, the edges between the nodes in the target node format 234 can be included in the lower layer 234B. In some embodiments, an enriched node format can be included for one or more nodes and the node in the enriched node format can overlay the nodes in any of the interior node format and target node format. The lower layer can be drawn first, and the upper layer second. Hence, parts of the edges in the lower layer can be occluded by the enriched node formats in the upper layer. Each interior node format and each target node format can include parts to be drawn on the lower layer and parts to be drawn on the upper layer.

As described above, each node format (e.g., enriched node format, interior node format, adjusted node format, target node format) can include a set of recursive drawing instructions. The genealogical graphing system 110 can maintain planarity of a genealogical graph by following the recursive drawing instruction. The displaying of a genealogical graph can be recursively drawn from the target member to the initial member, by following the sequel (not the first preceding member) that can be stored in the enriched node format of each member.

First, the target node format of the target member can be drawn. If the target member is the same as the initial member (i.e. a path of one person), no recursive instructions are necessary. Second, the interior node format of the identified sequel (or the adjusted interior node format on small display devices) can be drawn. Third, the sequel of the sequel can be recursively identified and drawn. When the initial node (corresponding to the initial member) is reached, the recursive drawing instructions can stop. The enriched node format of the initial member completes the drawing of the genealogical graph.

As the recursive drawing instructions start from the target node, the genealogical graphing system 110 can generate the target node in the target node format with an absolute (i.e., not relative) position at an origin of a coordinate system. When the drawing is completed for display, regardless of the length of the path, and regardless of the number of recursive drawing instructions, a bounding box of the drawing can be identified from the absolute position at the origin of the coordinate system. The genealogical graphing system 110 may generate a genealogical graph using either an immediate or a retained drawing mode.

If the genealogical graphing system 110 is implemented using the retained drawing mode, it can suffice to set the computed bounding box as the bounding box of the root of the visible genealogical graph. If the genealogical graphing system 110 is implemented using the immediate drawing mode, the genealogical graphing system 110 can be initialized such that the bounding box is centered on the display device. The recursive drawing instructions can then be carried out, knowing that the genealogical graph cannot exceed the predetermined bounding box. The bounding box is described in more detail below with reference to FIGS. 31A to 32E.

Reference will now be made to FIGS. 10A to 18B for illustrating some example elements that can be generated by the genealogical graphing system 110 for generating genealogical graphs. The example elements are various paths between an initial member I and a target member T for various degrees of genealogical relationships to be illustrated in the genealogical graphs.

FIGS. 10A to 10C show example genealogical graphs 236, 238, and 240, respectively, of first-degree relationships for small displays. The genealogical graph 236 shows a relationship between a target member who is the child of the initial member. The genealogical graph 238 shows a relationship between a target member who is the parent of the initial member. The genealogical graph 240 shows a relationship between a target member who is the spouse of the initial member.

FIGS. 11A and 11B show example genealogical graphs 242 and 244, respectively, of first-degree relationships for large displays.

The genealogical graph 242 corresponds to the genealogical graph 236. In the genealogical graph 242, both parents of the target member are shown, even non-linking parent 246A, since space is not limited at the display device. Similarly, the genealogical graph 244 shows the non-linking spouse 246B of the target member, whereas the non-linking spouse 246B is not shown in the genealogical graph 238.

FIGS. 12A to 12J show example genealogical graphs 248, 250, 252, 254, 256, 258, 260, 262, 264 and 266, respectively of second-degree relationships for small displays. FIGS. 13A to 13C show example genealogical graphs 272, 274, and 276, respectively, of second-degree relationships for large displays.

The genealogical graph 248 shows that the target member is a grandchild of the initial member. The genealogical graph 272 of FIG. 13A similarly shows that the target member is the grandchild of the initial member with the non-linking spouses also shown.

The genealogical graph 250 shows that the target member is a grandparent of the initial member. The genealogical graph 274 of FIG. 13B similarly shows that the target member is the grandparent of the initial member with the non-linking spouses also shown.

The genealogical graph 252 shows that the target member is a sibling of the initial member. The genealogical graph 254 shows that the target member is a step-sibling of the initial member (a sibling who shares only one parent).

The genealogical graph 256 shows that the target member is a parent-in-law of the initial member. The genealogical graph 276 of FIG. 13C similarly shows that the target member is the parent-in-law of the initial member with the non-linking spouses also shown.

The genealogical graph 258 shows that the target member is a child-in-law of the initial member. The genealogical graph 260 shows that the target member is also a child-in-law of the initial member. The genealogical graph 262 shows that the target member is also a parent-in-law of the initial member. The genealogical graph 264 shows that the target member and the initial member are parents of a child 268 but are not married. The genealogical graph 266 shows that the target member and the initial member are, or were, a spouse of an individual 270.

FIGS. 14A to 14J show example genealogical graphs 278, 280, 282, 284, 286, 288, 290, 292, 294 and 296, respectively, of third-degree relationships for small displays. FIGS. 15A to 15C show example genealogical graphs 298, 300, and 302, respectively, of third-degree relationships for large displays.

The genealogical graph 278 shows that the target member is a great-grandchild of the initial member. The genealogical graph 298 of FIG. 15A similarly shows that the target member is the great-grandchild of the initial member with the non-linking spouses also shown.

The genealogical graph 280 shows that the target member is a great-grandparent of the initial member. The genealogical graph 282 shows that the target member is an aunt or an uncle of the initial member. The genealogical graph 284 shows that the target member is a nephew or a niece of the initial member. The genealogical graph 286 shows that the target member is a grandparent-in-law of the initial member. The genealogical graph 288 shows that the target member is a grandchild-in-law of the initial member. The genealogical graph 290 shows that the target member is a brother-in-law or a sister-in-law of the initial member. The genealogical graph 292 shows that the target member is also a brother-in-law or a sister-in-law of the initial member.

The genealogical graph 294 shows that the target member is an in-law of the initial member. The genealogical graph 300 of FIG. 15B similarly shows that the target member is the in-law of the initial member with the non-linking spouses also shown.

The genealogical graph 296 shows that the target member is a daughter-in-law or a son-in-law of the initial member. The genealogical graph 302 of FIG. 15C similarly shows that the target member is the daughter-in-law or son-in-law of the initial member with the non-linking spouses also shown.

FIGS. 16A to 16M show example genealogical graphs 304, 306, 308, 310, 312, 314, 316, 318, 320, 322, 324, 326 and 328, respectively, of fourth-degree relationships for small displays.

The genealogical graph 304 shows that the target member is a great-great-grandchild of the initial member. The genealogical graph 306 shows that the target member is a great-great-grandparent of the initial member. The genealogical graph 308 shows that the target member is a great-aunt or a great-uncle of the initial member. The genealogical graph 310 shows that the target member is a great-nephew or a great-niece of the initial member. The genealogical graph 312 shows that the target member is a great-grandparent-in-law of the initial member. The genealogical graph 314 shows that the target member is a great-grandchild-in-law of the initial member. The genealogical graph 316 shows that the target member is an in-law of a child 330 of the initial member. The genealogical graph 318 shows that the target member is a cousin of the initial member. The genealogical graph 320 shows that the target member is a brother-in-law or a sister-in-law of the initial member. The genealogical graph 322 shows that the target member is an in-law of a sibling 332 of the initial member. The genealogical graph 324 shows that the target member is an aunt or uncle of a spouse 334 of the initial member. The genealogical graph 326 shows that the target member is a spouse of an aunt or uncle 336 of the initial member. The genealogical graph 328 shows that the target member is a nephew or niece of a spouse 338 of the initial member.

FIGS. 17A and 17B show example genealogical graphs 340 and 342, respectively, of fifth-degree relationships for small displays. FIGS. 18A and 18B show example genealogical graphs 350 and 352, respectively, of fifth-degree relationships for large display devices.

The genealogical graph 340 shows that the target member is an in-law of an aunt or uncle 344 of the initial member. The genealogical graph 350 of FIG. 18A similarly shows that the target member is an in-law of an aunt or uncle 344 of the initial member with the non-linking spouses also shown.

The genealogical graph 342 shows that the target member is an in-law of a brother-in-law or a sister-in-law 348 of the initial member. The genealogical graph 352 of FIG. 18B similarly shows that the target member is an in-law of a brother-in-law or a sister-in-law 346 of the initial member with the non-linking spouses also shown.

Figure 19A:
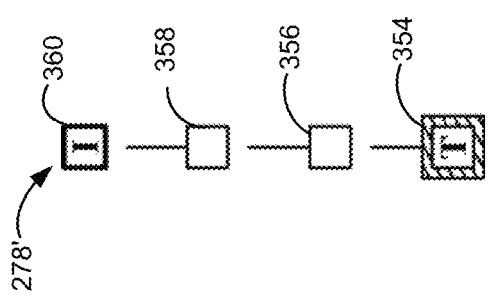
FIG. 19A is an exploded version of the example genealogical graph shown in FIG. 14A.
Figure 19B:
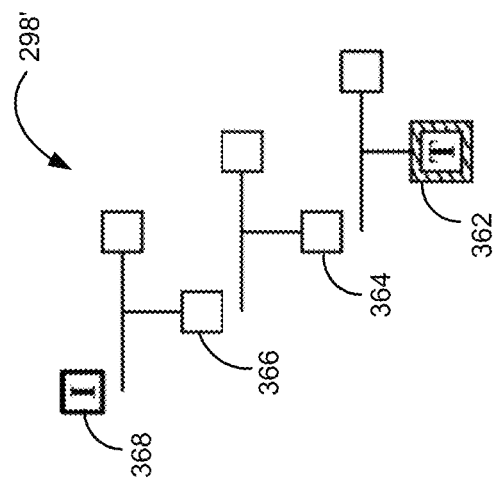
FIG. 19B is an exploded version of the example genealogical graph shown in FIG. 15A.

FIGS. 19A to 19D show exploded versions for a small subset of the example genealogical graphs of FIGS. 10A-18B. The exploded versions of the genealogical graphs show the associated genealogical graph disassembled into its constituent elements. In this way, the exploded genealogical graphs of FIGS. 19A to 19D may further illustrate how the different node formats are used by to the genealogical graphing system 110 to draw a genealogical graph. FIG. 19A shows an exploded genealogical graph 278' corresponding to the example genealogical graph 278 of FIG. 14A. The genealogical graph 278 shows that the target member is a great-grandchild of the initial member. As shown, the exploded genealogical graph 278' includes one node (i.e. target node 354) in target node format, two nodes (i.e. interior nodes 356, 358) in adjusted interior node format and one node (i.e. initial node 360) in enriched node format. FIG. 19B shows an exploded genealogical graph 298' corresponding to the example genealogical graph 298 of FIG. 15A. The genealogical graph 298 similarly shows that the target member is the great-grandchild of the initial member with the non-linking spouses also shown. That is, the genealogical graph 298 is for large displays. As shown, the exploded genealogical graph 298' includes one node (i.e. target node 362) in target node format, two nodes (i.e. interior nodes 364, 366) in interior node format and one node (i.e. initial node 368) in enriched node format.

Figure 19C:
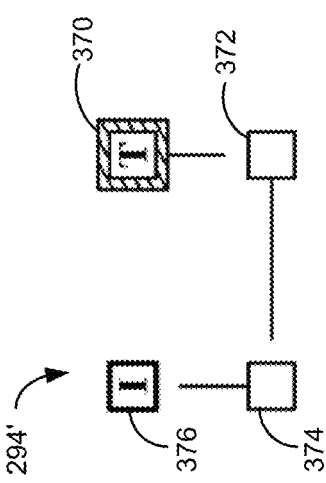
FIG. 19C is an exploded version of the example genealogical graph shown in FIG. 14I.
Figure 19D:
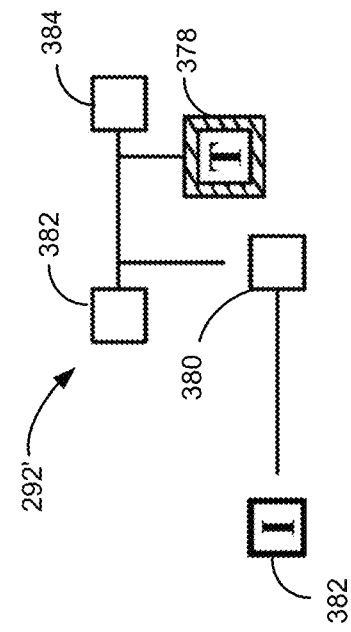
FIG. 19D is an exploded version of the example genealogical graph shown in FIG. 14H.

FIG. 19C shows an exploded genealogical graph 294' corresponding to the example genealogical graph 294 of FIG. 14I. The genealogical graph 294 shows that the target member is an in-law of the initial member. As shown, the exploded genealogical graph 294' includes one node (i.e. target node 370) in target node format, two nodes (i.e. interior nodes 372, 374) in adjusted interior node format and one node (i.e. initial node 376) in enriched node format. FIG. 19D shows an exploded genealogical graph 292' corresponding to the example genealogical graph 292 of FIG. 14H. The genealogical graph 292 shows that the target member is a brother-in-law or a sister-in-law of the initial member. As shown, the exploded genealogical graph 292' includes one node (i.e. target node 378) in target node format, one node (i.e. interior node 380) in adjusted interior node format and one node (i.e. initial node 382) in enriched node format.

Although the exploded genealogical graphs 278', 298', 294' and 292' show three-degree relationships between the initial member I and the target member T, the exploded genealogical graph 292' contains one less element than the exploded genealogical graphs 278', 298' and 294'. This is because the sequel pointer of the target node 378 in the exploded genealogical graph 292' is a second preceding node (i.e. interior node 380). That is, the target node 378 and the interior node 380 share the same parents (i.e. nodes 382, 384). As a result, the drawing instructions can include instructions to draw the parents (382, 384) in the target node format of target node 378.

In some embodiments, the user can access the public database of potentially millions of historical figures. For example, the public database may be accessed through a URL beginning with "eveskids.com/public/path". The user may select a first historical figure as the initial member. For example, the first historical figure may be represented by a short form (see e.g., Table 1). Once the initial member is selected, the genealogical graphing system can retrieve from the memory 118 all members (i.e. nodes) within two relational degrees of the initial member, as well as the connections within that set of nodes. Next, the genealogical graphing system 110 can compute a breadth-first traversal starting from the initial member (i.e. initial node) (see e.g. FIG. 5A). The genealogical system 110 can then reverse the edges of the breath-first traversal to determine the preceding relationship (i.e. first preceding node) (see e.g., FIG. 5B). Next, the genealogical system 110 can send a message to the computing device 122 containing the initial node together with the nodes for the first degree and the second degree relatives. In the message, the genealogical system can include the enriched, interior, adjusted interior, and target node formats for the initial node, as well as the nodes for the first degree and second degree relatives.

For example, when the user selects a node representing a first degree relative, the computing device 122 displays the selected node as the target node (the initial node remains unchanged). As soon as the user selects this node, the computing device 122 can send a request genealogical graphing system 110 asking for the second degree relatives for the newly selected target node. The genealogical graphing system 110 does not need to return the first degree relatives of the newly selected target node because this information has already been sent. If network lag is particularly high, the genealogical graphing system 110 can send up to third (or more) relatives of the initial node. In this way, the user can select two nodes as the new target nodes in quick succession without experiencing any interruption due to network lag.

In some embodiments, the genealogical graphing system 110 can receive user inputs at a genealogical graph displayed at a display screen of one or more computing devices 122, and generate other genealogical graphs accordingly. For example, the genealogical graphing system 110 can receive a user input selecting a node in an example genealogical graph. To generate a new genealogical graph, the node selected can be any node, other than the current target node, displayed in the current genealogical graph. In response to receiving the selected node from the user input, the genealogical graphing system 110 can generate the new genealogical graph for the selected node. The selected node can, in some embodiments, be a new target member of the new genealogical graph. The genealogical graphing system 110 can generate the new genealogical graph to display the connection of the initial member of the current genealogical graph to the new target member.

In response to the selection of the new target member, the genealogical graphing system 110 can determine the new members needed for the new genealogical graph and can retrieve the data related to the new members from the memory 118.

FIGS. 20 to 28 illustrate example genealogical graphs on a display screen for illustrating example path interactions.

Figure 20:
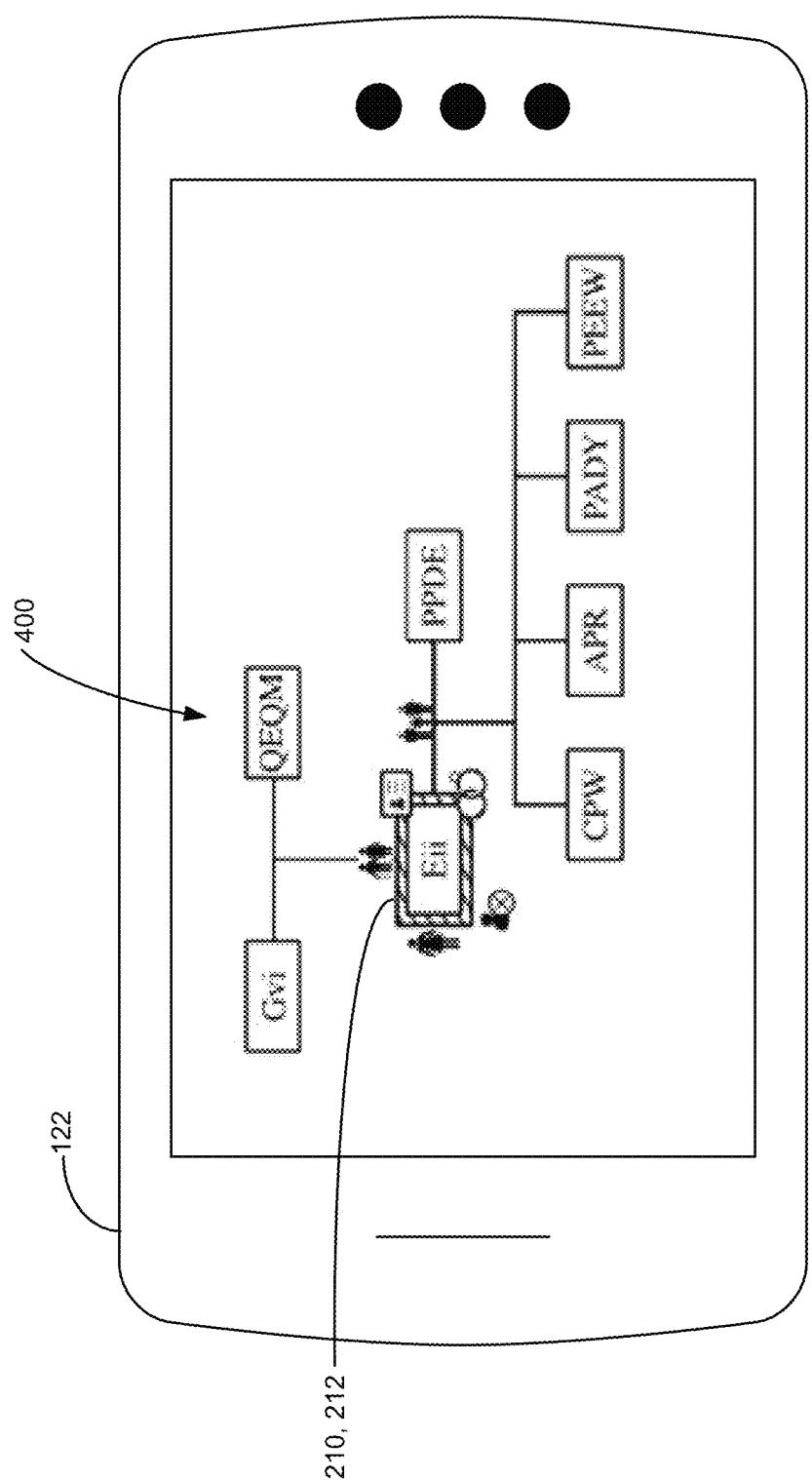
FIG. 20 shows an example genealogical graph displayed at a display screen of an example computing device, in accordance with an example embodiment.
Figure 21:
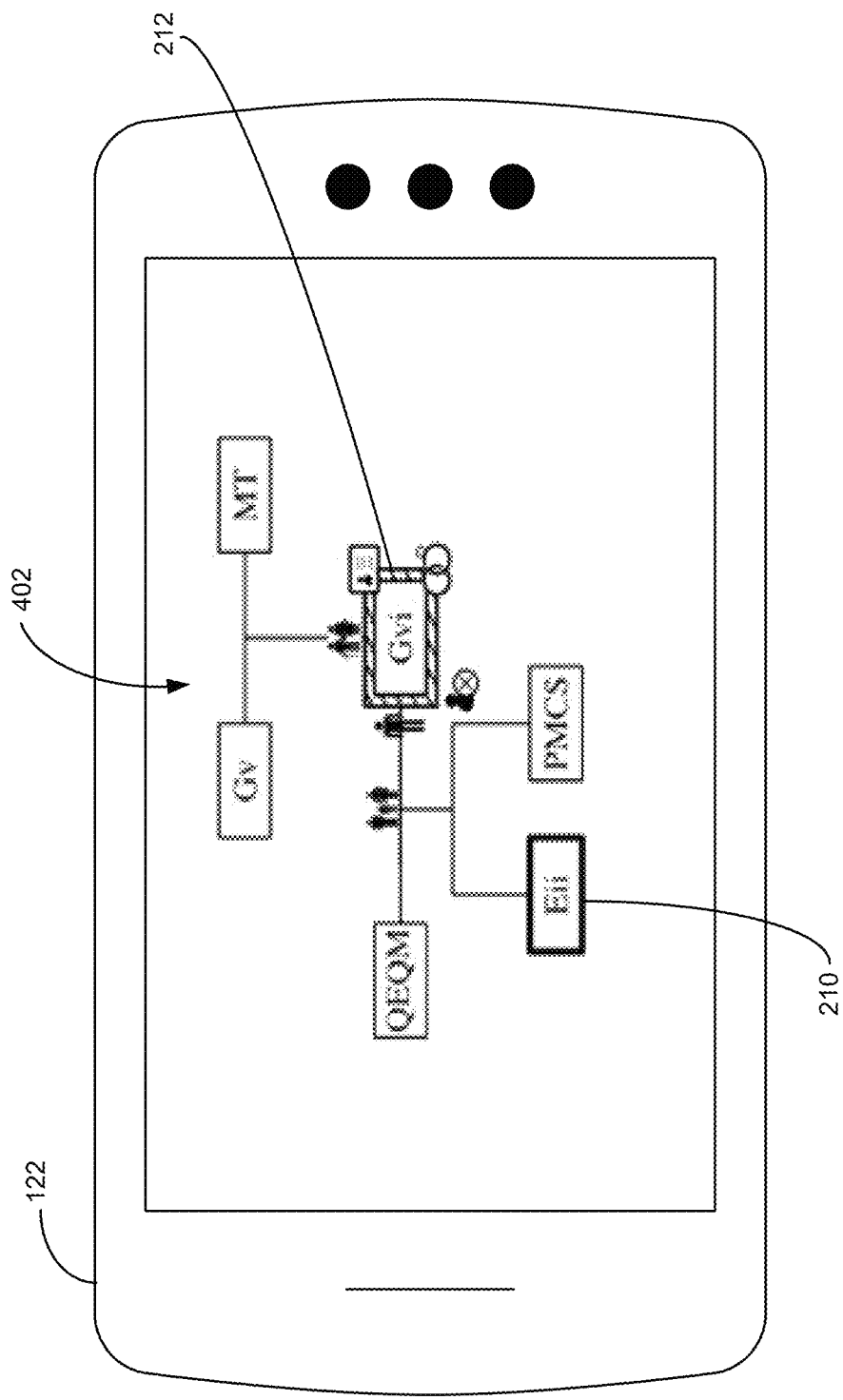
FIG. 21 shows another example genealogical graph following a user interaction received at the computing device of FIG. 20.

FIG. 20 shows an example genealogical graph 400 displayed at a display screen of computing device 122. The genealogical graph 400 includes Queen Elizabeth II (Eii) as a target member 212 and an initial member 210, and shows first-degree relatives of Eii.

A user viewing the genealogical graph 400 can select any of the displayed nodes for interacting with the illustrated path of Eii. For example, the genealogical graphing system 110 can receive a user input indicating the node associated with Gvi (a parent of Eii) is selected. In response, the genealogical graphing system 110 can generate the genealogical graph 402 shown in FIG. 21. In the genealogical graph 402, Gvi is the target member 212, while Eii remains the initial member 210. As the target member 212 is now Gvi, the genealogical graph 402 shows the first-degree relatives of Gvi.

In another example embodiment, the genealogical graphing system 110 can receive a user input via the genealogical graph 400 in FIG. 20 indicating the node associated with PPDE (a spouse of Eii) is selected. In response, the genealogical graphing system 110 can generate the genealogical graph 404 shown in FIG. 22. In genealogical graph 404, PPDE becomes the target member 212, while Eii remains the initial member 210. The genealogical graph 404 displays the first-degree relatives of PPDE.

Figure 22:
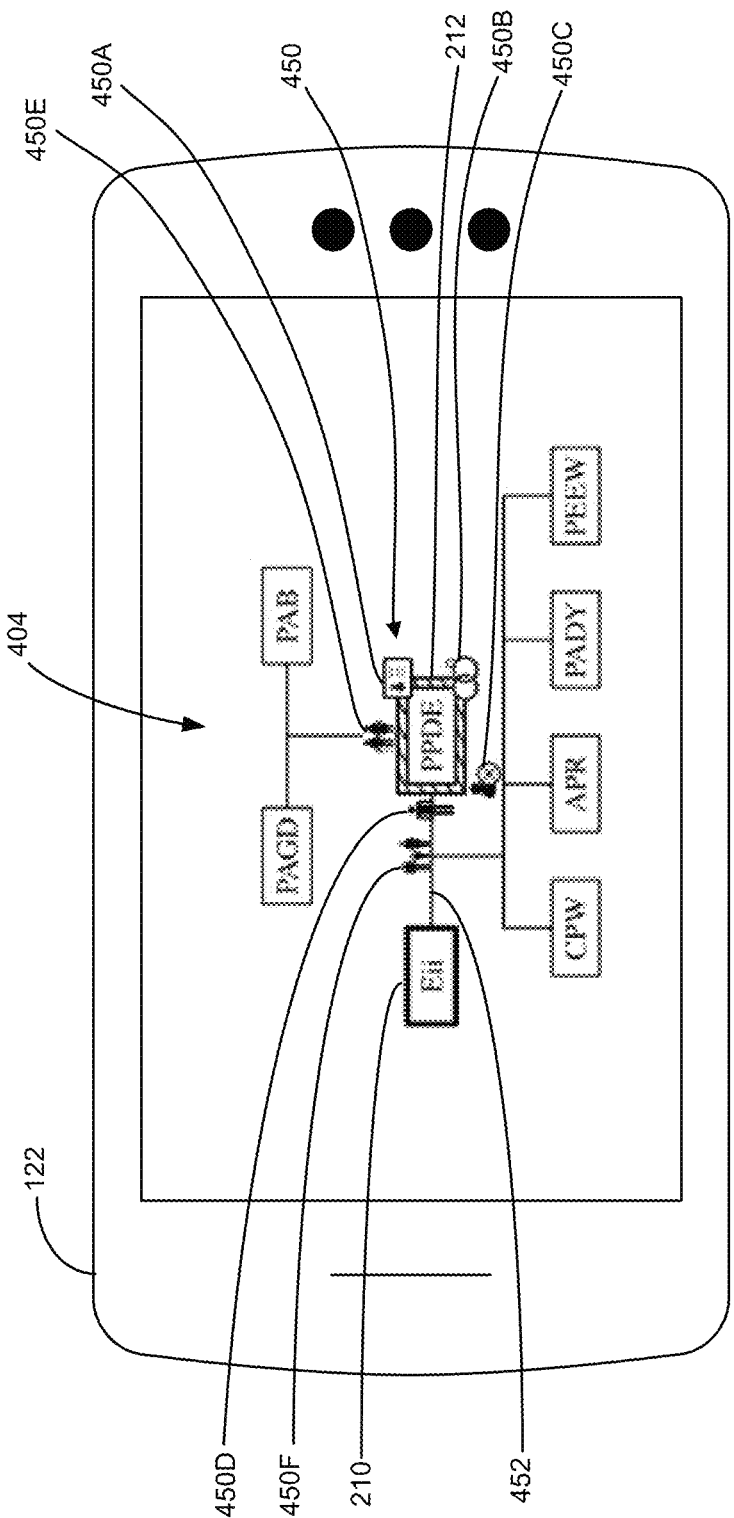
FIG. 22 shows another example genealogical graph following a user interaction received at the computing device of FIG. 20.

In another example embodiment, the genealogical graphing system 110 can receive a user input via the genealogical graph 404 in FIG. 22 indicating the node associated with PAGD (a parent of PPDE) is selected. In response, the genealogical graphing system 110 can generate the genealogical graph 406 shown in FIG. 23. In the genealogical graph 406, PAGD becomes the target member 212, while Eii remains the initial member 210. The genealogical graph 406 displays the first-degree relatives of PAGD as well as a path between Eii and PAGD even though Eii is not a first-degree relative of PAGD.

Via the genealogical graph 406, the genealogical graphing system 110 can receive a user input indicating the node associated with PSGD (a child of PAGD) is selected. In response, the genealogical graphing system 110 can generate the genealogical graph 408 shown in FIG. 24. In the genealogical graph 408, PSGD becomes the target member 212, while Eii remains the initial member 210. As a result, the genealogical graph 408 displays the first-degree relatives of PSGD as well as a path between PSGD and Eii even though Eii is not a first-degree or second-degree relative of PSGD.

Figure 25:
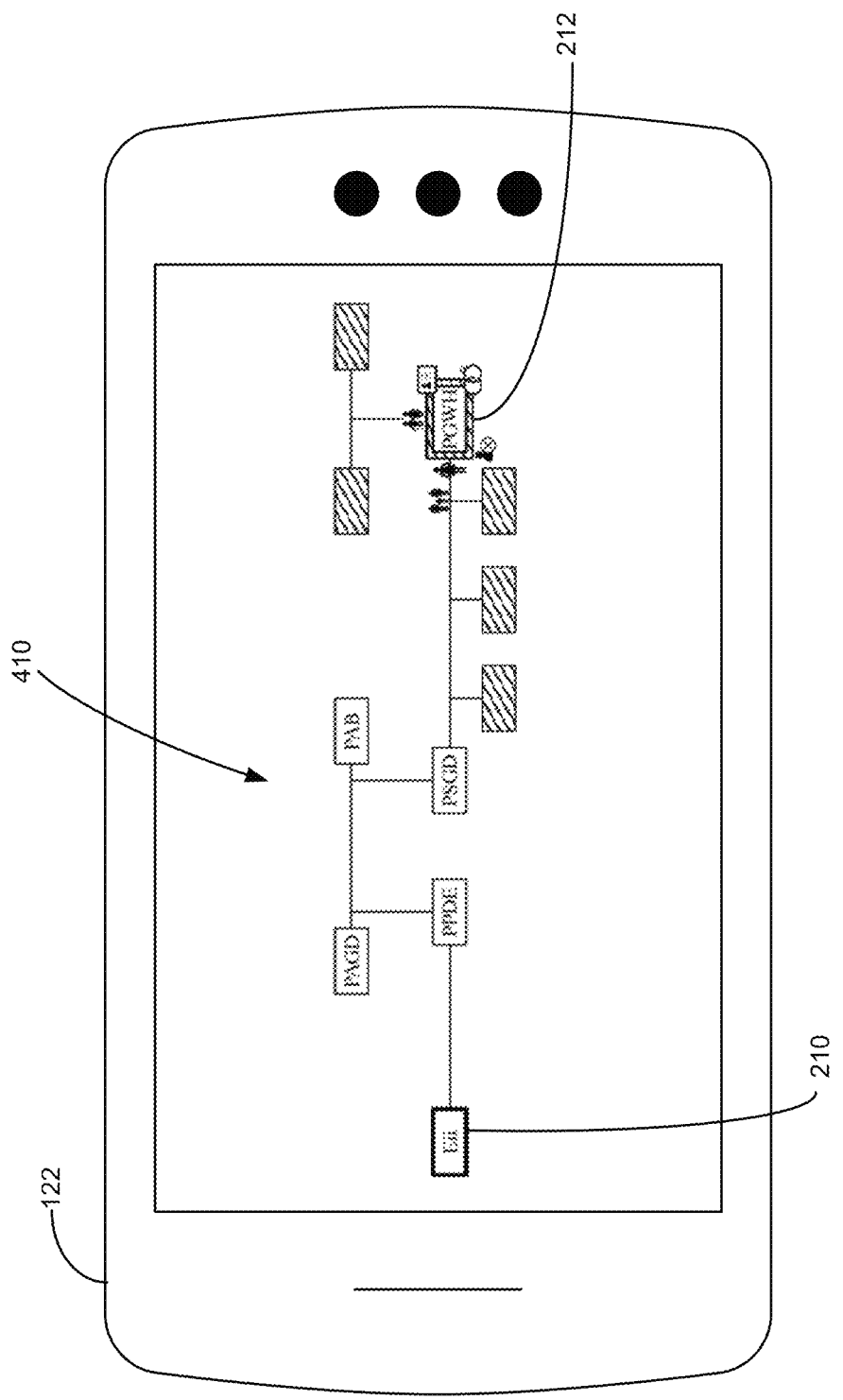
FIG. 25 shows another example genealogical graph following a user interaction received at the computing device of FIG. 24.

Via the genealogical graph 408, the genealogical graphing system 110 can receive a user input indicating the node associated with PGWH (one of two spouse of PSGD) is selected. In response, the genealogical graphing system 110 can generate the genealogical graph 410 shown in FIG. 25. In the genealogical graph 410, PGWH becomes the target member 212, while Eii remains the initial member 210. The genealogical graph 410 displays the first-degree relatives of PGWH and a path between Eii to PGWH even though Eii is not a first-degree, second-degree or third-degree relative of PGWH. Since PGWH is the target member 212, the genealogical graph 410 does not display the marriage of PCH to PSGD and the five children from that marriage which are shown in genealogical graph 408 of FIG. 24 and instead, the parents of PGWH, the target member 212, are now shown. FIG. 25 also shows an alternative method for drawing the three children of PSGD and PGWH. In FIG. 25 the three children are shown directly connected to the marriage line, whereas in FIG. 24 they are collectively connected via one joint to the marriage line.

Via the genealogical graph 410, the genealogical graphing system 110 can receive a user input indicating the node associated with PTD (a parent of PGWH). In response, the genealogical graphing system 110 can generate the genealogical graph 412 shown in FIG. 26. In the genealogical graph 412, PTD becomes the target member 212, while Eii remains the initial member 210. The genealogical graph 412 displays the first-degree relatives of PTD and a path from Eii to PTD even though Eii is not a first-degree, second-degree, third-degree or fourth-degree relative of PTD. In this example, the genealogical graphing system 110 is unable to locate further data from the memory 118 in respect of the parents of PTD and therefore, no parents are displayed.

Referring again to FIG. 20, the genealogical graphing system 110 can receive a user input via the genealogical graph 400 in FIG. 20 indicating the node associated with CPW (a child of Eii) is selected. In response, the genealogical graphing system 110 can generate the genealogical graph 414 shown in FIG. 27.

In the genealogical graph 414, CPW becomes the target member 212, while Eii remains the initial member 210. The genealogical graph 414 displays the first-degree relatives of CPW, which include relationships resulting from the marriages to the target member 212 (PDW, CDC), and the children of all marriages/relationships (PW, PH). In response to receiving a user input via the genealogical graph 414 indicating the node associated with PDW (a spouse of CPW) is selected, the genealogical graphing system 110 can generate the genealogical graph 416 shown in FIG. 28. In genealogical graph 416, PDW becomes the target member 212, while Eii remains the initial member 210. The genealogical graph 416 displays the first-degree relatives of PDW and the path from Eii to PDW even though Eii is not a first-degree relative of PDW. Since PDW is the target member 212, the genealogical graph 416 does not display the second spouse (CDC) of CPW that is shown in the genealogical graph 414 of FIG. 27 and instead, shows the parents of PDW.

In the example embodiments shown in FIGS. 20 to 28, only the target node (target member 212) is associated with a set of editing icons 450. For example, in FIG. 22, the target node (target member 212) is associated with a set of editing icons 450 that include an icon for changing the name of the target 450A, an icon for inserting a spouse to the target 450B, an icon for deleting the target 450C, an icon for changing the sex of the target 450D, an icon for inserting a parent to the target 450E, and an icon for inserting a child to the marriage 450F. In some embodiments, fewer or more editing icons can be associated with the target node 212. In other embodiments, editing icons can similarly be associated with one or more other nodes in a genealogical graph.

The icons associated with a node can vary depending on the relationships associated with that node. For example, when the genealogical graphing system 110 determines that the target node is single, the genealogical graphing system 110 may not include the icon for inserting a child to the marriage 450F.

In some embodiments, the genealogical graphing system 110 can determine whether a specific node is associated with one or more succeeding nodes. As described, the enriched node format for a specific node includes data indicating the number of succeeding nodes for the member represented by that specific node. The term "number of succeeding nodes" is being used in this manner to refer to how many members in the memory 118 may have that specific node as a first preceding node in a genealogical graph. The genealogical graphing system 110 can, therefore, determine from the enriched node format, whether the target node is associated with any succeeding nodes and, in turn, whether to activate the icon for deleting the target 450C (i.e. to allow interaction).

Figure 23:
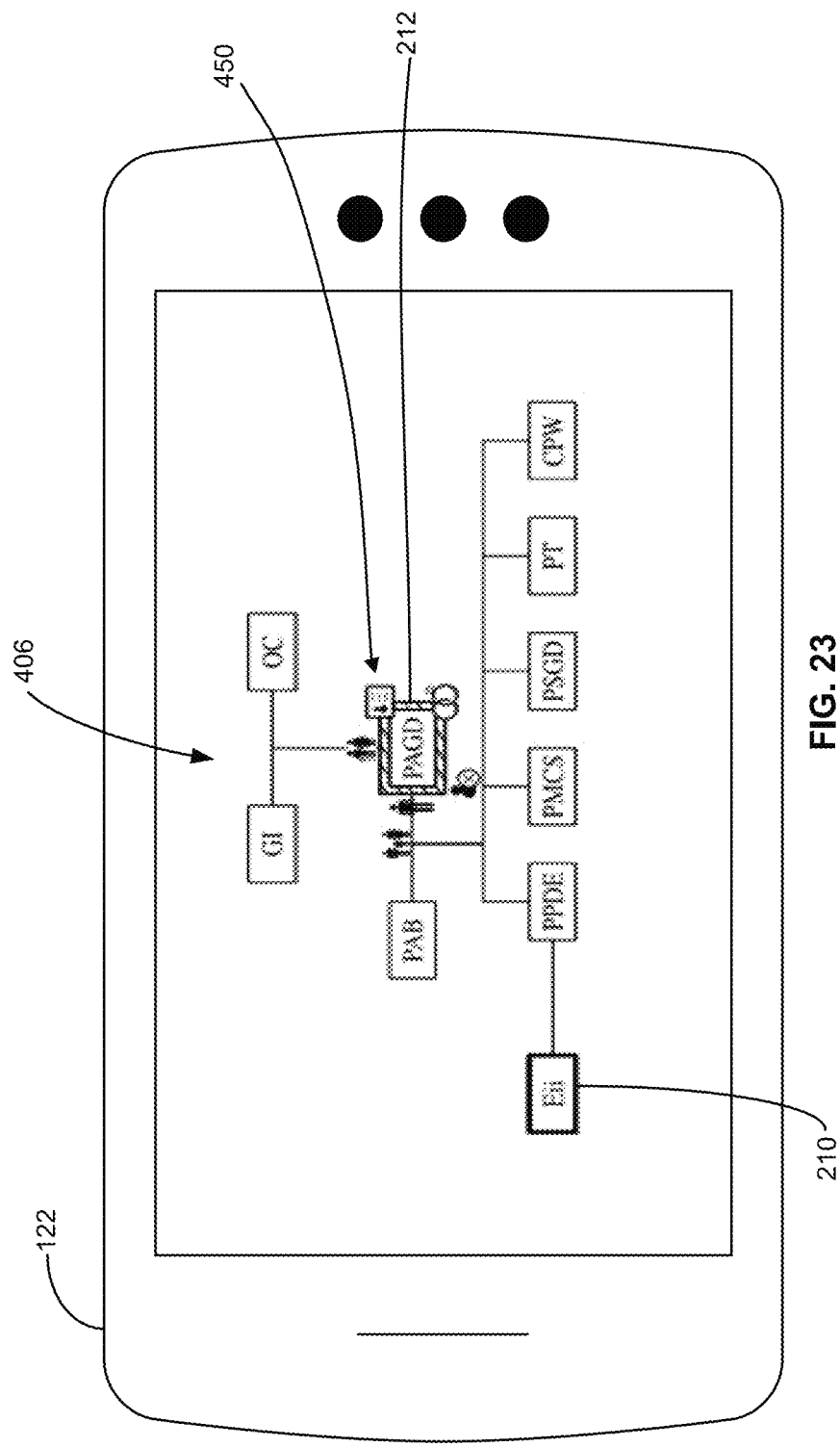
FIG. 23 shows another example genealogical graph following a user interaction received at the computing device of FIG. 20.

The genealogical system 110 may, in some embodiments, activate the icon for deleting the target 450C only when the target member does not have any succeeding nodes. In these embodiments, genealogical graphs 400, 402, 404, 406, 408, 410, 414, and 416 of FIGS. 20-25 and 27-28, respectively, would not have the icon for deleting the target 450C displayed since the respective target members of these genealogical graphs have succeeding nodes. The genealogical system 110 may ignore a delete-target node request (for e.g., from a hacker) when the target node has succeeding nodes. For example, a target member who is not married and does not have any children can be associated with the icon for deleting the target 450C. In this way, a genealogical graph can remain at all times a graph in which all nodes (i.e. members) are connected. Any target member (i.e. target node) can still be deleted; however, only after all succeeding members of the target member 212 have been previously deleted. For example, in the genealogical graph 412 of FIG. 26, PTD is a target node and has no succeeding nodes. Therefore, PTD can be deleted from the genealogical graph 412. In this case, PTD can be deleted because EADB will remain as a second parent and EADB will provide a path from the initial node to three children of the marriage. After receiving the delete-target node request, the genealogical system 110 makes the target node's first preceding node the new target. In the example described above, EADB is the first preceding node of the PTD and as result, EADB becomes the new target node once PTD is deleted from genealogical graph 412. When the genealogical graphing system 110 receives a user input indicating the target member 212 is now PAGD, the genealogical graphing system 110 generates the genealogical graph 406 with the set of editing icons 450 now being associated with the node for PAGD as shown in FIG. 23.

In some embodiments, a logged-in user is unable to delete their associated node. In other words, the user can delete all relatives, except for oneself. To delete oneself, the user must delete their user account, for example, on eveskids.com.

When the genealogical graphing system 110 receives user inputs associated with edits to the genealogical graphs, the genealogical graphing system 110, in some embodiments, can store the edits in the memory 118 prior to displaying the edited genealogical graph to the user. When the user relaunches the genealogical display system 110, they can then see the state of a genealogical family graph as they have left it.

In some embodiments, the target member 212 is displayed to the right of the initial member 210 in the genealogical graphs disclosed herein. For example, in FIG. 23, although target member 212 (PAGD) is the husband and his spouse PAB is the wife, target member 212 is displayed on the right/east side.

The full set of genealogical data, members and connections, can be stored by the genealogical graphing system 110 in the memory 118. For each genealogical graph, the genealogical graphing system 110 can, in some embodiments, retrieve from the memory 118, and store in the system memory 116, data for members in the genealogical graph (e.g., data related to the interior members forming a path from the initial member 210 to the target member 212) as well as data for individuals related to each member at a predefined degree. In some embodiments, the predefined degree can be different for certain members of a genealogical graph. For example, a predefined interior degree can be set for interior members and a different predefined degree, such as a predefined target degree, can be set for the target member 212. The predefined degree is a maximum degree of genealogical data to retrieve when generating a genealogical graph.

For example, the genealogical graphing system 110 can store in the system memory 116 data for the interior members that form the path from the initial member 210 to the target member 212 and data for individuals with a first-degree relationship to the interior members and data for individuals with a second-degree relationship to the target member 212. By retrieving data related to the members displayed in the genealogical graph but not used when generating the genealogical graph, the genealogical graphing system 110 can likely generate a new genealogical graph in response to a user input selecting one of the displayed nodes without needing to retrieve additional data from the memory 118. In this way, the genealogical graphing system 110 can likely generate the new genealogical graph with minimal delay, and avoid any lag which may result from a slow connection with the network 120 and/or the memory 118, for example. As the user, on computing device 122, selects additional nodes, computing device 122 can request additional data from the genealogical graphing system 110, but if the client program on computing device 122 finds that the user request can be satisfied without contacting the genealogical graphing system 110, no communication is initiated. Thus, computing device 122 can become self-sufficient. For some interactions between the user and the computing device 122, no communication with genealogical graphing system 110 may be initiated or needed.

In some embodiments, when the genealogical graphing system 110 generates interior node formats for the interior nodes of a genealogical graph, the genealogical graphing system 110 can retrieve data for the non-linking interior members also. However, when the genealogical graphing system 110 generates adjusted interior node formats for the interior nodes of a genealogical graph, the genealogical graphing system 110 does not display the non-linking interior members.

Reference is now made to FIGS. 29A to 30B, which show example schematics of various configurations of genealogical graphs that can be generated by the genealogical graphing system 110. The various configurations can vary with attributes of the display device, such as a size and/or resolution of the display screen, and other factors, such as design and style.

FIGS. 29A and 29B show schematics 500 and 502, respectively, for different configurations of genealogical graphs for showing a target member ("T") with multiple parents (e.g., biological parents, adoptive parents, foster parents, godparents, etc.). In FIG. 29A, the schematic 500 shows a first parent set 504 connected to the target member and a second parent set 506 aligned above the first parent set 504, but not connected to, the first parent set 504 or the target member. FIG. 29B shows the schematic 502, which is an alternative configuration for showing multiple parents of the target member. In the schematic 502, the second parent set 506 is aligned above the first parent set 504. Both the first and second parent sets 504, 506 are connected to the target member. The edge connecting the second parent set 506 to the target member intersects the edge between the parents of the first parent set 504.

FIGS. 30A and 30B show schematics 508 and 510, respectively, for different configurations of genealogical graphs for showing children from the same relationship.

In FIG. 30A, the schematic 508 shows a set of children 512 (child 512A, 512B, 512C and 512D) connected directly to a relationship line 514 connecting the parents. FIG. 30B shows schematic 510, which shows the set of children 512 directly connected to a link 516, and the link 516 connects the set of children 512 to the relationship line 514 connecting the parents. The configurations shown in FIGS. 30A and 30B are not limited to the number of children shown but can apply to two or more children.

Figure 31A:
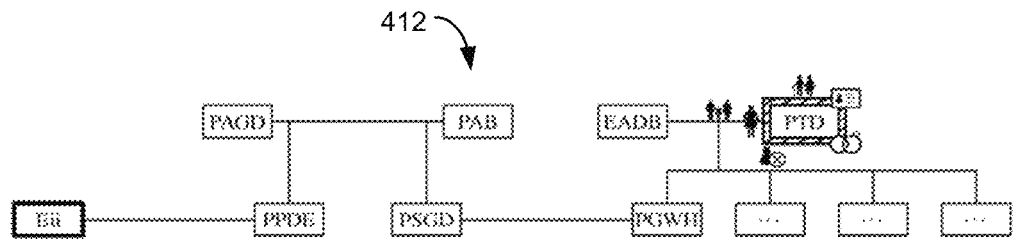
FIG. 31A shows a reproduction of the example genealogical graph of FIG. 26.
Figure 31B:
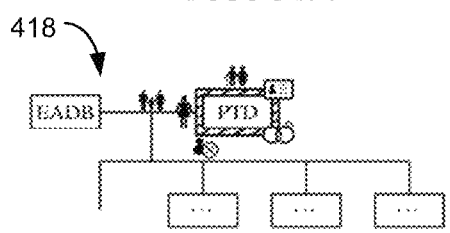
FIG. 31B shows a target node format of the example genealogical graph shown in FIG. 31A.
Figure 31C:
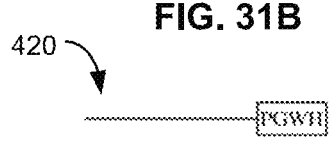
FIG. 31C shows an interior node format of the example genealogical graph shown in FIG. 31A.
Figure 31D:
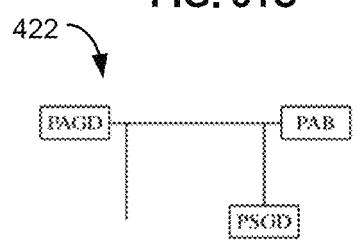
FIG. 31D shows another interior node format of the example genealogical graph shown in FIG. 31A.
Figure 31E:
FIG. 31E shows another interior node format of the example genealogical graph shown in FIG. 31A.
Figure 31F:
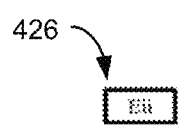
FIG. 31F shows an enriched node format of the example genealogical graph shown in FIG. 31A.
Figure 32A:
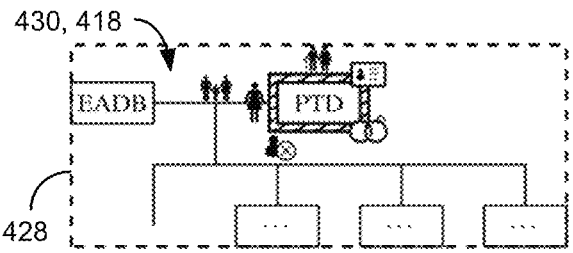
FIG. 32A shows a bounding box of a drawing list including the target node format shown in FIG. 31B.
Figure 32B:
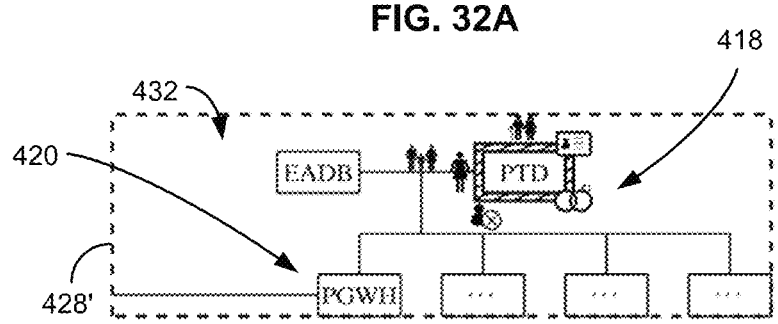
FIG. 32B shows the bounding box of FIG. 32A with the drawing list expanded to include the interior node format shown in FIG. 31C.
Figure 32C:
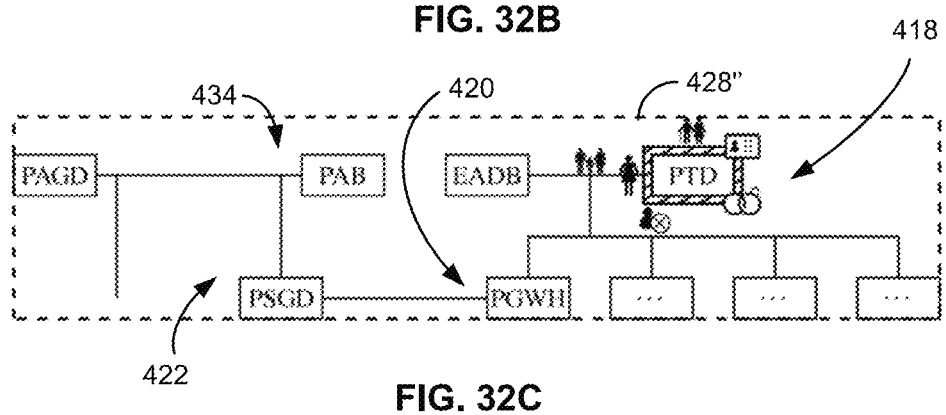
FIG. 32C shows the bounding box of FIG. 32B with the drawing list expanded to include the interior node format shown in FIG. 31D.
Figure 32D:
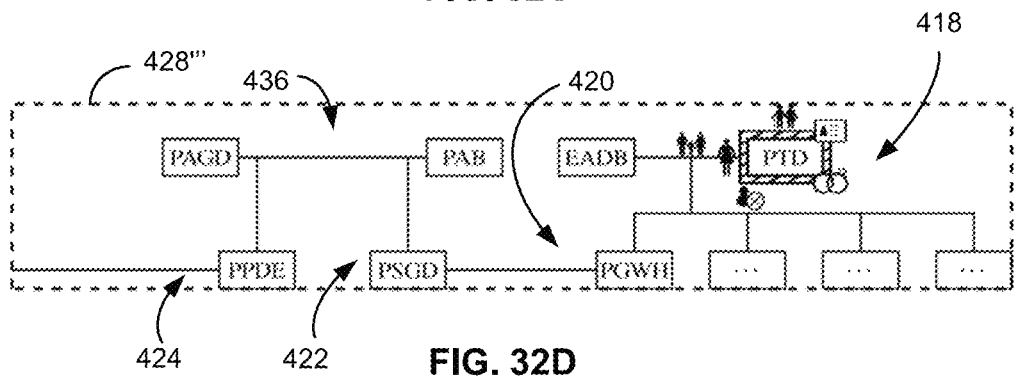
FIG. 32D shows the bounding box of FIG. 32C with the drawing list expanded to include the interior node format shown in FIG. 31E.
Figure 32E:
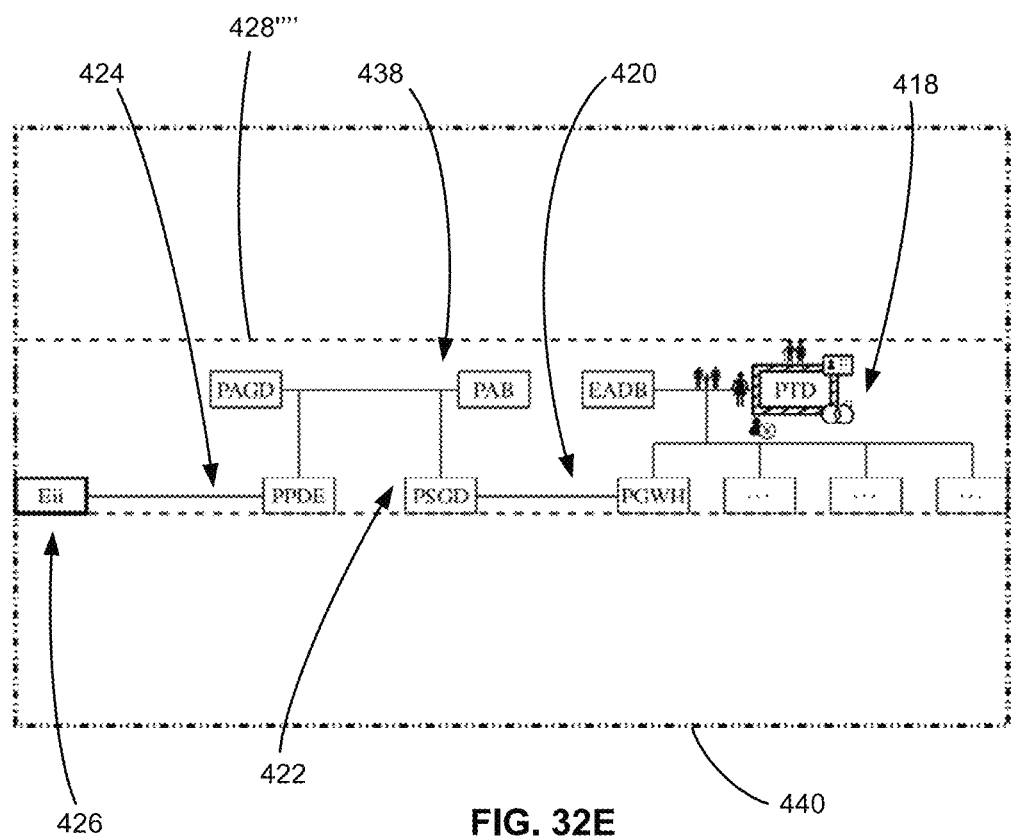
FIG. 32E shows the bounding box of FIG. 32D with the drawing list expanded to include the enriched node format shown in FIG. 31F.

Reference is now made to FIGS. 31A to 32E to illustrate, through an example, how the genealogical graphing system 110 uses bounding boxes to position a genealogical graph on the display of the computing device 122. FIG. 31A shows a reproduction of the genealogical graph 412 of FIG. 26 to serve as the example. The genealogical graph 412 includes five distinct node formats shown in FIGS. 31B to 31F, respectively. FIG. 31B shows a target node format 418 drawn for a target node PTD. FIG. 31C shows an interior node format 420 drawn for an interior node PGWH. FIG. 31D shows another interior node format 422 drawn for another interior node PSGD. The interior node format 422 of PSGD includes parents PAGD and PAD since the sequel pointer of PSGD is a sibling (i.e. PPDE) with shared parents. As discussed above, when the first preceding node is a parent (i.e. either PAB or PADG) and the second preceding node is a child (i.e. PPDE) of the first preceding node, the genealogical graphing system 110 can overwrite the sequel pointer that has been initialized to the first preceding node and set it to point to the second preceding node instead. FIG. 31E shows yet another interior node format 424 drawn for yet another interior node PPDE. FIG. 31F shows an enriched node format 426 drawn for an initial member Eii.

Before drawing, the genealogical graphing system 110 does not know the bounds of the genealogical graph 412 and may be unable to position the coordinate axis or set a scale of the genealogical graph 412 such that no part of the genealogical graph 412 lies outside the display. To determine the coordinate axes and the scale of genealogical graph 412, the genealogical graphing system 110 proceeds in the sequential steps illustrated in FIGS. 32A to 32E. First, a bounding box 428 is determined for drawing list 430 including only the target node format 418 of FIG. 31B (see FIG. 32A). Next, a bounding box 428' is determined for a drawing list 432 including both the interior node format 420 of FIG. 31C and the target node format 418 of FIG. 31B (see FIG. 32B). Next, a bounding box 428" is determined for a drawing list 434 cumulatively including the interior node format 422 of FIG. 31D, the interior node format 420 of FIG. 31C, and the target node format 418 of FIG. 31B (see FIG. 32C). Next, a bounding box 428''' is determined for a drawing list 436 cumulatively including the interior node format 424 of FIG. 31E, the interior node format 422 of FIG. 31D, the interior node format 420 of FIG. 31C, and the target node format 418 of FIG. 31B (see FIG. 32D). Lastly, a bounding box 428'''' is determined for a drawing list 438 cumulatively including the enriched node format 426 of FIG. 31F, the interior node format 424 of FIG. 31E, the interior node format 422 of FIG. 31D, the interior node format 420 of FIG. 31C, and the target node format 418 of FIG. 31B (see FIG. 32E).

Figure 26:
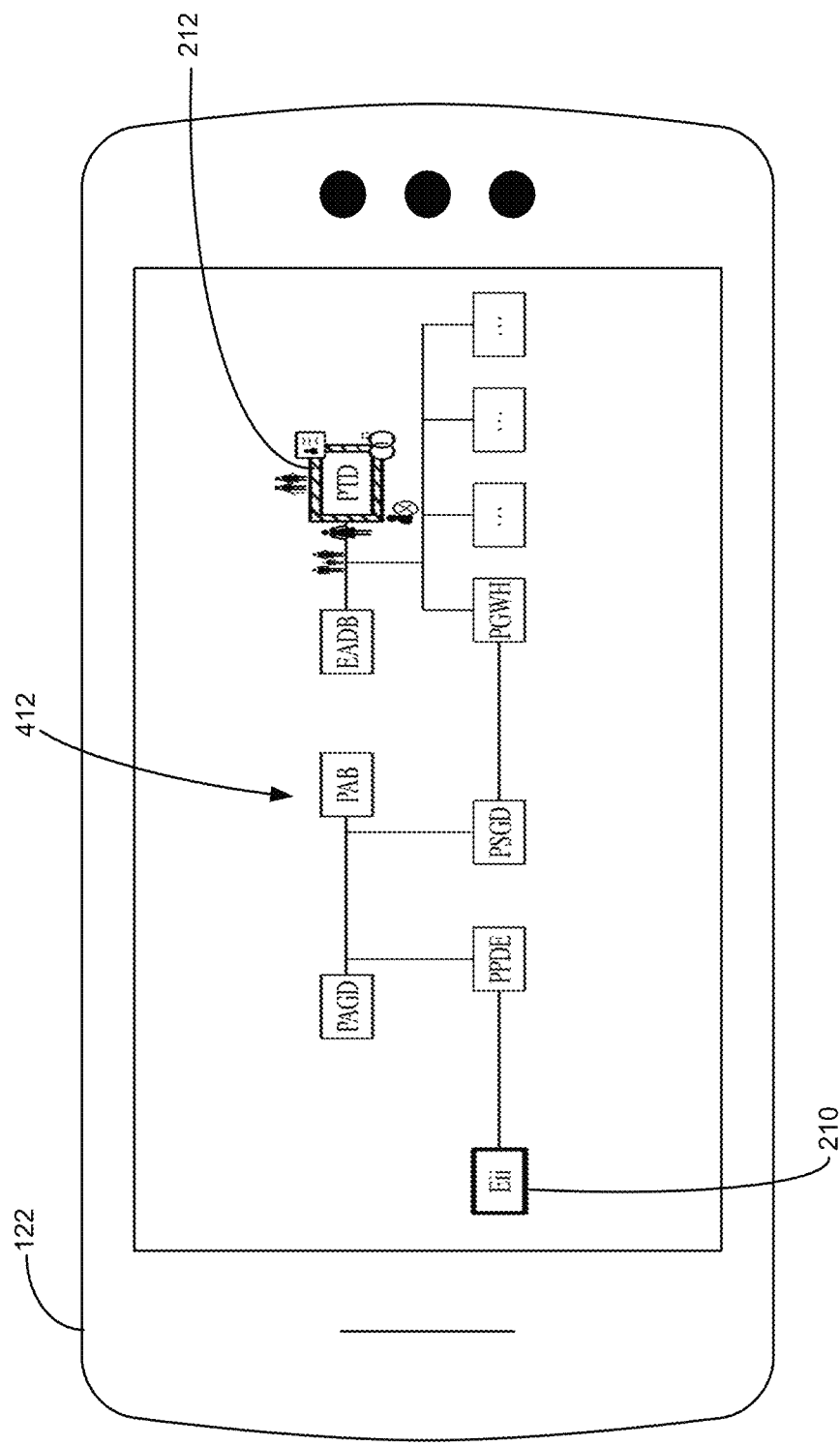
FIG. 26 shows another example genealogical graph following a user interaction received at the computing device of FIG. 25.
Figure 27:
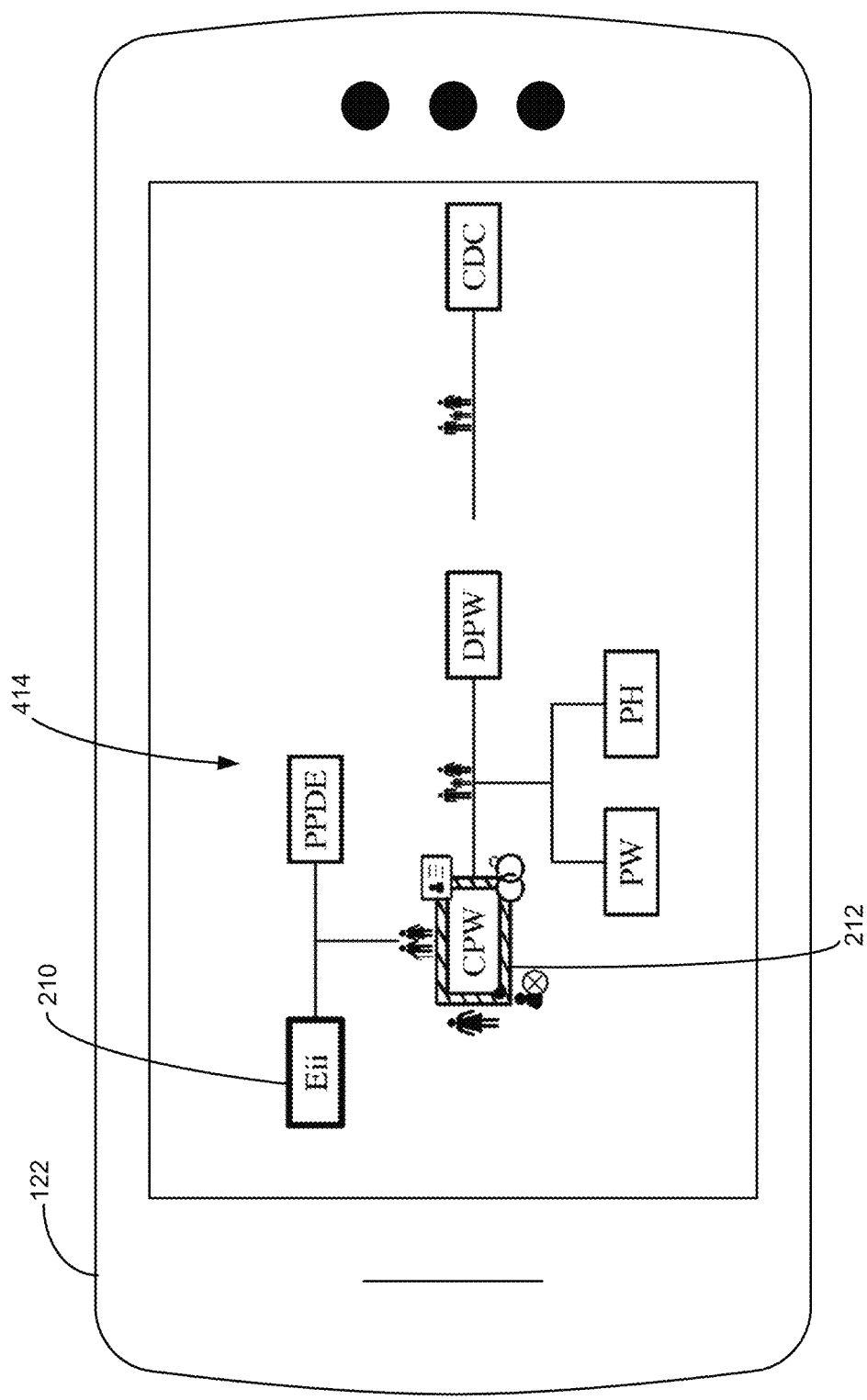
FIG. 27 shows another example genealogical graph following a user interaction received at the computing device of FIG. 20.
Figure 28:
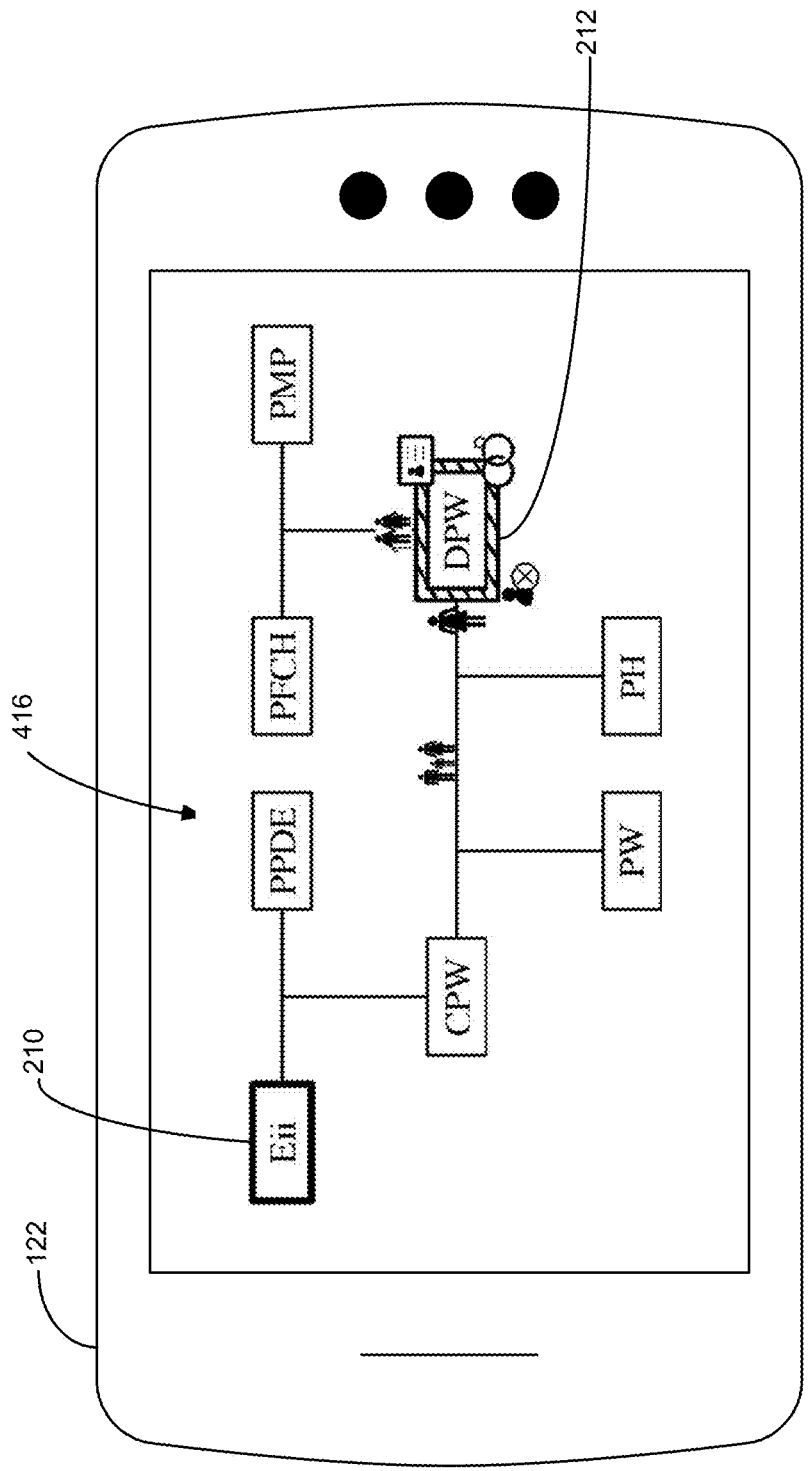
FIG. 28 shows another example genealogical graph following a user interaction received at the computing device of FIG. 27.

The bounding box 428'''' represents the final bounding box. The genealogical graphing system 110 can position the final bounding box 428'''' of the drawing list 438 in the center of a display 440 of computing device 122 as shown in FIG. 26. The genealogical graph 412 within the drawing list 438 can now be drawn on the display 440 with the knowledge that no part will lie outside the display 440 of the computing device 122. Through the use of bounding boxes, the genealogical graphing system 110 can determine where a respective genealogical graph will land before starting the actual drawing process. This makes it possible to set the origin of the coordinate axes and the scale of the respective genealogical graph such that the genealogical graph will be within the visible display.

In some embodiments, the genealogical graphing system 110 can provide a path selection user interface for facilitating selection of other related members for analysis. The path selection user interface can include icons that can be selected by the user for varying the target member and/or the initial member in the genealogical graph.

Figure 33A:
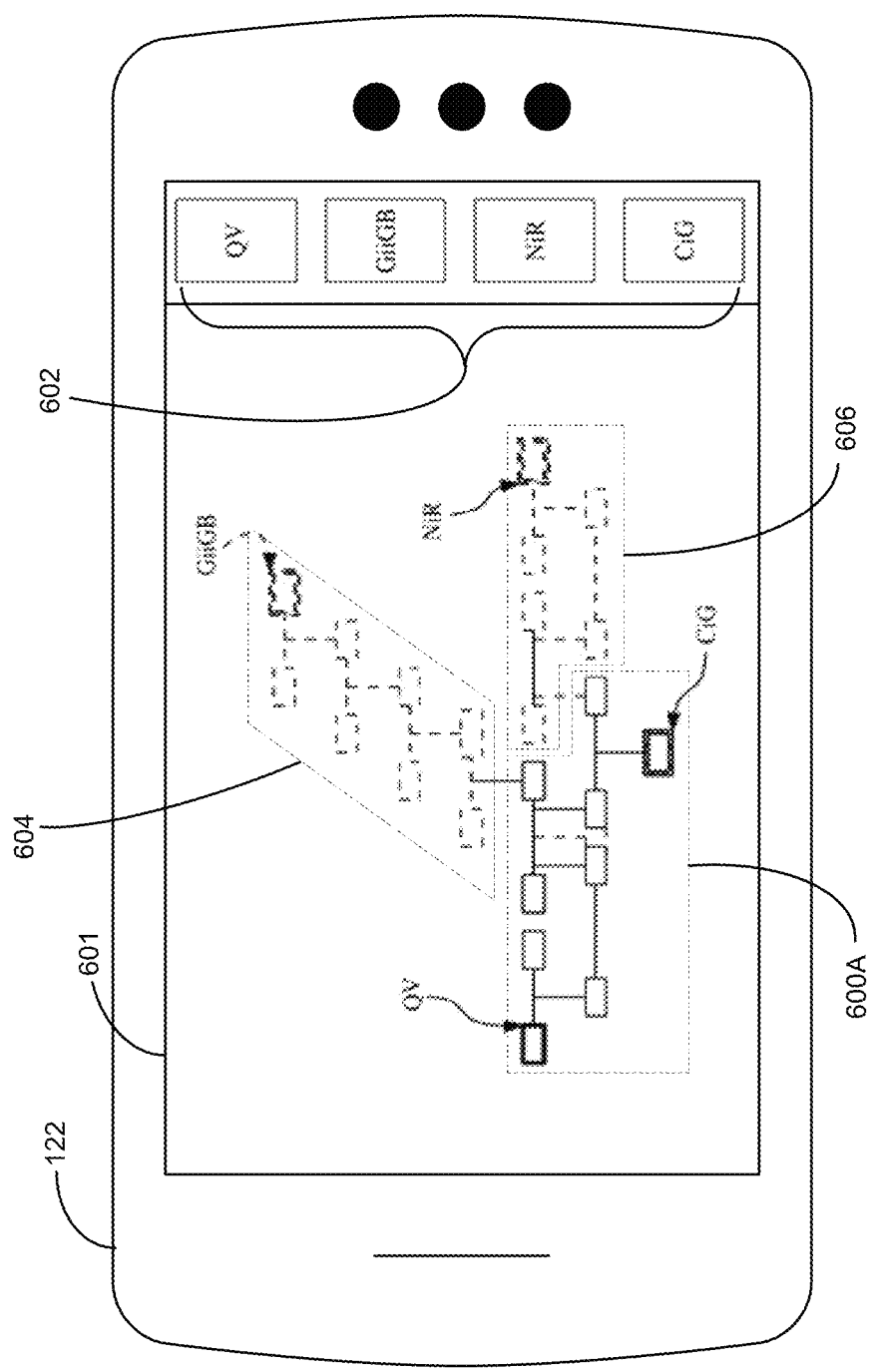
FIG. 33A shows a path selection user interface displayed at a display screen of an example computing device, in accordance with an embodiment.

FIG. 33A shows a path selection user interface 601 displayed at a display screen of the computing device 212. The path selection user interface 601 shows a genealogical graph 600A that includes a path from an initial member QV (Queen Victoria) to a target member CiG (King Constantine I), and a set of path selection icons 602 for a subset of relatives for QV and CiG. In the illustrated example, the set of path selection icons 602 include an icon for QV, GiiGB (King George II), NiR (Tsar Nicholas), and CiG. Fewer or more path selection icons 602 can be included in various embodiments. In some embodiments, the set of path selection icons 602 can show the most recent relatives the user has visited (i.e. a history of previous genealogical graphs). In this way, the set of path selection icons 602 can enable the user to navigate quickly to a node they had recently visited. In the illustrated example, the set of path selection icons 602 is a scrollable vertical list positioned on the right hand side of the path selection user interface 601. However, it will be appreciated that the set of path selection icons 602 may have an alternative configuration and position.

FIG. 33A shows the various paths 604, 606 that can be generated when the set of path selection icons 602 is selected. In some embodiments, these paths 604, 606 may not be displayed until the corresponding path selection icon is selected.

Figure 33B:
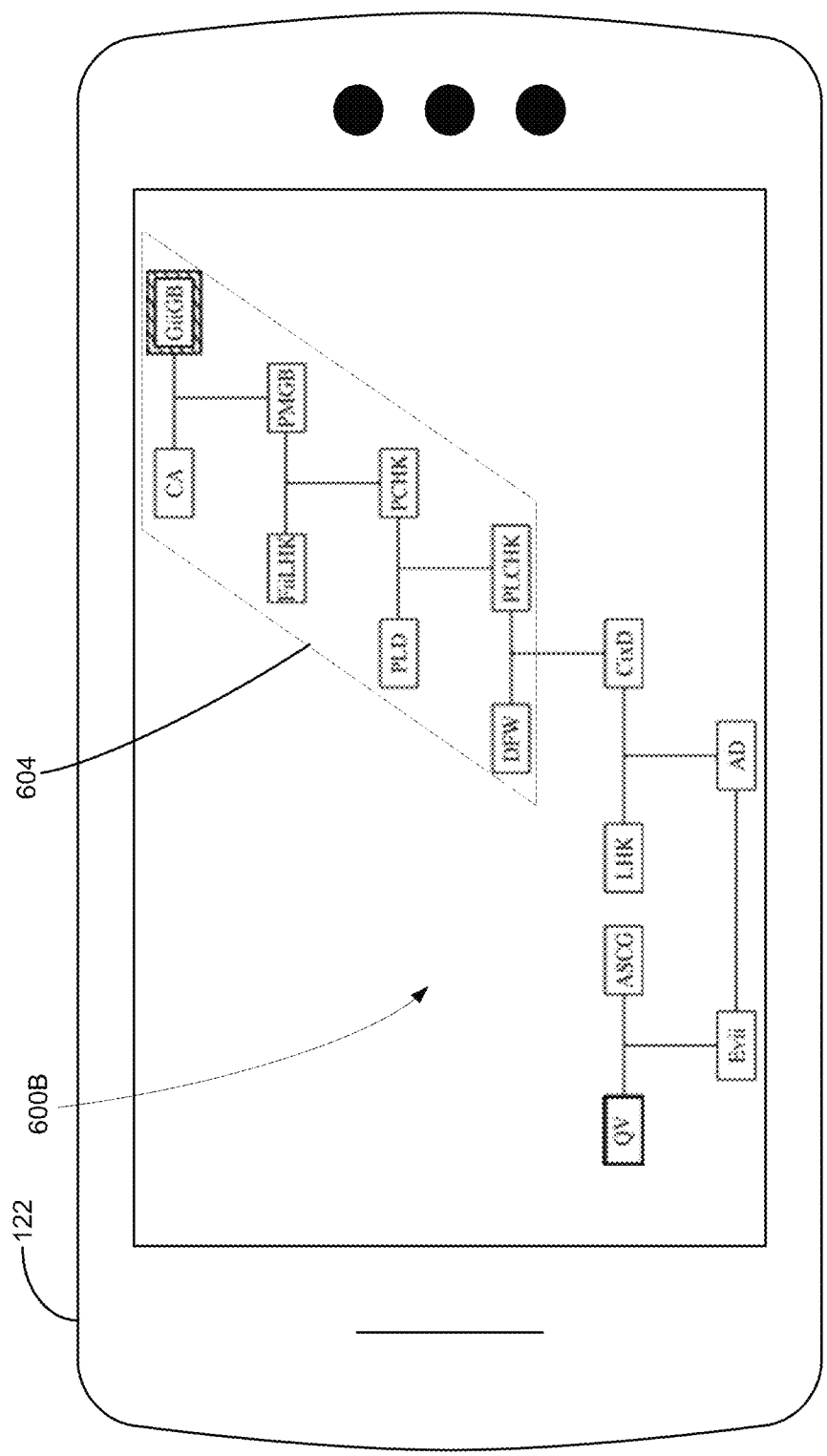
FIG. 33B shows an example genealogical graph following a user input received at the path selection user interface of FIG. 33A.
Figure 33C:
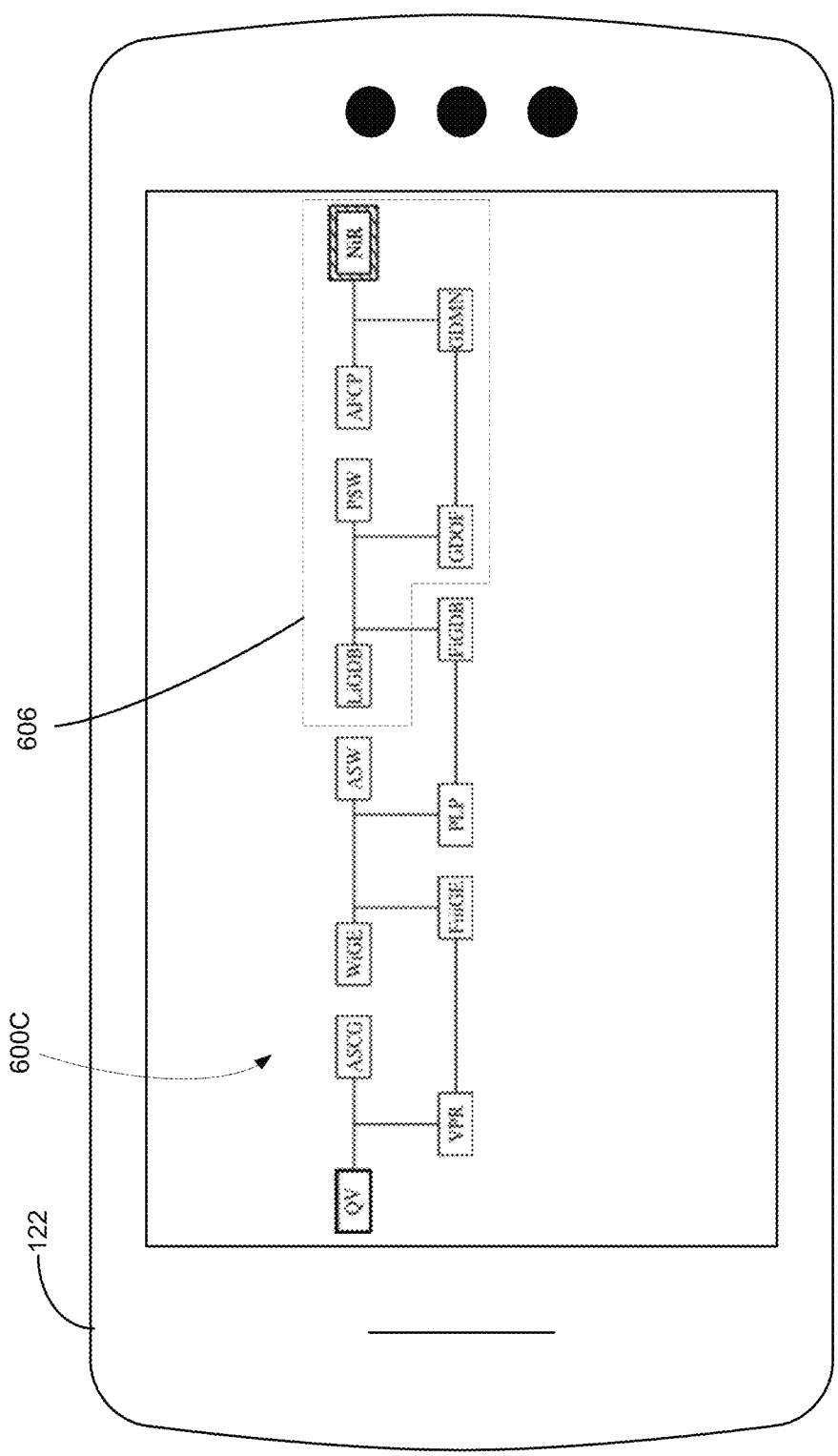
FIG. 33C shows another example genealogical graph following a user input received at the path selection user interface FIG. 33A.
Figure 33D:
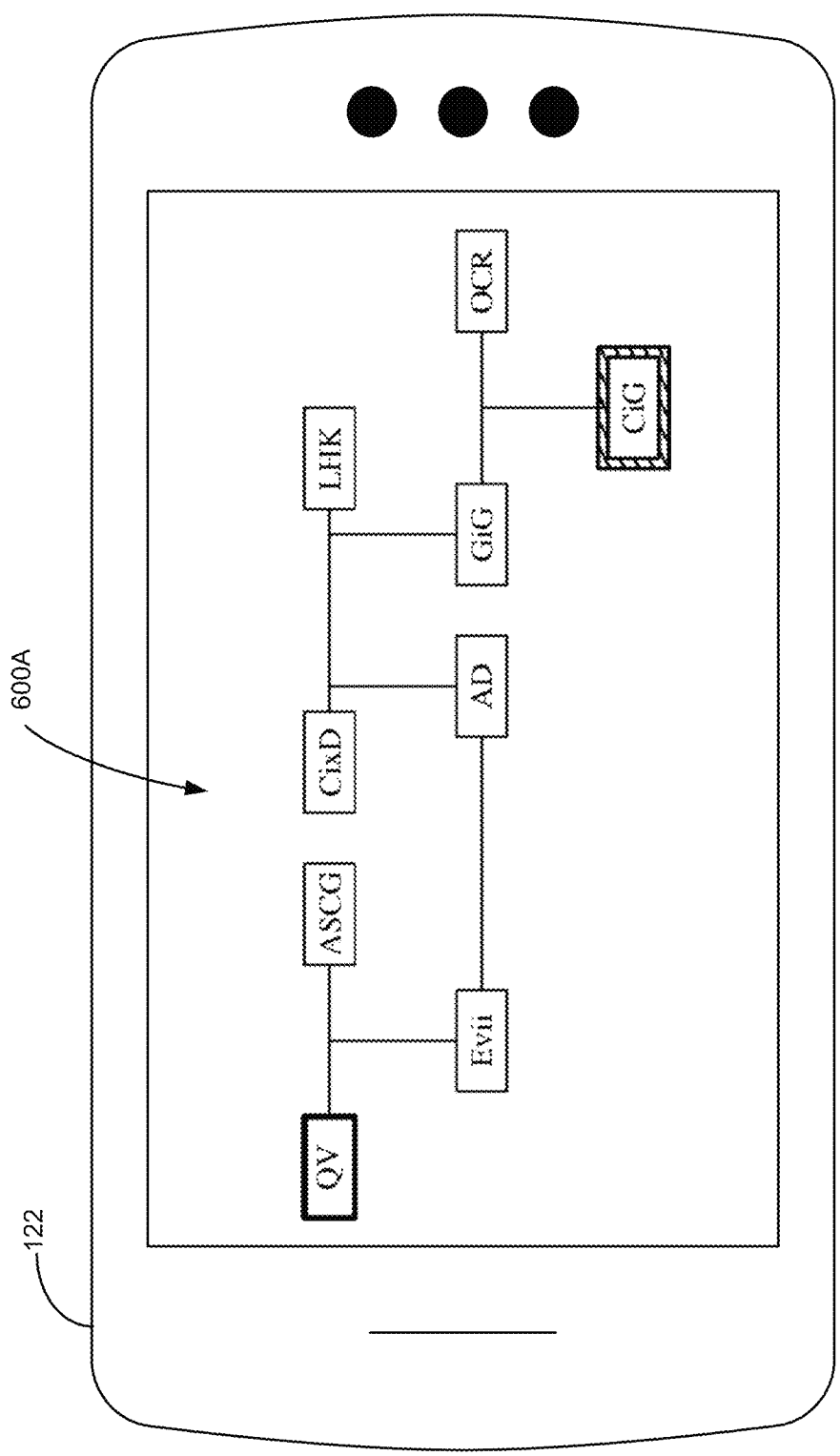
FIG. 33D shows another example genealogical graph following a user input received at the path selection user interface FIG. 33A.

The genealogical graph 600A includes the path from QV to CiG (see FIG. 33D). When the path selection icon associated with GiiGB is selected, the genealogical graphing system 110 can generate an updated genealogical graph that includes the relevant portions of the genealogical graph 600A and the path 604 shown in dashed lines. When the path selection icon associated with NiR is selected, the genealogical graphing system 110 can generate an updated genealogical graph that includes the relevant portions of the genealogical graph 600A and the path 606 shown in dashed lines.

When a path selection icon of the set of path selection icons 602 is selected, the genealogical graphing system 110 receives a path selection input indicating the path selection icon is selected and in response, the genealogical graphing system 110 updates the currently displayed genealogical graph based on the selected path selection icon. For example, the genealogical graphing system 110 can receive the path selection input indicating that the path selection icon associated with GiiGB is selected. In response, the genealogical graphing system 110 can generate a genealogical graph 600B that shows a path from QV to GiiGB, such as the genealogical graph shown in FIG. 33B.

When the genealogical graphing system 110 receives a path selection input indicating that the path selection icon associated with NiR is selected, the genealogical graphing system 110 can generate a genealogical graph 600C that shows a path from QV to NiR, such as the genealogical graph shown in FIG. 33C.

Figure 34A:
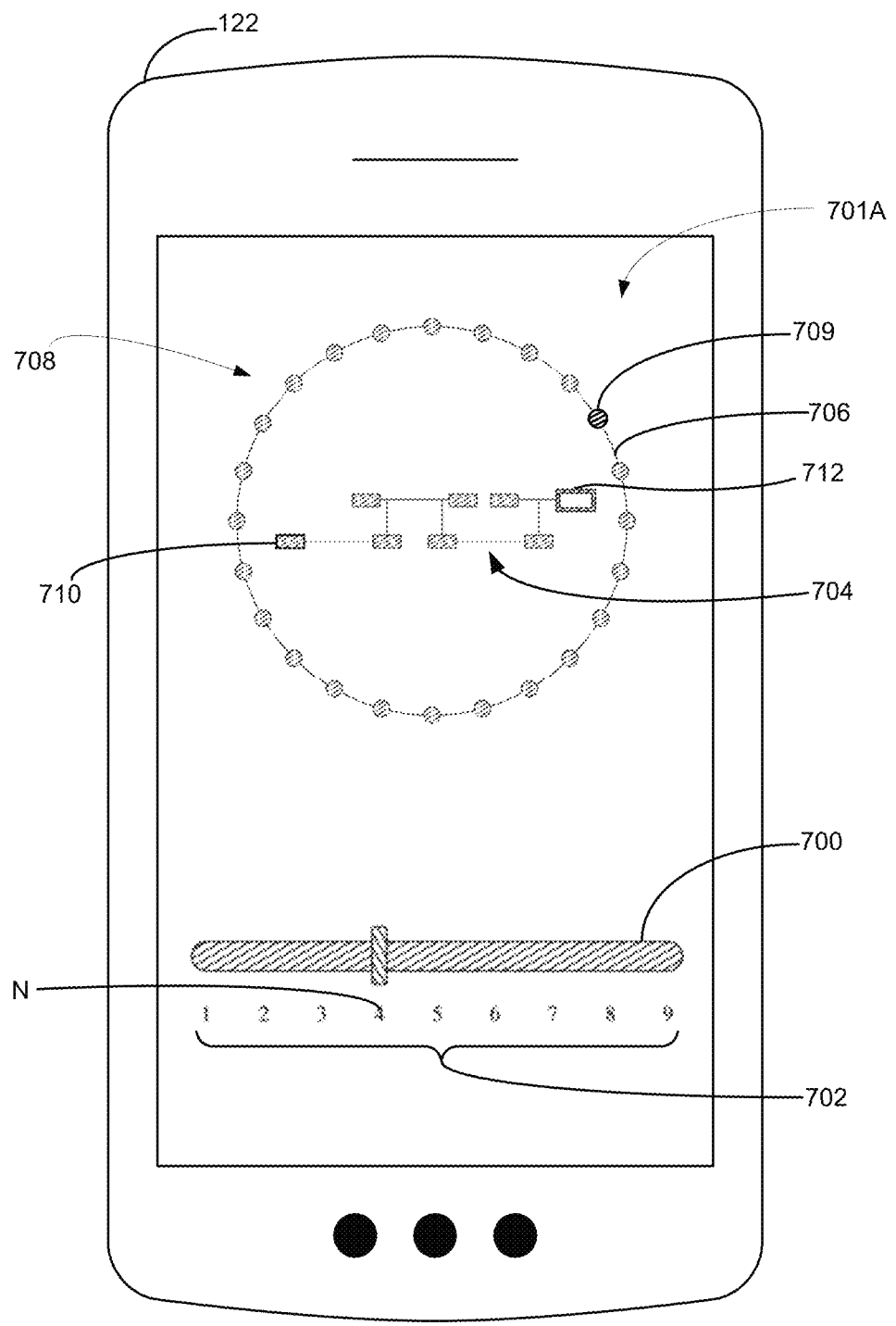
FIG. 34A shows a path selection user interface displayed at a display screen of an example computing device, in accordance with an example embodiment.
Figure 34B:
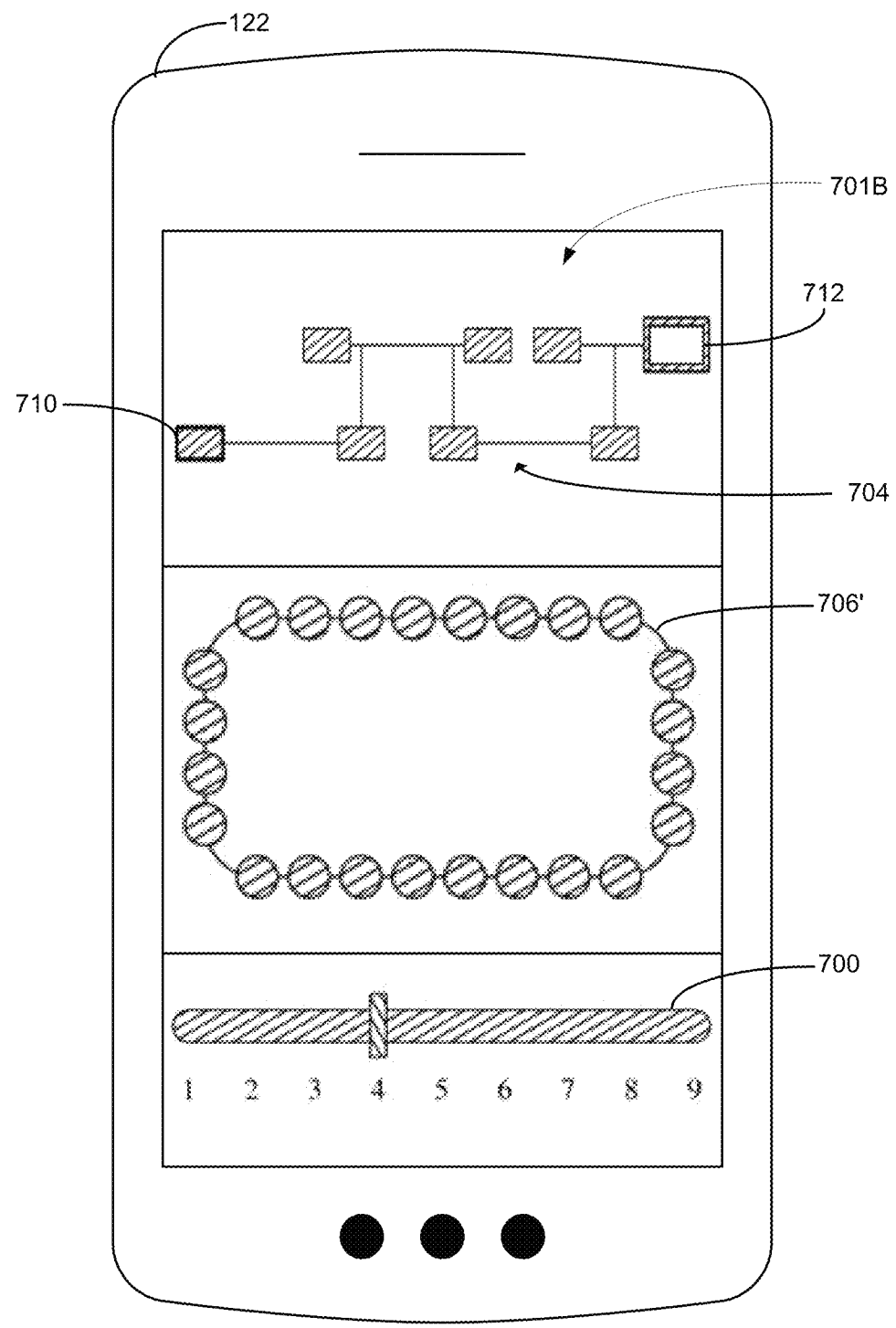
FIG. 34B shows another path selection user interface displayed at a display screen of an example computing device, in accordance with another example embodiment.

FIGS. 34A and 34B show example path selection user interfaces 701A and 701B, respectively.

In FIG. 34A, the path selection user interface 701A includes an example genealogical graph 704 and a set of path selection icons 708. In this embodiment, the set of path selection icons 708 are arranged in a generally circular configuration 706 that surround the genealogical graph 704. Other configurations may similarly be used for arranging the set of path selection icons 708, such as, for example, rectangular configuration, a configuration including a set of concentric circles, etc.

The set of path selection icons 708 includes members related to an initial member 710 in the genealogical graph 704. The individuals shown in the set of path selection icons 708 can include all relatives within a predefined degree. The predefined degree "N" can be adjusted by the user or be set by default by the genealogical graphing system 110. In the path selection user interface 701A, a slider 700 with a series of integers 702 is shown. The slider 700 can be adjusted for the purpose of varying the predefined degree in this example. In this illustrated example, the predefined degree is "4" and so, the genealogical graphing system 110 includes in the set of path selection icons 708 all relatives of the initial member 710 at four degrees.

In some embodiments, each path selection icon 708 can show an image of the individual being represented.

When the genealogical graphing system 110 receives an input indicating a path selection icon is selected, the genealogical graphing system 110 generates a genealogical graph that shows a path from the initial member 710 to the member associated with the selected path selection icon (i.e. a new target member).

Referring still to FIG. 34A, the set of path selection icons can be sorted around the generally circular configuration 706 in an order corresponding to a set of vectors from the initial member 710 to the target member 712 on the corresponding genealogical graph 704. The set of vectors in this case are not computed with the objective of displaying the genealogical graph 704. Instead, the set of vectors can be computed for determining the order of the path selection icons 708 around the generally circular configuration 706. For example, a unit north-west vector can be used for traversing from the initial member 710 to a father of the initial member 710. A unit north-east vector can be used for traversing from the initial member 710 to a mother of the initial member 710. For an in-law, a unit vector directed either east or west from the initial member 710 can be used, in whichever direction the preceding vector was already set. The children are assigned unit vectors equally spaced in the lower half of the generally circular configuration 706, with the first child to the west-south-west and the last child to the east-south-east. Each unit vector is converted to an angle between −180.000 degree and +179.000 degrees. The unit vectors are sorted along a circle and the icons are equally distributed along the circle in their respective order.

FIG. 34B shows another example path selection user interface 701B. The path selection user interface 701B includes the example genealogical graph 704 of FIG. 34A. Unlike the configuration 706 shown in FIG. 34A, the set of path selection icons 708 are in a generally rectangular configuration 706' and does not surround the genealogical graph 704.

Figure 35A:
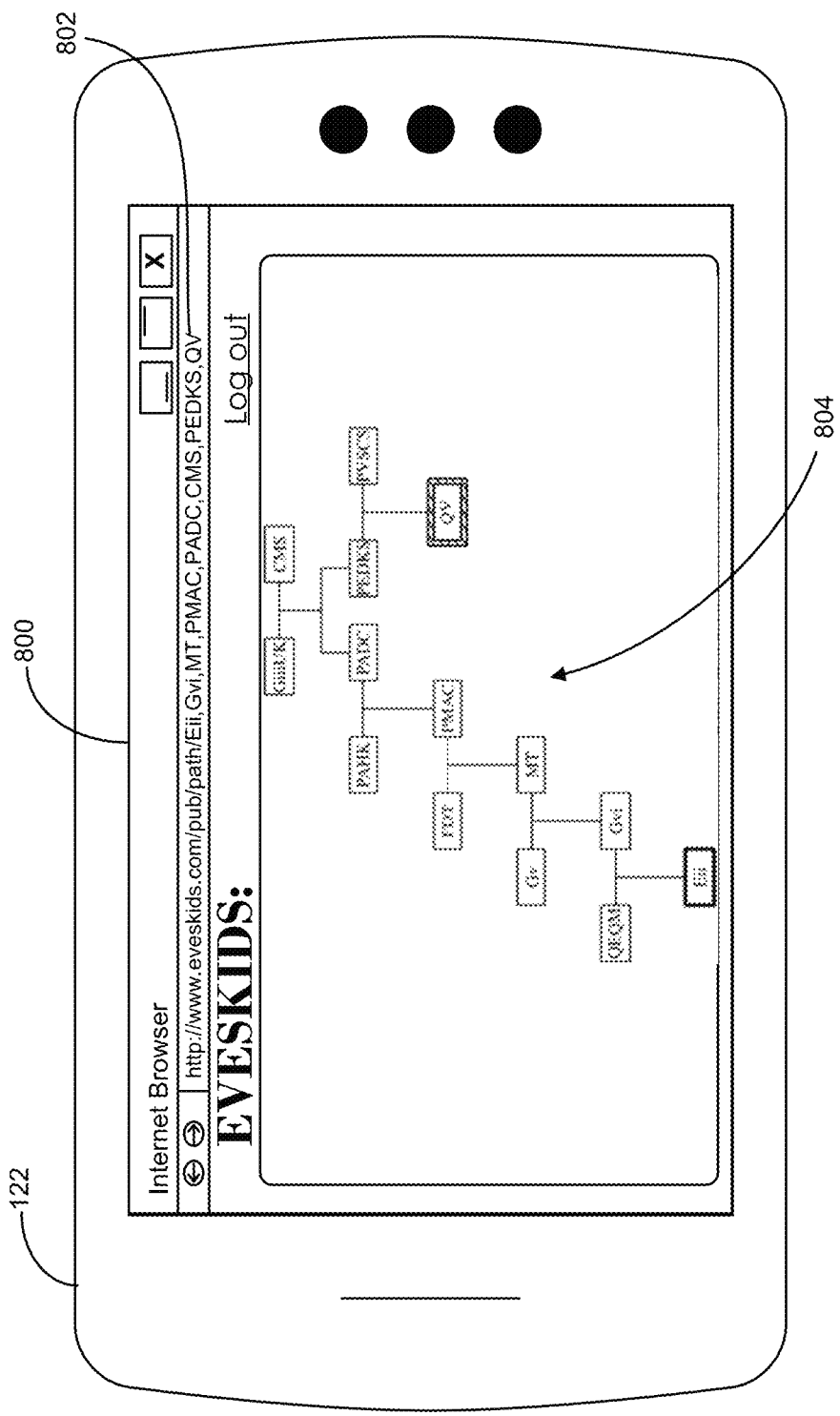
FIG. 35A shows a web browser interface displaying an example genealogical graph in accordance with an example embodiment.
Figure 35B:
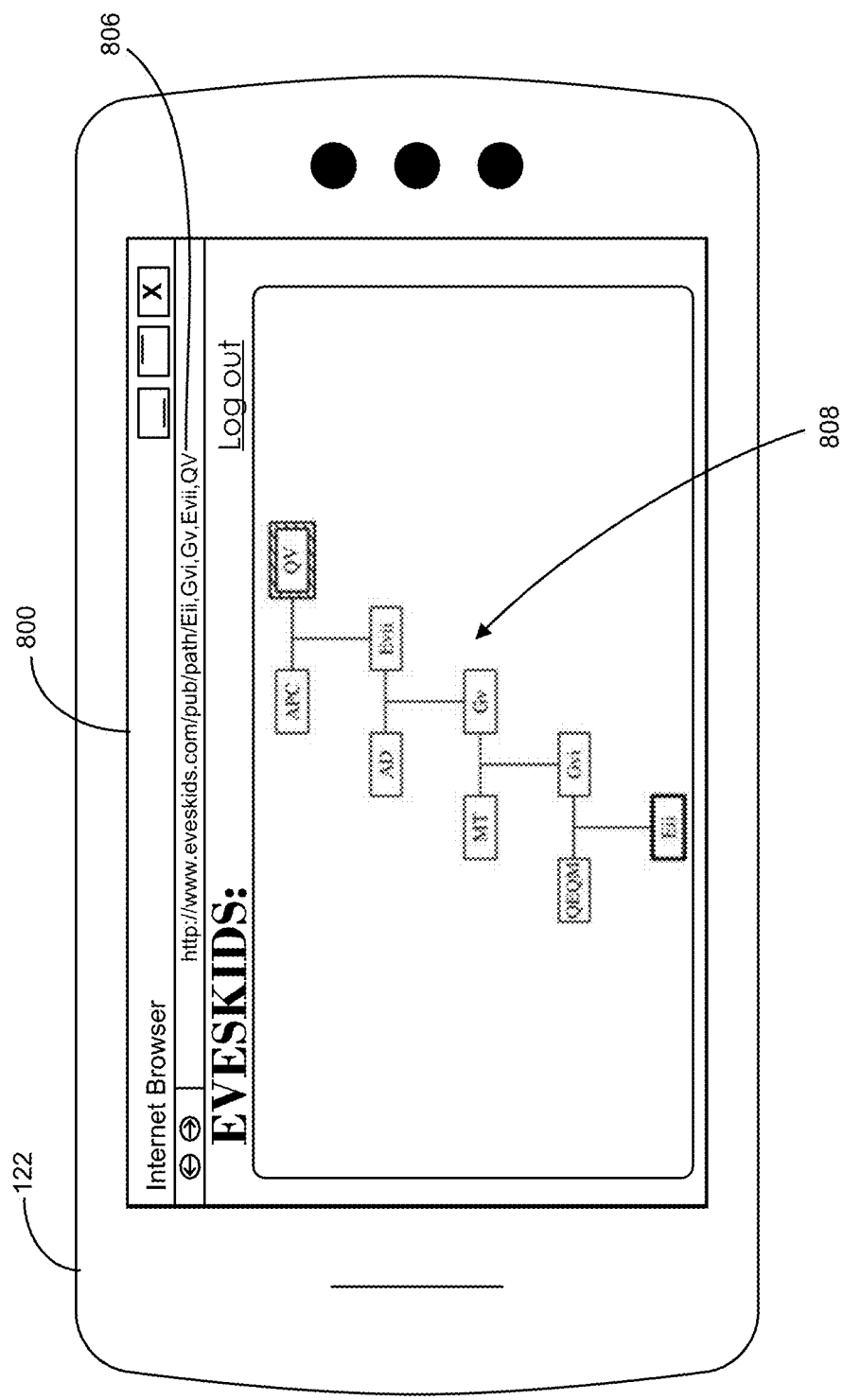
FIG. 35B shows a web browser interface displaying another example genealogical graph in accordance with an example embodiment.
Figure 35C:
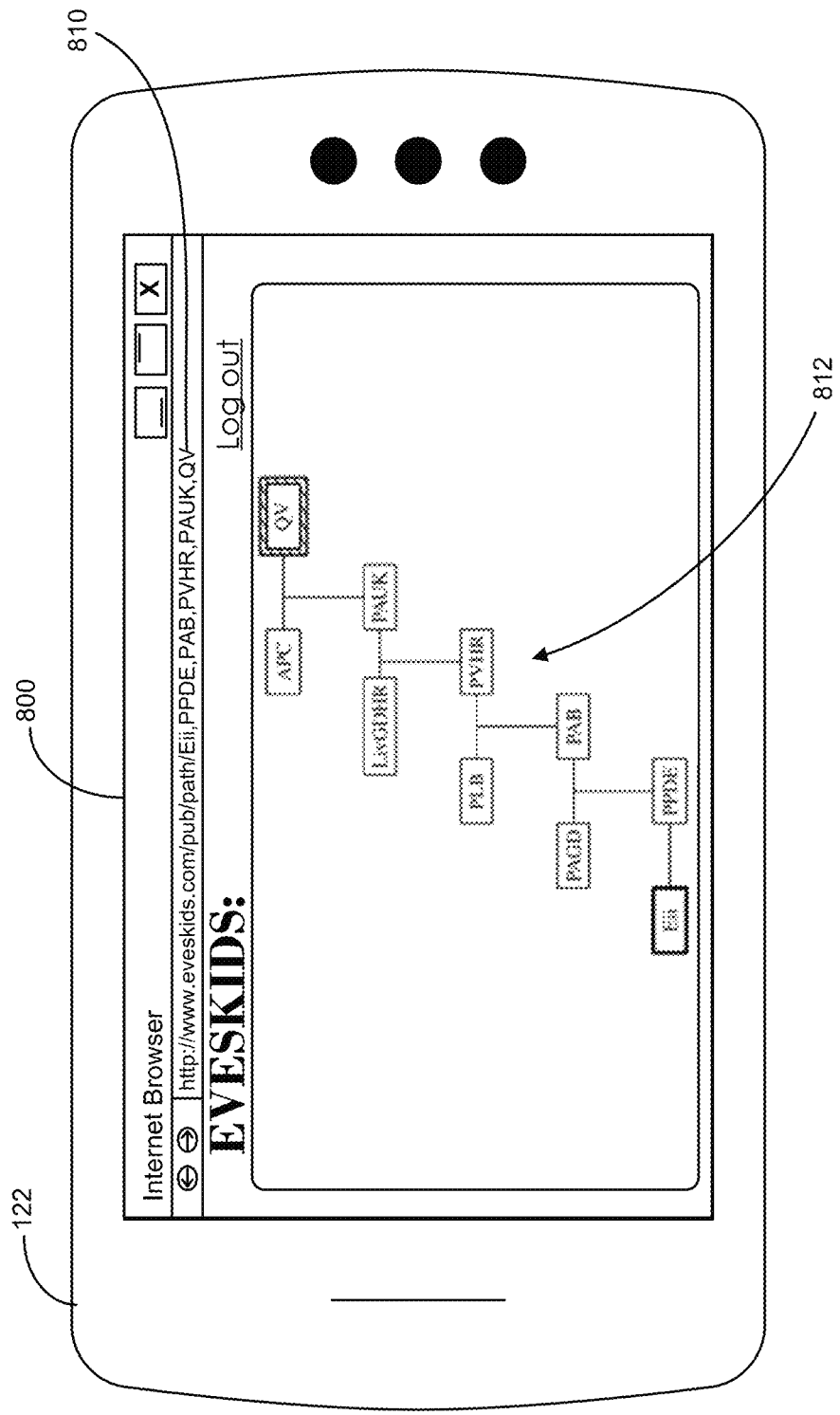
FIG. 35C shows a web browser interface displaying another example genealogical graph in accordance with an example embodiment.

In some embodiments, the genealogical graphing system 110 can generate multiple different paths between an initial member and a target member as the initial member and the target member can be related in different ways. FIGS. 35A to 35C show example paths between Eii (Queen Elizabeth II) and Qv (Queen Victoria).

FIG. 35A shows a web browser interface 800 displayed via a display screen of the computing device 122. The web browser interface 800 shows a genealogical graph 804. The genealogical graph 804 shows a first path between the initial member, Queen Elizabeth (Eii), and the target member, Queen Victoria (QV). This first path is represented also in the illustrated Uniform Resource Locator (URL) 802. FIG. 35B shows a genealogical graph 808 illustrating a second path between Eii and QV. This second path is represented also in the illustrated URL 806. FIG. 35C shows a genealogical graph 812 illustrating a third path between Eii and Qv, which is represented by the URL 810

The linking members of the genealogical graphs 804, 808, and 812 are embedded in the respective URLs 802, 806 and 810. The example URLs 802, 806 and 810 lists the linking members in the order of appearance within the genealogical graph separated by commas. Other listing formats can similarly be used for generating the respective URLs. For example, the short forms can be replaced with other unique identifiers for the respective individuals, and/or another separation can be used instead of the comma.

In some embodiments, a user can bookmark the URL to retrieve the associated genealogical graph. For a pairing of an initial member and a target member with multiple paths, the user can bookmark each of the URLs for the various paths to retrieve those genealogical graphs.

FIGS. 36A and 36B show example abbreviated address paths 902, 904, respectively. In these example abbreviated address paths 902, 904, a semicolon separates an initial member and a target member, and the semicolon can act as a wild card.

The genealogical graphing system 110 can, in response to receiving the abbreviated address paths 902, 904 generate a genealogical graph with a path from an initial member to a target member that includes all possible paths between the initial member and the target member. Some or all of the interior members can be omitted from the abbreviated address paths 902, 904. In some embodiments, as shown in the abbreviated address path 902, one or more interior members (e.g., Gvi and Gv) can be listed after the initial member (e.g., Eii) and before the semicolon. The initial member and the listed interior members can be referred to as an initial member set. The listed connection members can help to define the path from the initial member to the target member. Similarly, an abbreviated address path can include a target member set following the wild card (e.g., semicolon). The target member set can include the target member immediately following the wild card and one or more other members that are being requested to be shown in the genealogical graph.

In response to the abbreviated address path 902, the genealogical graphing system 110 can be triggered to generate a genealogical graph in which Eii is the initial member, Gvi and Gv are included in the path, and QV is the target member. In abbreviated address path 902, Gvi and GV are the interior members and QV is the target member. In this way, by entering the abbreviated address path 902, the genealogical graphing system 110 can generate all possible paths between Eii and QV that pass through Gvi and GV.

In response to the abbreviated address path 904, the genealogical graphing system 110 can be triggered to generate a genealogical graph in which Eii is the initial member, and QV is the target member. In this way, the abbreviated address path 904 can return all paths between Eii and QV.

When the genealogical graphing system 110 detects a semicolon in the address path, the genealogical graphing system 110 can perform a breadth-first search from both the initial member (or initial member set) and the target member (or target member set) that surround the semicolon. The breadth-first search can progress in tandem from both the initial member and target member until a common relative is found. The search can abort after a preset depth of the search, in which case the user can be notified that no connecting path could be found. Although the examples shown to describe the abbreviated path feature use commas and semicolons, other distinct typographic elements can be used.

In some embodiments, the genealogical graphing system 110 may generate genealogical graphs for display via an application. In these embodiments, the URL may not be visible to the user in contrast to when the genealogical graphs are displayed via a web browser. In these embodiments, the genealogical graphing system 110 can generate a path address representing the path shown in the genealogical graph and store that path address in the memory 118. The genealogical graphing system 110 can convert that path address to a URL when required. In some embodiments, the genealogical graphing system 110 can store the path address as a URL.

The URLs 802, 806, 810, 902 and 904 of FIGS. 35A-36B, respectively, include "pub/path" to indicate that the path being shown consists of public nodes. Similarly, a path consisting of private nodes would have a URL with "priv/path". In an alternative embodiment, the public/private node distinction can be embedded within the node identifiers of the URL. For example node identifies that begin with "@" are public, and node identifiers that start with "@" and consist of six unicode characters or fewer are reserved for historical figures. For example, the URL "https://eveskids.com/L/@Eii,@Gvi", would display a genealogical graph linking public nodes Eii and Gvi. Also, in this example URL, "path" has been shortened to "L" (for "linkages", "lineage", or simply "line"). Similarly, the URL "https://eveskids.com/L/John,Doe" is private with John Doe serving as both the initial and target node. That is, any name absent "@" at the beginning of the node indentifier is considered a private node. In this example, John Doe may be the logged-in user. This alternative embodiment may provide for cleaner URLs.

Figure 37:
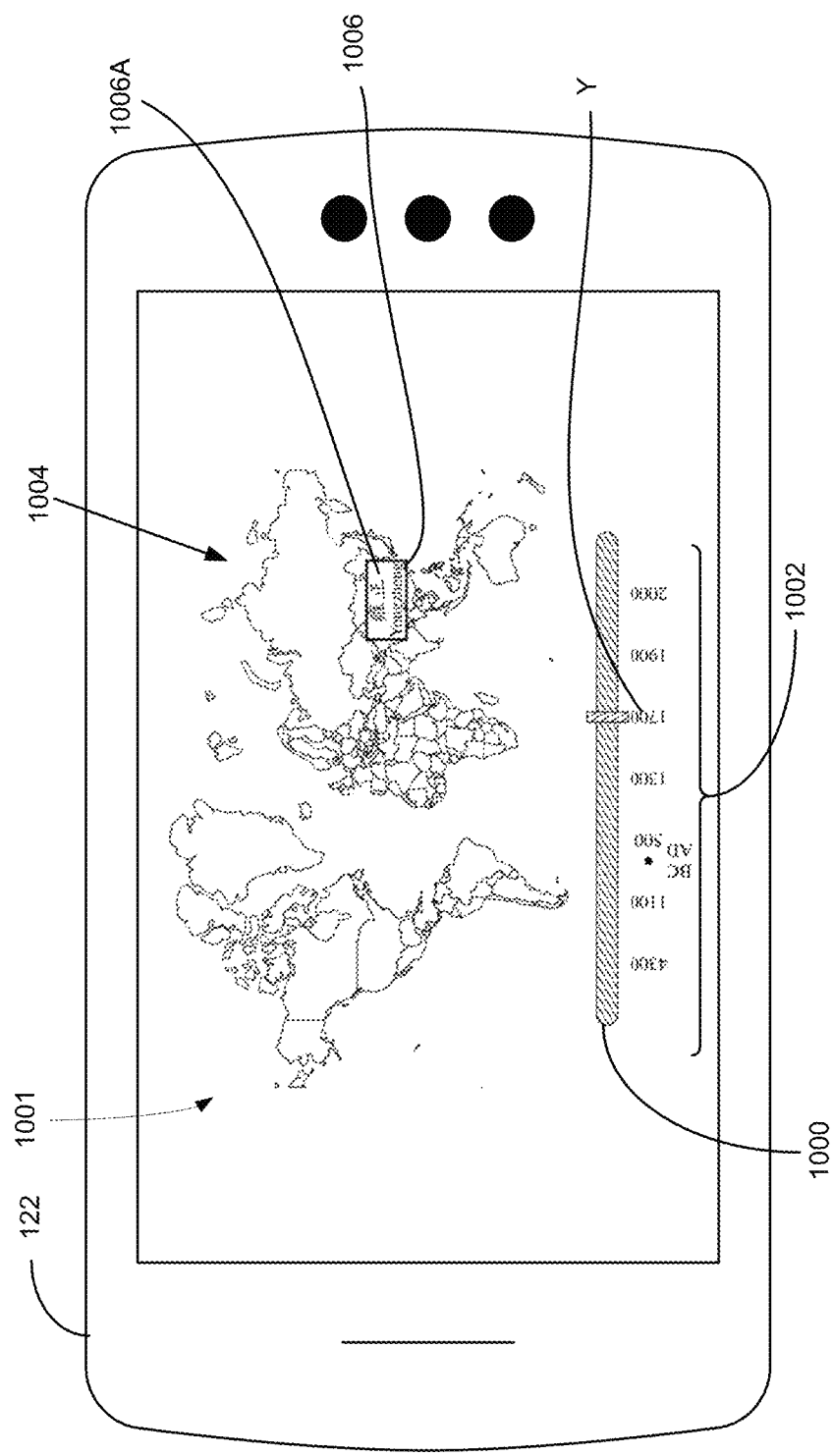
FIG. 37 shows a map discovery interface, in accordance with an embodiment.

FIG. 37 shows a map discovery interface 1001 via a display screen of the computing device 122. The map discovery interface 1001 can be generated by the genealogical graphing system 110 to provide an interactive discovery tool for the user.

The map discovery interface 1001 includes a world map 1004 and a slider 1000 with a range of years 1002 adjustable to vary a year or years being discovered. Depending on the discovery intention, the range of years 1002 can begin from the start of recorded civilization, specifically the inception of royal houses, and can continue until present day. Other discovery periods can be used.

In response to adjustment at the slider 1000, the genealogical graphing system 110 can display the relevant historical data on the world map 1004. Example historical data can include information about the birth and death dates of historical monarchs and their extended families. For example, in response to a selection of the year 1700, as shown in FIG. 37, the genealogical graphing system 110 can generate a historical member icon 1006 at the region of the world map 1004 corresponding to that historical member. The historical member icon 1006 can show when the historical member was born, lived, ruled, or died in the selected year at the corresponding region.

The historical member icon 1006 can include a name of the historical member, such as 1006A shown in FIG. 37, an image of the historical member (not shown), and/or information related to their reign and/or realm.

In some embodiments, the genealogical graphing system 110 can generate a genealogical graph for a historical member in response to receiving an input indicating a selection of the historical member icon 1006. The genealogical graph can be generated with the historical member as both an initial member and a target member.

In some embodiments, the genealogical graphing system 110 can generate genealogical graphs for individuals identified from an image. The genealogical graphing system 110 can retrieve data from public databases as well as private databases, as well as to genealogical graphs that are semi-private and semi-public.

When the genealogical graphing system 110 receives the images from the user, the genealogical graphing system 110 can allow the user to decide whether to share the images with all relatives within N-degree. In some embodiments, the genealogical graphing system 110 can automatically share the images with individuals who share an ancestor in one of the photographs, or can automatically request permission from the user providing the image(s) to share the image(s) with those individuals.

Figure 38B:
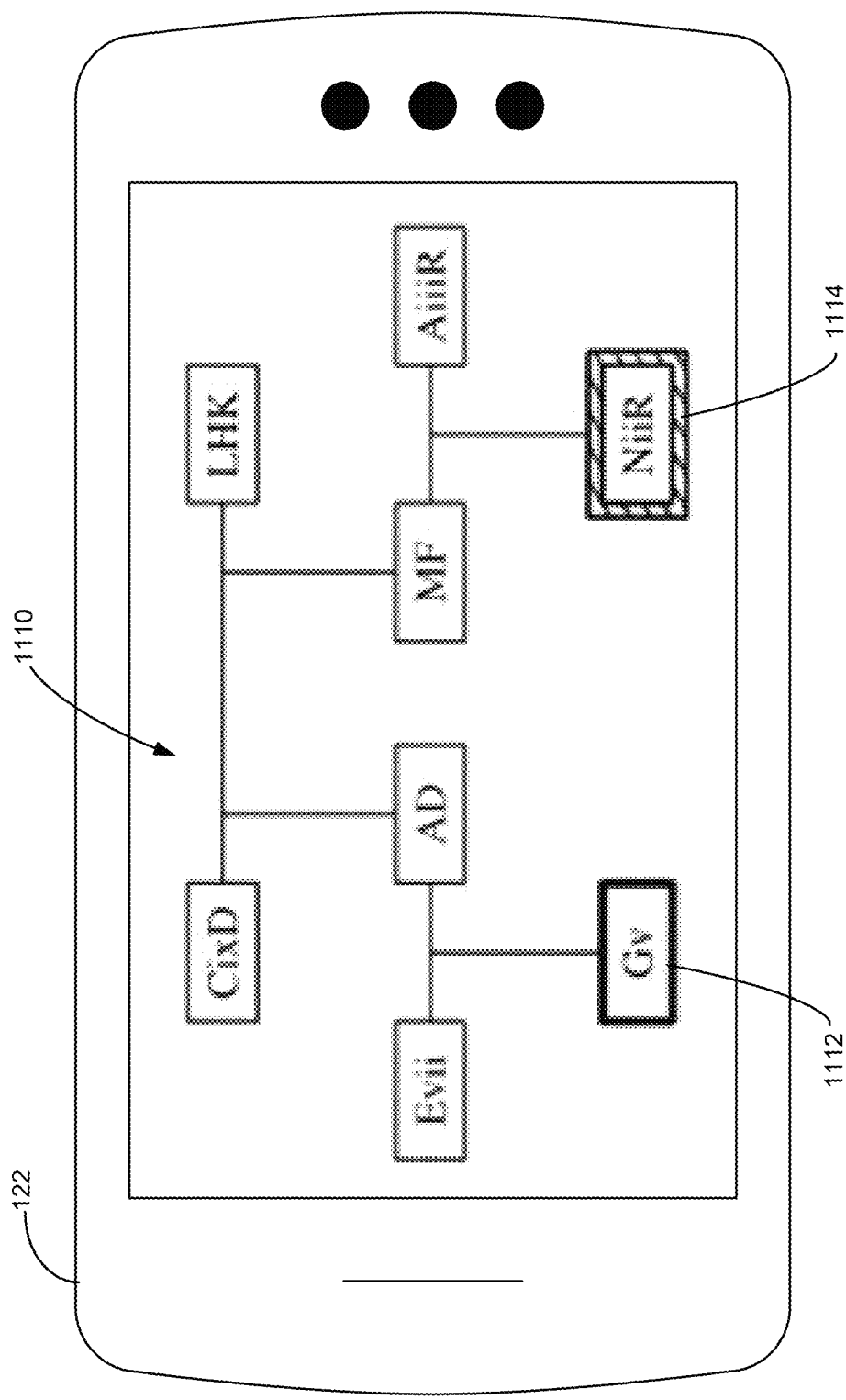
FIG. 38B shows an example genealogical graph generated as a result of interacting with the interactive image interface of FIG. 38A, in accordance with an example embodiment.

For example, FIG. 38A shows an interactive image interface 1100 via a display screen of the computing device 112. The interactive image interface 1100 includes an image of individuals 1102 and 1104. The individuals 1102 and 1104 are selectable via the interactive image interface 1100. The boxes 1006 represent that the individuals are selectable for analysis. Markers other than the boxes 1006 can be used, such as a different shading, and/or graphics (e.g., flashing, etc.).

Although only two individuals 1102, 1104 are shown in FIG. 38A, the interactive image interface 1100 can show images displaying fewer or more individuals.

As shown in FIG. 38A, the genealogical graphing system 110 can receive via the interactive image interface 1100 a selection of individual(s) for analysis. In FIG. 38A, a connector 1108 is drawn by the user from the individual 1102 to the individual 1104. In response to receiving the data related to the drawn connector 1108, the genealogical graphing system 110 can generate a genealogical graph showing a relationship between the individual 1102 to the individual 1104. In embodiments when multiple paths are determined, the genealogical graphing system 110 can display the shortest path or a list of the known paths from which the user can select a path for display.

For example, the individual 1102 can be King George V and the individual 1104 can be Tsar Nicholas II. From historical databases, the genealogical graphing system 110 can determine that King George V and Tsar Nicholas II are cousins. In response to receiving the data related to the drawn connector 1108, the genealogical graphing system 110 can generate the genealogical graph 1110 shown in FIG. 38B in which an initial member 1112 is King George V (Gv) and a target member 1114 is Tsar Nicholas II (NiiR).

In some embodiments, only one individual may be selected from the image in the interactive image interface 1100. The genealogical graphing system 110 can then generate a genealogical graph in which the user interacting with the interactive image interface 1100 is an initial member and the selected individual is a target member. In another embodiment in which only one individual is selected from the image, the genealogical graphing system 110 can generate a genealogical graph in which the selected individual is an initial member and a target member.

In some embodiments, the genealogical graphing system 110 can receive a selection of individuals for analysis via multiple images.

In some embodiments, the genealogical graphing system 110 can apply facial recognition techniques to the image to facilitate selection of the individuals 1102, 1104. In some embodiments, the genealogical graphing system 110 can prompt the user to identify the individuals in the image.

In some embodiments, the genealogical graphing system 110 can automatically generate a genealogical graph for individuals based on their physical proximity. The individuals 1200, 1202 (shown in FIG. 39) can be attendees at an event, such as a wedding, for example. The individuals 1200, 1202 may be members of an extended family, share an ancestor or be blood relatives via an N-th degree connection.

Prior to the event, the hosts, such as the bride and groom, could generate user profiles for their guests so that the guests can discovery each other's genealogical connections during and/or after the event. The data related to each guest can be entered into a private database. Data related to non-attending guests can also be entered for completeness. Example data for each guest can include user information, such as name, etc., and contact information, such as a phone number, an email address, etc.

The genealogical graphing system 110 may then be triggered to send system access information to the users informing them on how to access the genealogical graphing system 110, such as through a mobile application or a web application. Each recipient can be informed that the mobile application or the web browser can generate a genealogical graph for them and a guest they encounter at the event.

For example, at any time during the wedding, a guest can be invited or prompted to position their respective computing device back-to-back with the computing device of another guest. Alternatively, two guests wishing to understand their new connection can also do so by scanning, using the camera on the mobile phone of one of the two guests, a unique Quick Response (QR) code shown on the display of the mobile phone of the other guest. The genealogical graphing mobile applications can trigger a request to the genealogical graphing system 110 to generate a genealogical graph. The genealogical graphing system 110 can respond by displaying a genealogical graph showing a path from one guest to the other. The path displayed by the genealogical graphing system 110 may include the bride and groom. For example, if two guests meet, both from the side of the bride, their path may not include the groom. Alternatively, if two relatives, one from side of the bride and one from the side of the groom, have a common ancestor, such a path can be displayed, in addition to, or instead of the path between the bride and the groom. The two relatives can have a path through a common ancestor if the bride and groom are N-degree cousins, for example. The described methods and systems enable automatic discovery of the relationship, if any.

Figure 39:
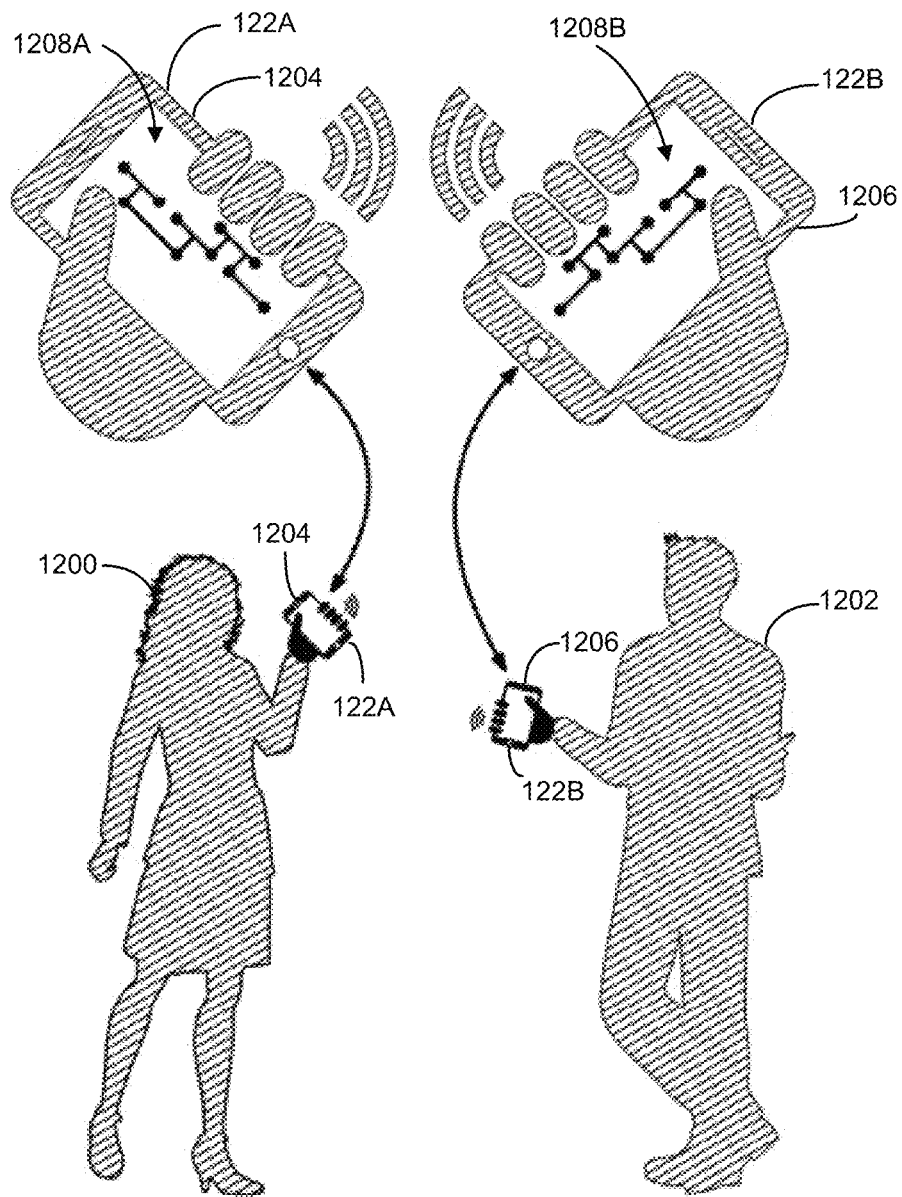
FIG. 39 shows an interaction between two individuals triggering an automatic generation of a genealogical graph, in accordance with an embodiment.

FIG. 39, for example, shows two individuals 1200, 1202 within a proximity threshold. The proximity threshold can be a minimum distance between the individuals 1200, 1202 to trigger the generation of the genealogical graph.

Each individual 1200, 1202 is a respective user of a computing device 122A, 122B. A genealogical graphing application installed at each of the computing devices 122A, 122B can detect whether another computing device is within a proximity threshold. For example, the computing device 122A can detect that the computing device 122B is within the proximity threshold. In response, the genealogical graphing system 110 can be triggered by one or both the computing devices 122A, 122B to generate a genealogical graph for the individuals 1200, 1202. For the individual 1200, the genealogical graph 1208A can be generated with the individual 1200 as an initial member and the individual 1202 as a target member. For the individual 1202, the genealogical graph 1208B can be generated with the individual 1202 as an initial member and the individual 1200 as a target member.

When the genealogical graphing system 110 determines the relationship between the individuals 1200, 1202, the genealogical graphing system 110 can display the genealogical graph illustrating the relationship via the display screen of the respective computing devices 122A, 122B. In the case that no relationship can be determined between the individuals 1200, 1202, the genealogical graphing system 110 can generate a distinct genealogical graph for each of the individual 1200 and 1202 in which each individual 1220 and 1202 is both an initial member and a target member in their respective genealogical graph.

In an example, when the computing device 122A detects that the computing device 122B is within the proximity threshold, the computing device 122A can transmit a connection request to the computing device 122B. If the response from the computing device 122B accepts the connection request, either the computing device 122B and/or the computing device 122A can transmit a graph generation request to the genealogical graphing system 110. The connection request can include an identifier corresponding to the user of the computing device 122A and the response to the connection request can include an identifier corresponding to the user of the computing device 122B.

In another example, when the computing device 122A detects that the computing device 122B is within the proximity threshold, the genealogical graphing system 110 can be automatically triggered to generate a genealogical graph 1208A and 1208B for the users of the computing devices 122A and 122B, respectively, and automatically display the resulting genealogical graph 1208A, 1208B, if any, at the respective display screens.

The computing devices 122A, 122B can detect the proximity threshold via various location-based technologies, such as Bluetooth™, Near Field Communication™ (NFC), etc., and other similar technologies.

In yet another example, the computing device 122A can identify the computing device 122B through the use of a Quick Response (QR) Code. For example, the genealogical display system 110 can generate a QR code for display on the computing device 122A that is uniquely associated to that computing device. An image of the displayed QR Code can be scanned by a camera of the computing device 122B. The genealogical display system 110 can identify the QR Code from the image of the QR Code. Based on the unique association between the QR Code and the computing device 122A, the genealogical display system 110 can identify the computing device 122A. That is, after QR Code identification, the computing device 122B can identify computing device 122A. Next, either or both of the computing devices 122A, 122B can transmit a graph generation request to the genealogical graphing system 110. For example, the connection request can include an identifier corresponding to the user of the computing device 122A and the response to the connection request can include an identifier corresponding to the user of the computing device 122B. Alternatively, after the second computing device 122B has identified the first computing device 122A through QR Code identification, the genealogical graphing system 110 can be automatically triggered to generate a genealogical graph 1208A and 1208B for display on the computing devices 122A and 122B, respectively.

Figure 40:
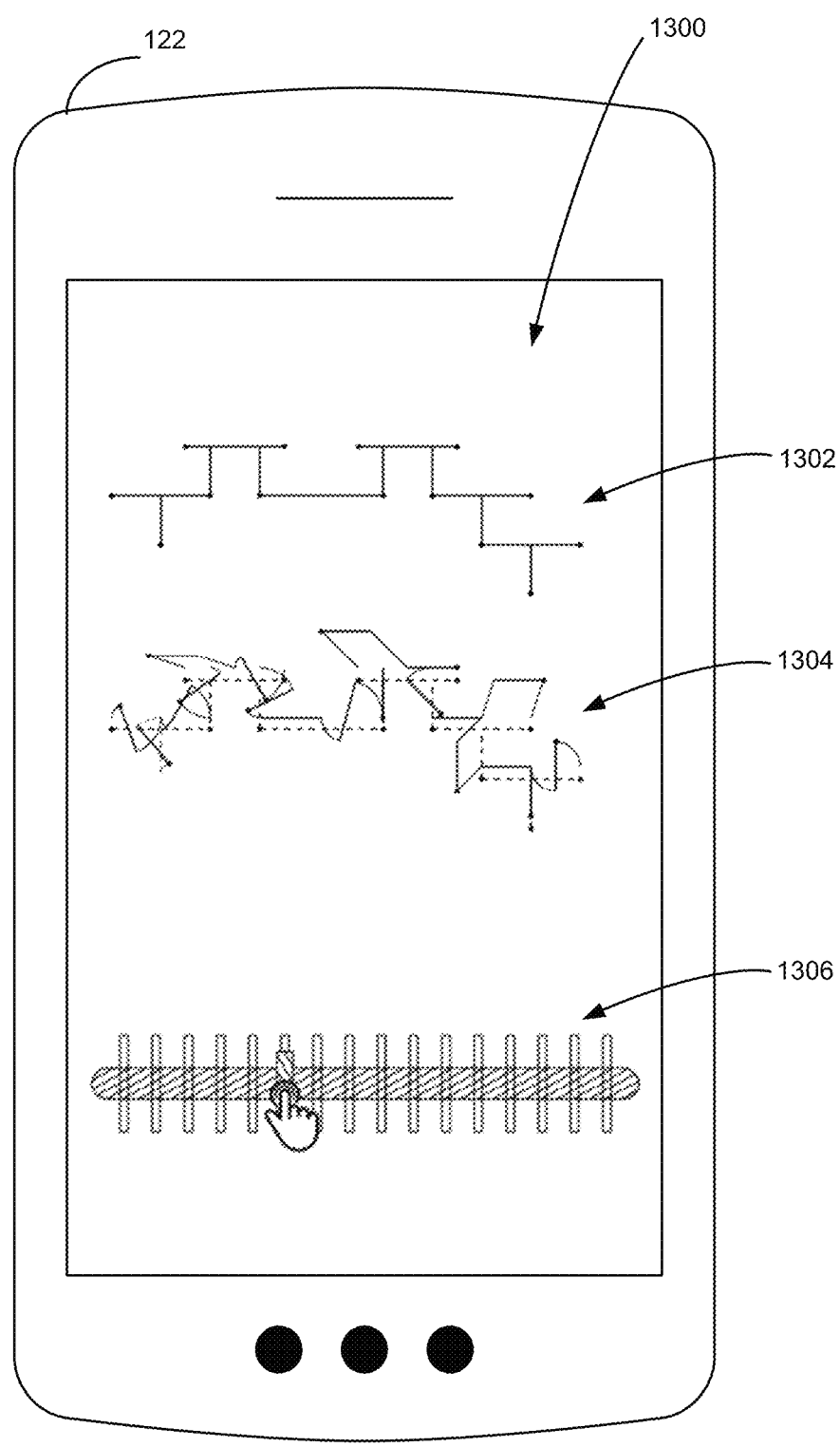
FIG. 40 shows a bot detection interface, in accordance with an embodiment.

In some embodiments, the genealogical graphing system 110 can generate a bot detection interface for detecting bot. FIG. 40 shows an example bot detection interface 1300.

When the genealogical graphing system 110 suspects the user is non-human (i.e. a robot), the genealogical graphing system 110 can issue a challenge in the bot detection interface 1300. The genealogical graphing system 110 may suspect the user is a bot when a large number of requests arrive from one computing device 122 or from an IP address. The challenge can be a puzzle that is easy for a human to solve, but cannot reliably be solved by the bot. For example, the bot detection interface 1300 can include a genealogical graph 1302 and a set of line segments 1304 transformable into the genealogical graph 1302. To be authenticated by the genealogical graphing system 110 as a human, the genealogical graphing system 110 needs to detect that the set of line segments 1304 is reordered to form the genealogical graph 1302.

The movement of the set of line segments 1304 can be adjusted via a slider 1306. The slider 1306 can be operated to translate a segment in X or Y directions, rotate a segment, etc. The slider 1306 can be a dial, in some embodiments.

In some embodiments, the genealogical graph 1302 may not be displayed in the bot detection interface 1300. The genealogical graphing system 110 can assign a finite number of concrete locations for the multi-parameter slider 1306. The number of locations must be made finite since it is difficult also for a human user to perfectly align, for example, three lines to be concurrent. The genealogical graphing system 110 can emit a sound and/or generate a vibration to indicate potential locations of the correct position. In this way, the audible sound and/or the vibration can make it easier for the human user.

The genealogical graphing system 110 may issue a challenge more than once during the user's interaction with the genealogical graphing system 110. Successfully completing the challenge can indicate that the user is human.

The challenge described above depends on the frequent failure of floating point arithmetic in geometric computations. For example, if two line segments form a polygonal chain, such as an L-shape, and if each segment is manipulated through an affine transformation with one parameter of the transformation entered through a one-dimensional slider, the user can easily move the one-dimensional slider until the L-shape is obtained. Similarly, if three lines that meet at a point are transformed such that they no longer intersect, it can be easy for a human to use a slider until the three lines meet at the point. However, it is difficult for a robot to identify when the three lines intersect. A robot computing the intersection point of the three lines can, in the vast majority of the cases, conclude that the three lines meet at three distinct points.

Figure 41:
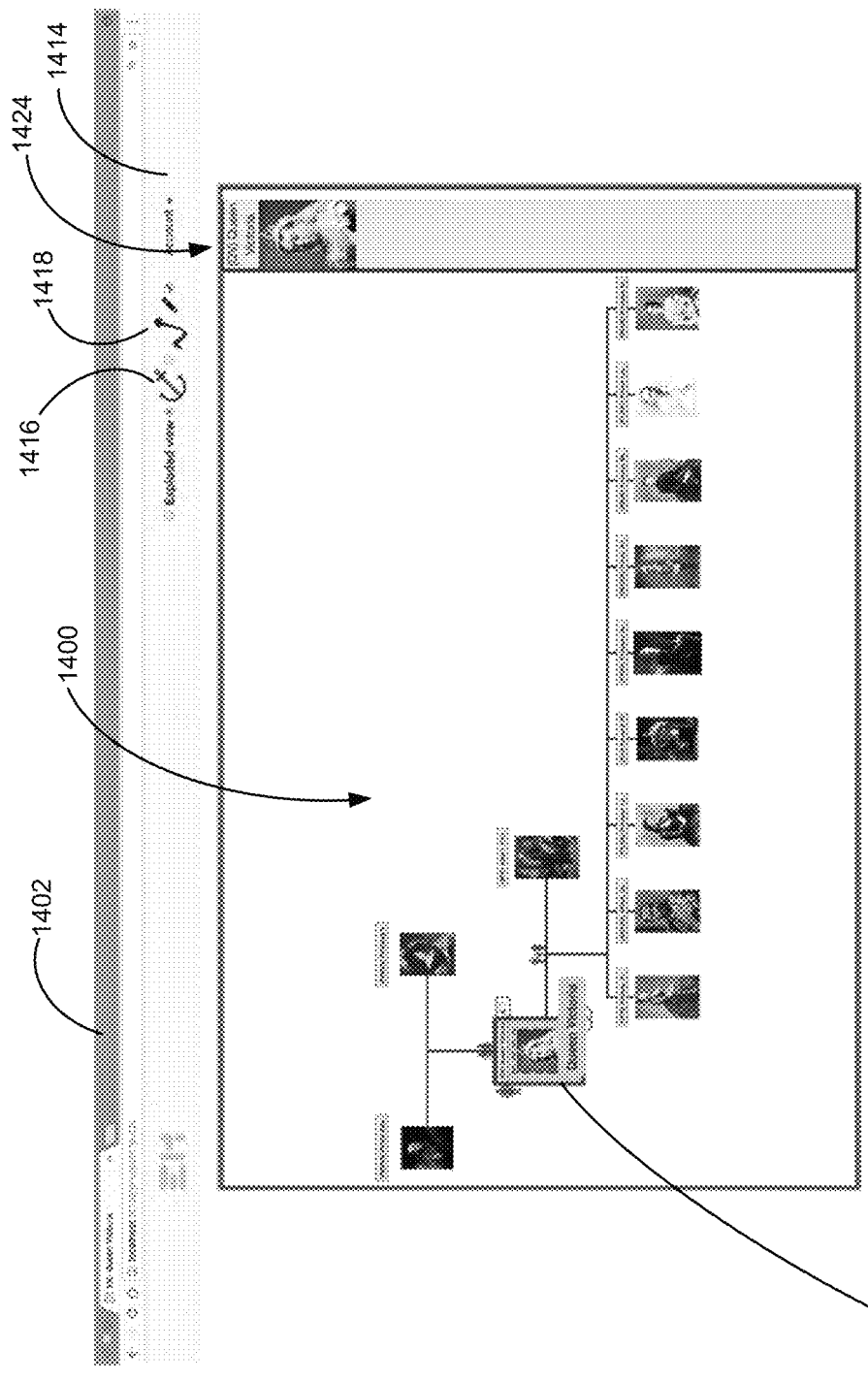
FIG. 41 shows an example genealogical graph displayed on a web browser, in accordance with an example embodiment.

Reference is now made to FIGS. 41-49 to illustrate example genealogical graphs on a display for illustrating example path interactions. FIG. 41 shows an example genealogical graph 1400 displayed on a web browser interface 1402. The web browser interface 1402 may be displayed via the display of the computing device 122 (not shown). The genealogical graph 1400 includes Queen Victoria (QV) as a target member 1452 and an initial member 1450, and shows first-degree relatives of QV.

A user viewing the genealogical graph 1400 can select any of the displayed nodes for interacting with the illustrated path of QV. For example, the genealogical graphing system 110 can receive a user input indicating the node associated with King Edward VII (Evii) (a son of QV) is selected. In response, the genealogical graphing system 110 can generate the genealogical graph 1404 shown in FIG. 41. In the genealogical graph 1404, Evii is the target member 1452, while QV remains the initial member 1450. As the target member 1452 is now Evii, the genealogical graph 1404 shows the first-degree relatives of Evii.

Figure 42:
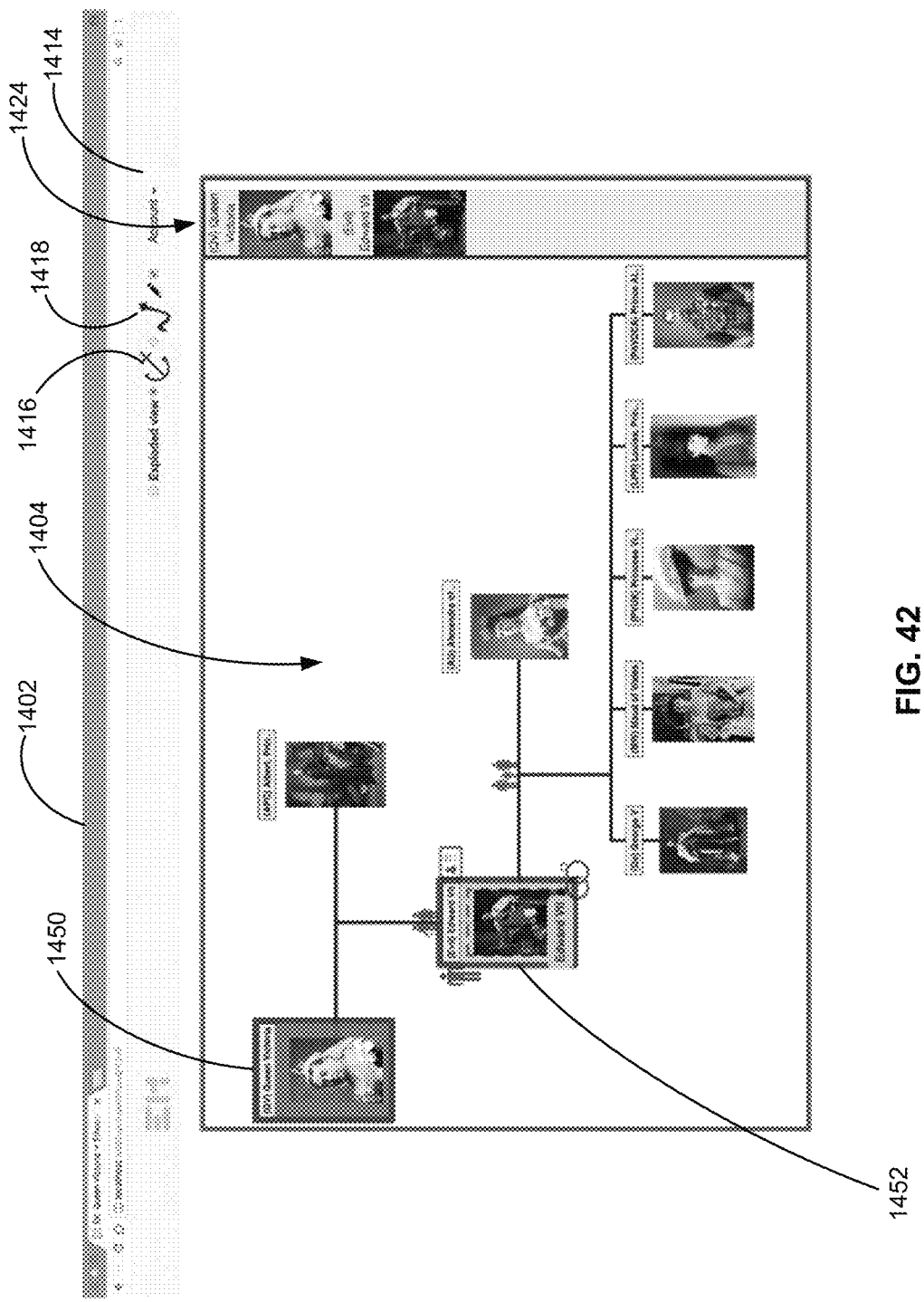
FIG. 42 shows another example genealogical graph following a user interaction received on the web browser of FIG. 41.

In another example embodiment, the genealogical graphing system 110 can receive a user input via the genealogical graph 1404 in FIG. 42 indicating the node associated with Alexandra of Denmark (AD) (spouse of Evii) is selected. In response, the genealogical graphing system 110 can generate the genealogical graph 1406 shown in FIG. 43. In genealogical graph 1406, AD becomes the target member 1452, while QV remains the initial member 1450. The genealogical graph 1406 displays the first-degree relatives of AD as a path between QV and AD even though QV is not a first-degree relative of AD.

Figure 43:
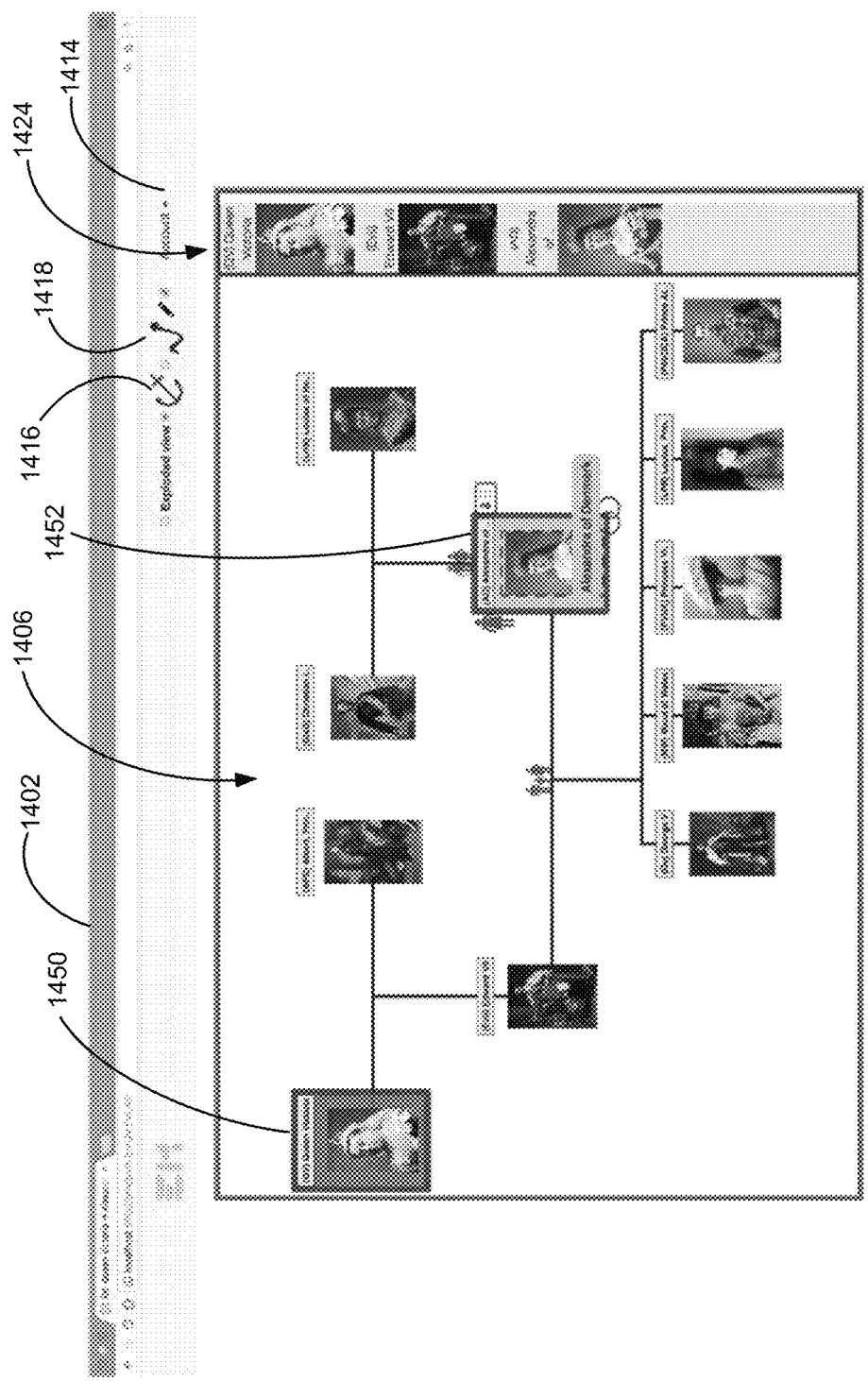
FIG. 43 shows another example genealogical graph following a user interaction received on the web browser of FIG. 42.

In another example embodiment, the genealogical graphing system 110 can receive a user input via the genealogical graph 1406 in FIG. 43 indicating the node associated with Christian IX of Denmark (CixD) (father of QD) is selected. In response, the genealogical graphing system 110 can generate the genealogical graph 1408 shown in FIG. 44. In the genealogical graph 1408, CixD becomes the target member 1452, while QV remains the initial member 1450. The genealogical graph 1408 displays the first-degree relatives of CixD as well as a path between QV and CixD even though QV is not a first-degree relative or second-degree relative of CixD.

Figure 44:
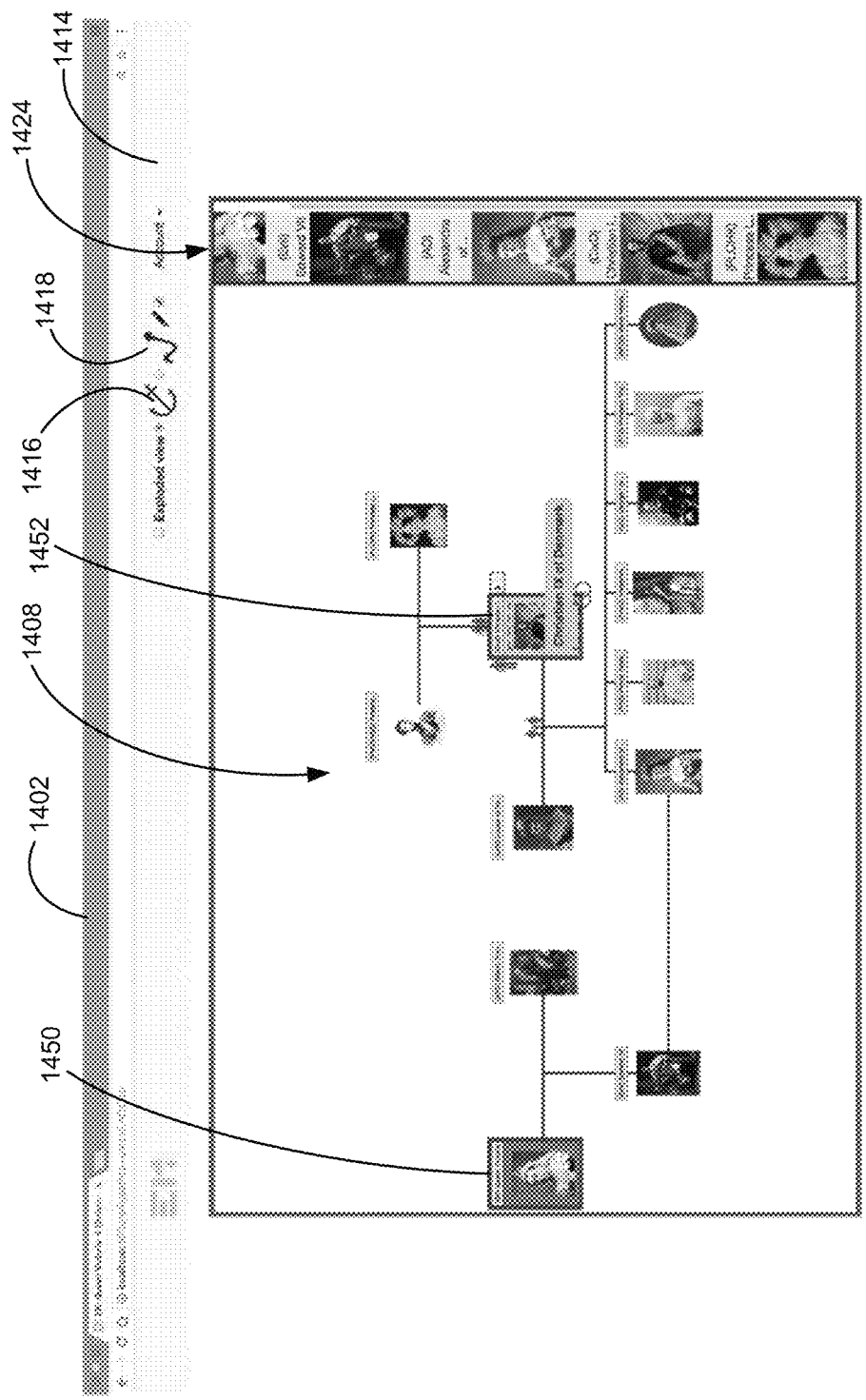
FIG. 44 shows another example genealogical graph following a user interaction received on the web browser of FIG. 43.

Via the genealogical graph 1408 in FIG. 44, the genealogical graphing system 110 can receive a user input indicating the node associated with Princess Louise Caroline of Hesse-Kassel (PLCHK) (mother of CixD) is selected. In response, the genealogical graphing system 110 can generate the genealogical graph 1410 shown in FIG. 45. In the genealogical graph 1410, PLCHK becomes the target member 1452, while QV remains the initial member 1450. As a result, the genealogical graph 1410 displays the first-degree relatives of PLCHK as well as a path between PLCHK and QV even though QV is not a first-degree, second-degree or third-degree relative of PLCHK.

Figure 45:
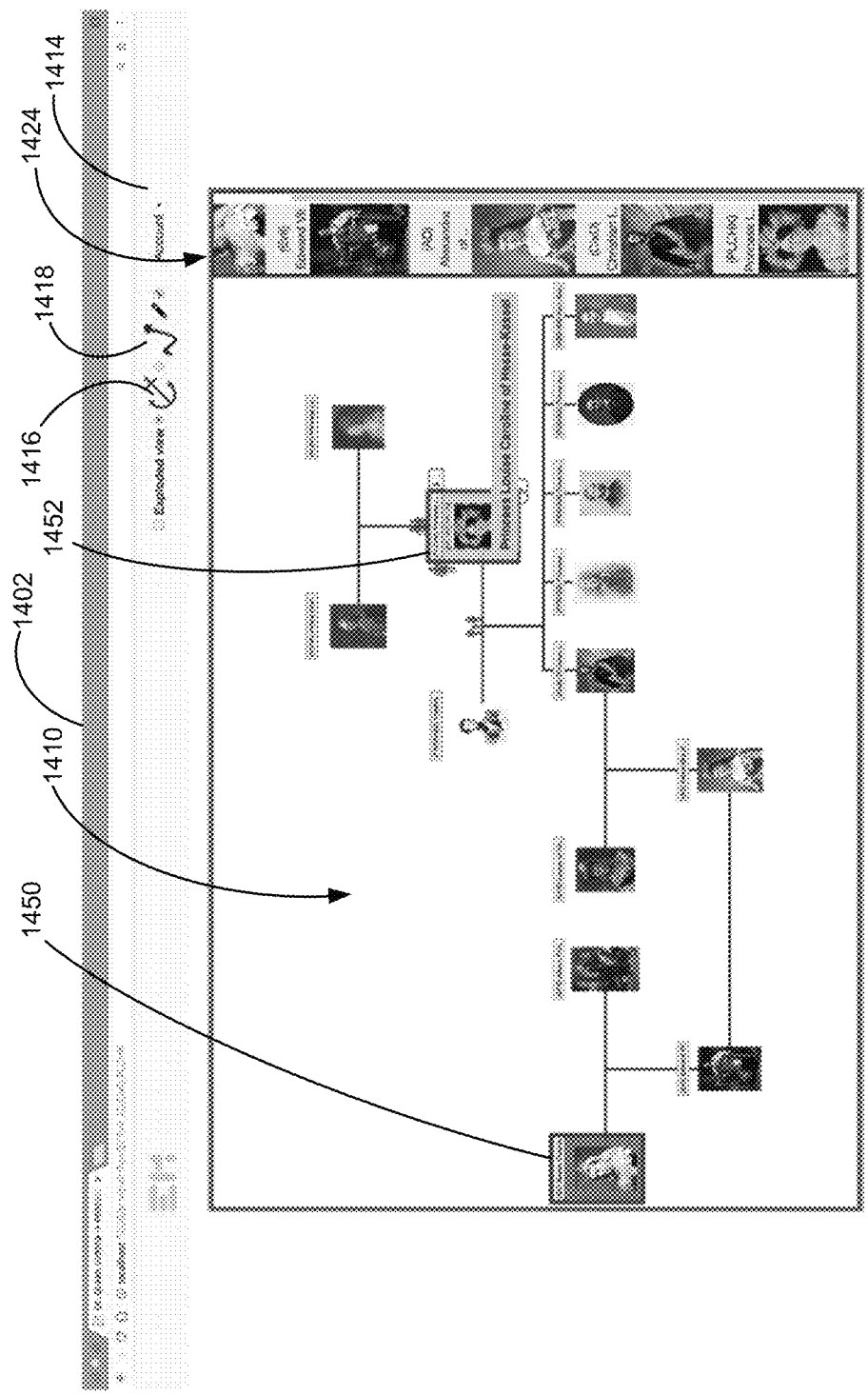
FIG. 45 shows another example genealogical graph following a user interaction received on the web browser of FIG. 44.
Figure 46:
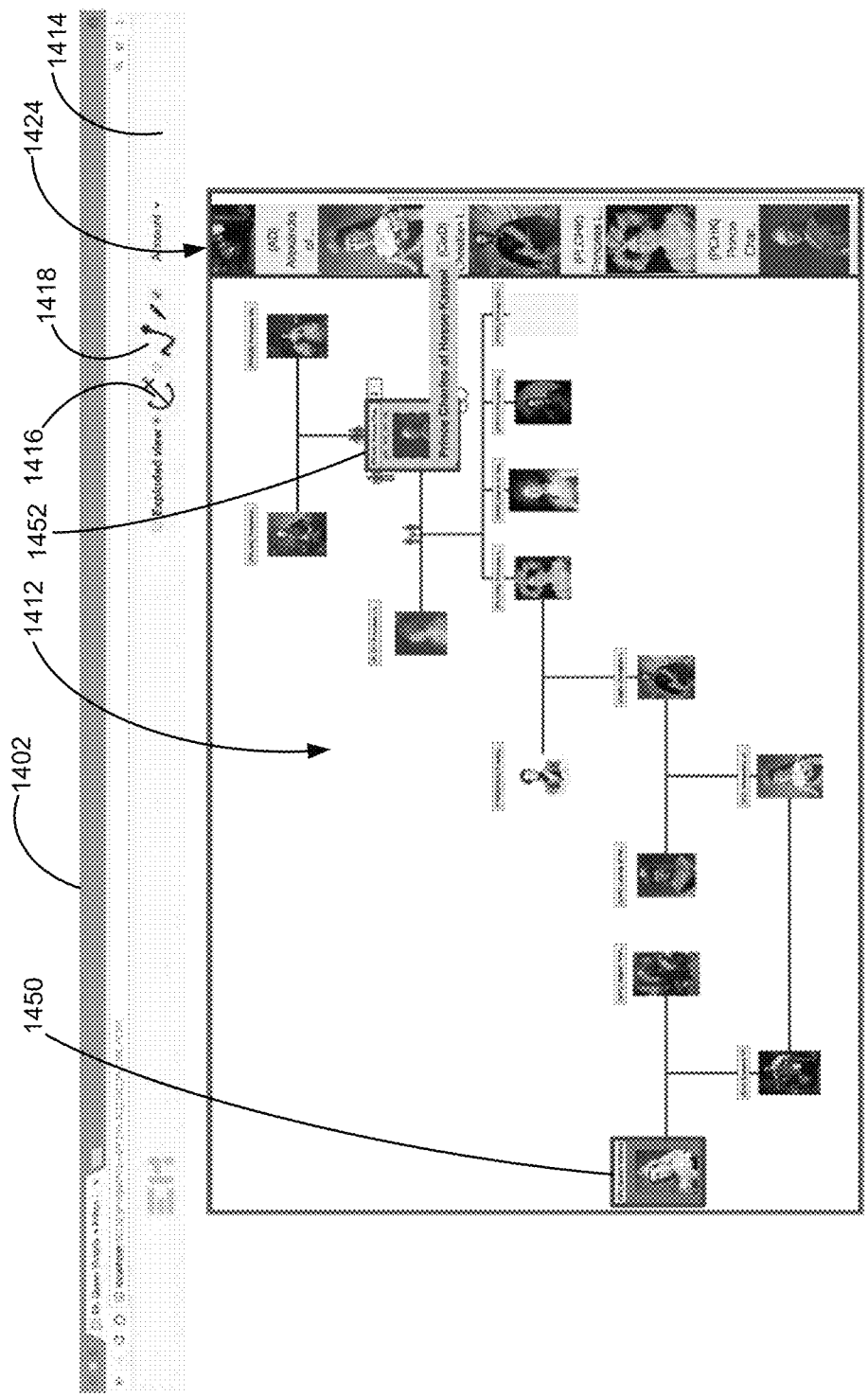
FIG. 46 shows another example genealogical graph following a user interaction received on the web browser of FIG. 45.

Via the genealogical graph 1410 in FIG. 45, the genealogical graphing system 110 can receive a user input indicating the node associated with Prince Charles of Hesse-Kassel (PCHK) (father of PLCHK) is selected. In response, the genealogical graphing system 110 can generate the genealogical graph 1412 shown in FIG. 46. In the genealogical graph 1412, PCHK becomes the target member 1452, while QV remains the initial member 1450. The genealogical graph 1412 displays the first-degree relatives of PCHK and a path between QV to PCHK even though QV is not a first-degree, second-degree, third-degree relative or fourth-degree relative of PCHK.

Referring to specifically to FIGS. 41 to 46, the genealogical graphs 1400, 1404, 1406, 1408, 1410 and 1412 may be referred to as "anchored graphs". When a genealogical graph is an anchored graph, the target node remains "anchored" to the initial node. That is, an anchored graph displays the complete path between the initial member 1450 and the target member 1452 on the web browser 1402. As shown in FIGS. 41 to 46, the web browser 1402 includes a toolbar 1414 having an anchor icon 1416. All genealogical graphs can, by default, begin as anchored graphs with the anchor icon 1416 selected (as shown in FIGS. 41 to 46).

On small display devices, and even on large display devices, when the path length of a genealogical graph becomes too long, it may be difficult to interact with the genealogical graph since the members on the genealogical graph may appear very small. For this reason, the toolbar 1414 also has progressive icon 1418 that can be selected to change the anchored graph into a "progressive graph", or vice versa. Progressive graphs can greatly increase usability on mobile devices with small display screens. For example, the genealogical graphing system 110 can receive a user input via the toolbar 1414 above genealogical graph 1412 shown in FIG. 46 indicating the wish to view a progressive graph of genealogical graph 1412. In response, the genealogical graphing system 110 can generate the progressive graph 1420 shown in FIG. 47. In progressive graph 1420, the target node remains anchored to the initial node and the URL remains exactly as before, showing the full path from the initial member 1450 to the target member 1452. However, in the progressive graph 1420, the user can only see first degree relatives of the target member 1452, thus making user interaction friendlier on small display devices. In the progressive graphs, the user can still backtrack one node at a time until they reach the initial member 1450.

Figure 47:
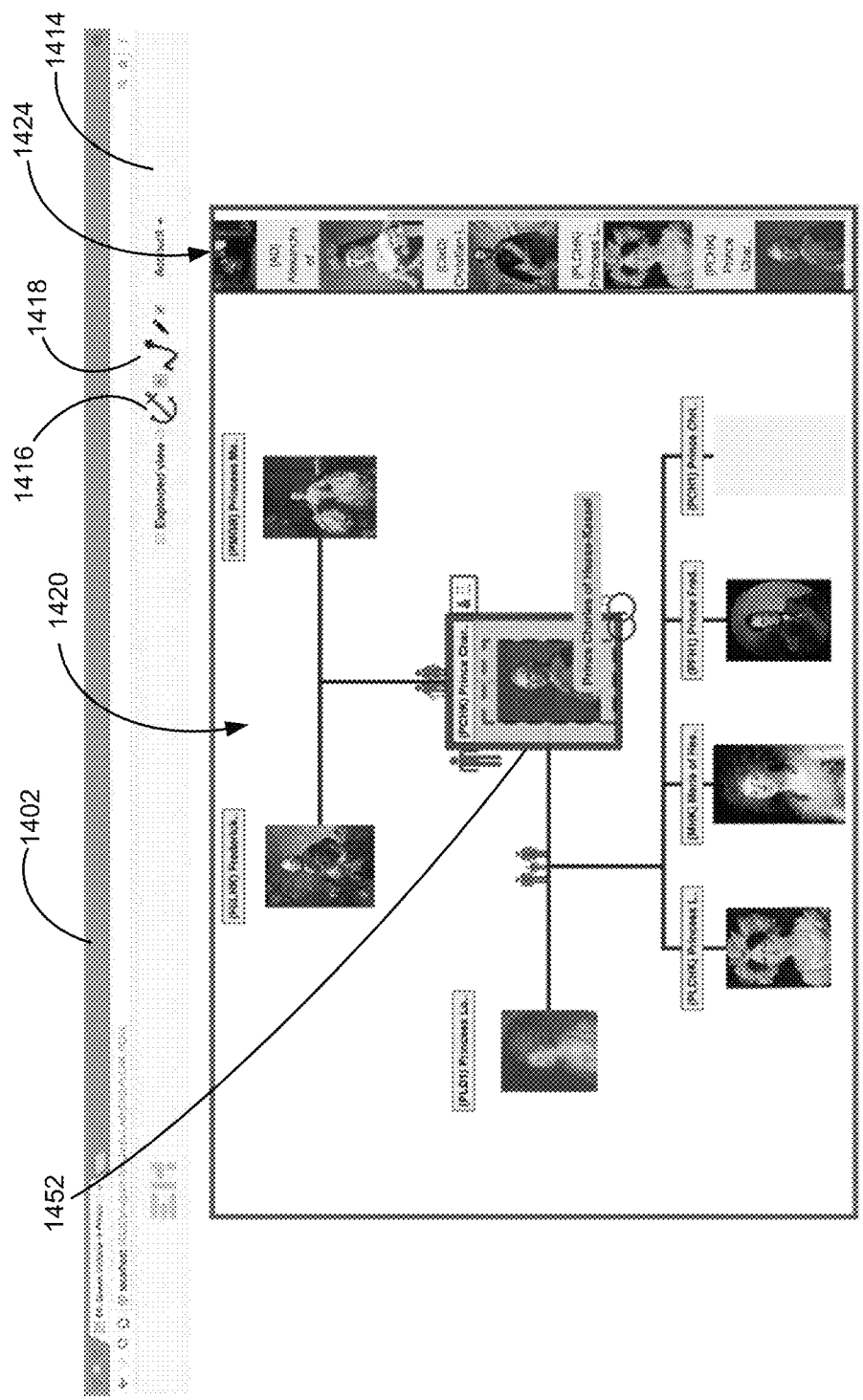
FIG. 47 is a progressive view of the example genealogical graph shown in FIG. 46.
Figure 48:
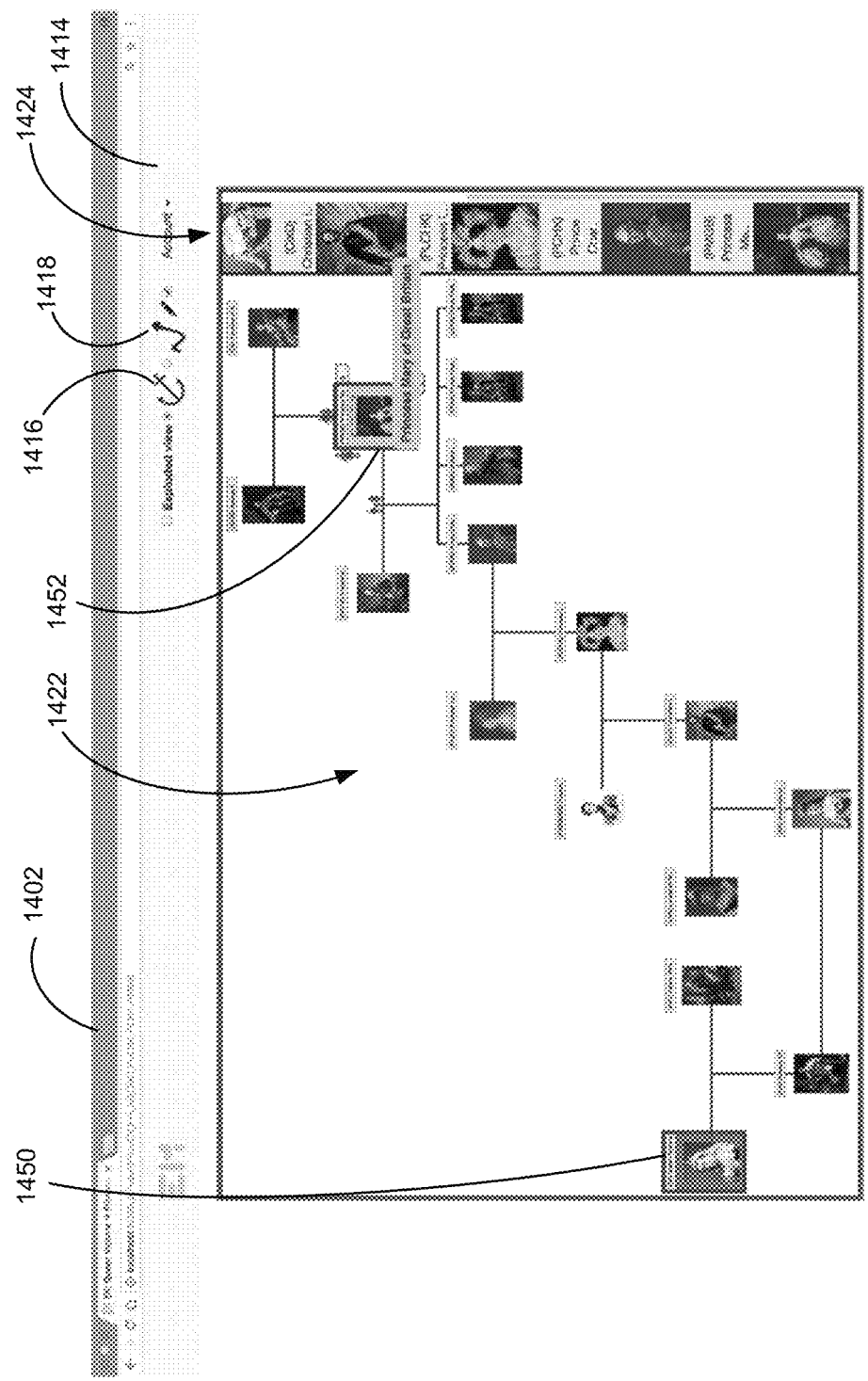
FIG. 48 shows another example genealogical graph following a user interaction received on the web browser of FIG. 47.

For example, via the progressive graph 1420 in FIG. 47, the genealogical graphing system 110 can receive a user input indicating the node associated with Princess Mary of Great Britain (PMGB) (mother of PCHK) is selected. This same user input may have also been made via the genealogical graph 1412 in FIG. 46; however, the input is easier to make via the progressive graph 1420 since the nodes are larger and easier to see. In response, the genealogical graphing system 110 can generate the genealogical graph 1422 shown in FIG. 48. In the genealogical graph 1422, PMGB becomes the target member 1452, while QV remains the initial member 1450. The genealogical graph 1422 displays the first-degree relatives of PMGB and a path between QV to PMGB even though QV is not a first-degree, second-degree, third-degree relative, fourth-degree or fifth-degree relative of PMGB. As shown in FIG. 48, by default, the genealogical graph 1422 is first drawn as an anchored graph with the anchor icon 1416 selected.

Referring to FIGS. 41 to 48 shows that the web browser 1402 also contains a list of relatives 1424. In the examples shown, the list of relatives 1424 is a vertical list on the right side of the web browser 1402; however, other configuration are possible. The list of relatives 1424 can enable the user to quickly navigate to a genealogical graph recently viewed. For example, the list of relatives 1424 can be scrolled vertically to show the most recent target members 1452 the user has visited.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to above as the computing device 122) may be a server, network appliance, embedded device, computer expansion module, a personal computer, laptop, personal data assistant, cellular telephone, smart-phone device, tablet computer, a wireless device or any other computing device capable of being configured to carry out the methods described herein.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the genealogical graphing system 110 may also be considered to be implemented as a non-transitory computer-readable storage medium, configured with a computer program, where the storage medium so configured causes a computer to operate in a specific and predefined manner to perform the functions described herein.

Furthermore, the genealogical graphing system 110, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various apparatuses or processes have been described above to provide an example of each claimed embodiment. No embodiment described above limits any claimed embodiment and any claimed embodiment may cover processes or apparatuses that differ from those described above. The claimed embodiments are not limited to apparatuses or processes having all of the features of any one apparatus or process described or to features common to multiple or all of the apparatuses described below.

A description of an embodiment with several components in communication with each other does not imply that all such components are required. On the contrary, a variety of optional components are described to illustrate the wide variety of possible embodiments of the present invention.

Further, although process steps, method steps, algorithms or the like may be described (in the disclosure above and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

While the above description provides examples of one or more apparatus, methods, or systems, it will be appreciated that other apparatus, methods, or systems may be within the scope of the claims as interpreted by one of skill in the art.

The invention claimed is:

1. A method of automatically drawing a genealogical graph for an initial member and a target member, the method comprising:
   receiving an initial member identifier identifying the initial member and a target member identifier identifying the target member by a processor by:
      operating a first computing device associated with a first user to display a machine-readable code uniquely associated with the first computing device;
      operating a second computing device associated with a second user to read the machine-readable code to identify the first computing device based on the unique association between the machine-readable code and the first computing device; and
      in response to identifying the first computing device, operating the processor to assign a first user identifier associated with the first user as the initial member identifier and to assign a second user identifier associated with the second user as the target member identifier;
   retrieving, from a memory, a set of genealogical data for the initial member and a set of genealogical data for the target member;
   determining whether a genealogical connection exists between the initial member and the target member;
   in response to determining the genealogical connection exists between the initial member and the target member, drawing the genealogical graph to illustrate at least a genealogical path between the initial member and the target member, wherein the genealogical path includes at least one linking member, and wherein the initial member, the target member, and the at least one linking member are represented by nodes connected by edges and each edge represents a first-degree relationship between nodes.

2. The method of claim 1, wherein the machine-readable code is a Quick Response (QR) Code.

3. The method of claim 1 wherein each of the nodes has a format chosen from a group consisting of an enriched node format, an interior node format, an adjusted interior node format, and a target node format.

4. The method of claim 3 wherein each node format includes a set of drawing instructions for each node relative to other nodes.

5. The method of claim 4 wherein the drawing instructions are recursive.

6. The method of claim 3 wherein at least one of the nodes has an enriched node format which includes additional data chosen from a group consisting of an image of the individual of the node, the sex of the individual, the name of the individual, the date of birth of the individual, the date of death of the individual.

7. The method of claim 1 wherein drawing the genealogical graph further includes drawing non-linking members, wherein a non-linking member is not part of the genealogical path connecting the initial member and the target member.

8. A system of automatically drawing a genealogical graph for an initial member and a target member, the system comprising:
   a memory for storing a set of genealogical data for the initial member and a set of genealogical data for the target member; and
   a processor, the processor operable to:
      receive, from at least one computing device, an initial member identifier identifying the initial member and a target member identifier identifying the target member by:
         operating a first computing device associated with a first user to display a first machine-readable code uniquely associated with the first computing device;
         detecting a second machine-readable code from a second computing device associated with a second user; and
         assigning a first user identifier associated with the first user as the initial member identifier and a second user identifier associated with the second user as the target member identifier;
      retrieve, from the memory, the set of genealogical data for the initial member and the set of genealogical data for the target member;
      determine whether a genealogical connection exists between the initial member and the target member; and
      in response to determining the genealogical connection exists between the initial member and the target member, draw the genealogical graph to illustrate at least a genealogical path between the initial member and the target member, wherein the genealogical path includes at least one linking member, and wherein the initial member, the target member, and the at least one linking member are represented by nodes connected by edges and each edge represents a first-degree relationship between nodes.

9. The system of claim 8, wherein the processor:
   operates a first computing device associated with a first user to detect a second computing device associated with a second user within a proximity threshold; and
   assigns, in response to detecting the second computing device by the first computing device, a first user identifier associated with the first user as the initial member identifier and assigns a second user identifier associated with the second user as the target member identifier.

10. The of claim 8, wherein the processor operates to:
    display an image showing one or more members;
    receive, from the at least one computing device, a user input selecting a first member and a second member from the one or more members shown on the image;
    determine a first member identifier corresponding to the selected first member and a second member identifier corresponding to the selected second member; and
    assign the first member identifier as the initial member and the second member identifier as the target member identifier.

11. The system of claim 8, wherein the processor operates to:
    detect a display size of a computing device for displaying the genealogical graph; and
    adjust the genealogical graph for the detected display size.

12. The system of claim 11 wherein adjusting the genealogical graph for the detected display size includes omitting non-linking members from the genealogical graph, wherein a non-linking member is not part of the genealogical path.

13. The system of claim 11 wherein adjusting the genealogical graph for the detected display size includes adding at least one non-linking member to the genealogical graph, wherein the at least one non-linking member is not part of the genealogical path.

14. The system of claim 8, wherein the processor operates to:
- display an initial member node for the initial member;
- display a target node for the target member;
- display a linking member node for each linking member identified in the genealogical data for the target member; and
- connect the initial member node, the target node and each linking member node based on the sets of genealogical data for the target member and the initial member.

15. The system of claim 14 wherein each of the nodes has a node format chosen from a group consisting of an enriched node format, an interior node format, an adjusted interior node format, and a target node format.

16. The system of claim 15 wherein each node format includes a set of drawing instructions for the processor to draw each node in the genealogical graph.

17. The system of claim 8, wherein the processor operates to:
- receive, via a genealogical degree selection control, a genealogical degree selection defining a genealogical degree of genealogical data to display in the genealogical graph.

18. The system of claim 8 wherein the machine-readable code is a Quick Response (QR) Code.

19. A system of automatically drawing a genealogical graph for an initial member and a target member, the system comprising:
- a memory for storing a set of genealogical data for the initial member and a set of genealogical data for the target member; and
- a processor, the processor operable to:
  - receive, from at least one computing device, an initial member identifier identifying the initial member and a target member identifier identifying the target member;
  - retrieve, from the memory, the set of genealogical data for the initial member and the set of genealogical data for the target member
  - determine whether a genealogical connection exists between the initial member and the target member;
  - in response to determining the genealogical connection exists between the initial member and the target member, draw the genealogical graph to illustrate at least a genealogical path between the initial member and the target member, wherein the genealogical path includes at least one linking member, and wherein the initial member, the target member, and the at least one linking member are represented by nodes connected by edges and each edge represents a first-degree relationship between nodes;
  - detect a display size of a computing device for displaying the genealogical graph; and
  - adjust the genealogical graph for the detected display size, wherein adjusting the genealogical graph for the detected display size includes omitting non-linking members from the genealogical graph, wherein a non-linking member is not part of the genealogical path.

* * * * *